(12) United States Patent
Brice et al.

(10) Patent No.: US 7,879,564 B2
(45) Date of Patent: Feb. 1, 2011

(54) USE OF THE RECEPTOR GPR86

(75) Inventors: Nicola Brice, Cambridge (GB); Mark Carlton, Cambridge (GB); John Dixon, Cambaridge (GB); Alan Hendrick, Cambridge (GB); Isabelle Malinge, Cambridge (GB); Sophie Messager, Cambridge (GB); Dirk Zahn, Cambridge (GB)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 11/644,011

(22) Filed: Dec. 21, 2006

(65) Prior Publication Data

US 2007/0248545 A1 Oct. 25, 2007

Related U.S. Application Data

(63) Continuation-in-part of application No. PCT/GB2005/002601, filed on Jul. 1, 2005.

(60) Provisional application No. 60/586,513, filed on Jul. 9, 2004, provisional application No. 60/683,471, filed on May 20, 2005.

(30) Foreign Application Priority Data

Jul. 1, 2004 (GB) .................................. 0414798.9
May 19, 2005 (GB) .................................. 0510253.8

(51) Int. Cl.
*G01N 33/53* (2006.01)
*G01N 33/566* (2006.01)
(52) U.S. Cl. .............................. 435/7.2; 435/6; 436/501
(58) Field of Classification Search ........................ None
See application file for complete search history.

(56) References Cited

U.S. PATENT DOCUMENTS 6,358,695 B1  3/2002  Sathe et al.

2003/0059857 A1  3/2003  Zhang et al.
2003/0165989 A1  9/2003  Au-Young et al.

FOREIGN PATENT DOCUMENTS

| WO | WO 01/27153 | 4/2001 |
| WO | WO 03/014731 | 2/2003 |
| WO | WO2004/040000 | 5/2004 |
| WO | WO 2004/082571 | 9/2004 |

OTHER PUBLICATIONS

Kugelgen, Pharmacological profiles of cloned mammalian P2Y-receptor subtypes, Pharmacol. Ther., 110(3): 415-432, 2006.*
Matthaei, Genetically manipulated mice: a powerful tool with unsuspected caveats. J Physiol. 582(Pt 2):481-8, 2007.*
Didier Communi, et al., Identification of a Novel Human ADP Receptor Coupled to $G_1$*, The Journal of Biological Chemistry (2001) vol. 276, No. 44, p. 41479-41485.
Marta Fumagalli, et al., Cloning, Pharmacological Characterization and Distribution of the Rat G-Protein-Coupled $P2Y_{13}$ Receptor, Biochemical Pharmacology (2004) vol. 68, p. 113-124.
Evi Kostenis, Is $G\alpha_{16}$ the Optimal Tool for Fishing Ligands of Orphan G-Protein-Coupled Receptors? Trends in Pharmacological Sciences (2001) vol. 22, No. 11, p. 560-564.
Frederic Marteau, et al., Pharmacological Characterization of the Human $P2Y_{13}$ Receptor, Molecular Pharmacology (1995) vol. 64, No. 1, p. 104-112.
Fang L. Zhang, et al., $P2Y_{13}$: Identification and Characterization of a Novel $G\alpha i$-Coupled ADP Receptor From Human and Mouse, The Journal of Pharmacology and Experimental Therapeutics ( 2002) vol. 301, No. 2, p. 705-713.

* cited by examiner

*Primary Examiner*—Christine J Saoud
*Assistant Examiner*—Jon M Lockard
(74) *Attorney, Agent, or Firm*—Banner & Witcoff, Ltd.

(57) ABSTRACT

We describe a method of identifying a molecule suitable for the treatment, prophylaxis or alleviation of a GPR86 associated disease, in particular inflammatory disease or pain, the method comprising determining whether a candidate molecule is an agonist or antagonist of GPR86 polypeptide, in which the GPR86 polypeptide comprises the amino acid sequence shown in SEQ ID NO: 3 or SEQ ID NO: 5 or SEQ ID NO: 7, a fragment thereof or a sequence which is at least 90% identical thereto.

9 Claims, 9 Drawing Sheets

***$p<0.001$ compared to ipsi (wt)
**$p<0.01$ compared to ipsi (wt)
++$p<0.01$ compared to contra (wt)
+$p<0.05$ compared to contra (wt)

us 7,879,564 B2

SEQUENCE LISTING

<160> NUMBER OF SEQ ID NOS: 21

<210> SEQ ID NO 1
<211> LENGTH: 2766
<212> TYPE: DNA
<213> ORGANISM: Homo sapiens

<400> SEQUENCE: 1

```
tcatttgtag gctgaactaa tgactgccgc cataagaaga cagagagaac tgagtatcct      60
cccaaaggtg acactggaag caatgaacac cacagtgatg caaggcttca acagatctga     120
gcggtgcccc agagacactc ggatagtaca gctggtattc ccagccctct acacagtggt     180
tttcttgacc ggcatcctgc tgaatacttt ggctctgtgg gtgtttgttc acatccccag     240
ctcctccacc ttcatcatct acctcaaaaa cactttggtg gccgacttga taatgacact     300
catgcttcct ttcaaaatcc tctctgactc acacctggca ccctggcagc tcagagcttt     360
tgtgtgtcgt ttttcttcgg tgatattta tgagaccatg tatgtgggca tcgtgctgtt     420
agggctcata gcctttgaca gattcctcaa gatcatcaga cctttgagaa atatttttct     480
aaaaaaacct gtttttgcaa aaacggtctc aatcttcatc tggttctttt tgttcttcat     540
```

```
ctccctgcca aatatgatct tgagcaacaa ggaagcaaca ccatcgtctg tgaaaaagtg      600
tgcttcctta aaggggcctc tggggctgaa atggcatcaa atggtaaata acatatgcca      660
gtttattttc tggactgttt ttatcctaat gcttgtgttt tatgtggtta ttgcaaaaaa      720
agtatatgat tcttatagaa agtccaaaag taaggacaga aaaaacaaca aaaagctgga      780
aggcaaagta tttgttgtcg tggctgtctt ctttgtgtgt tttgctccat ttcatttttgc     840 cagagttcca tatactcaca gtcaaaccaa caataagact gactgtagac tgcaaaatca      900
actgtttatt gctaaagaaa caactctctt tttggcagca actaacatttt gtatggatcc     960 cttaatatac atattcttat gtaaaaaatt cacagaaaag ctaccatgta tgcaagggag     1020
aaagaccaca gcatcaagcc aagaaaatca tagcagtcag acagacaaca taaccttagg     1080
ctgacaactg tacatagggt taacttctat ttattgatga acttccgta gataatgtgg     1140 aaatcaaatt taaccaagaa aaaagattg gaacaaatgc tctcttacat tttattatcc      1200
tggtgtacag aaaagattat ataaaattta aatccacata gatctattca taagctgaat     1260
gaaccattac taagagaatg caacaggata caaatggcca ctagaggtca ttatttcttt     1320
cttctttttt ttttttttta atttcaagag catttcactt taacattttg gaaaagacta     1380
aggagaaacg tatatcccta caaacctccc ctccaaacac cttctcacat tctttttccac    1440 aattcacata acactactgc ttttgtgccc cttaaatgta gatatgtgct gaaagaaaaa     1500
aaaaacgccc aactcttgaa gtccattgct gaaaactgca gccagggggtt gaaagggatg    1560 cagacttgaa gagtctgagg aactgaagtg ggtcagcaag acctctgaaa tcctgggtaa     1620
aggattttct ccttacaatt acaaacagcc tctttcacat tacaataata taccatagga     1680
ggcacaagca ccattattaa gccactttgc ttacacctta agtgtgtaca attcaagtgt     1740
gagaatgctg tgttaactat tctttggaat tctccttctg tccagcaaat actctaatga     1800
tggttaaaca tggcacctac tcagcaatgc cttcctggac cacaacccct atcccctgc     1860 cccaccctcc tcattaaaaa caaatacttc tactgtttgg gtgtgtgata gggttctcaa     1920
tgcagatctc cctttttctag ttagctatat tcttgactgc atccgctaaa aatgttaaag    1980
cttcttgaga gacagacatg ccagatttttc ttggtatctc ccataatacg acctacagtc    2040
catggtctac agatgtttta aatagaattg ctattctcga tacatacaaa gacgtaattg     2100
ctgacccaca atcagtaaca tccatattgg gagatttttc aaaggatggt gaccctgctt     2160
gtatttattt accttggtat ttttttcttgc atccttctgt gattcaaaaa agtaaaatgt     2220
ggctttctga aatgatggat aagagtctac atcttctaga aaaaatacat aaaggagtag     2280
ttaagctctg taaatgtgcc acgagctcca acacgaccat cgtagggtga agcccacgtt    2340
ttcttccatg gcctcaaagg ccctagaact tgcctacctt tctggcctta cctcctagct    2400
acttatccat ctcttgaact ttatactctt gtataaattt ctaactttca gaaaatgcca    2460
tactctgttt tggcaccaca catgtatatt tccccctggt acacttggaa gactcttatc    2520
catctgtgaa accctatgtt gtcatcactt ggtccatgaa atattacctg ccaatatcc     2580 caccatcacc tcaaacccaa tcaccccctc ctctgtatgc tgtcacacct atattattaa    2640
acttatcaca ttgcattgta attacttcct gacctttgta tctactcttt tagtaactga    2700
tgtatatatc tgaaaggaga gattgtttca ttgtgcaatc aataaatgtt tgataaaata    2760
aagccc                                                               2766
```

<210> SEQ ID NO 2
<211> LENGTH: 1065

-continued

```
<212> TYPE: DNA
<213> ORGANISM: Homo sapiens

<400> SEQUENCE: 2
atgactgccg ccataagaag acagagagaa ctgagtatcc tcccaaaggt gacactggaa      60
gcaatgaaca ccacagtgat gcaaggcttc aacagatctg agcggtgccc cagagacact     120
cggatagtac agctggtatt cccagccctc tacacagtgg ttttcttgac cggcatcctg     180
ctgaatactt tggctctgtg ggtgtttgtt cacatcccca gctcctccac cttcatcatc     240
tacctcaaaa acactttggt ggccgacttg ataatgacac tcatgcttcc tttcaaaatc     300
ctctctgact cacacctggc accctggcag ctcagagctt ttgtgtgtcg ttttcttcg      360 gtgatatttt atgagaccat gtatgtgggc atcgtgctgt tagggctcat agcctttgac     420
agattcctca agatcatcag acctttgaga aatattttc taaaaaaacc tgtttttgca     480
aaaacggtct caatcttcat ctggttcttt ttgttcttca tctccctgcc aaatatgatc     540
ttgagcaaca aggaagcaac accatcgtct gtgaaaaagt gtgcttcctt aaaggggcct     600
ctggggctga atggcatca atggtaaat acatatgcc agtttatttt ctggactgtt       660
tttatcctaa tgcttgtgtt ttatgtggtt attgcaaaaa agtatatga ttcttataga     720 aagtccaaaa gtaaggacag aaaaaacaac aaaaagctgg aaggcaaagt atttgttgtc     780
gtggctgtct tctttgtgtg ttttgctcca tttcattttg ccagagttcc atatactcac     840
agtcaaacca acaataagac tgactgtaga ctgcaaaatc aactgtttat tgctaaagaa     900
acaactctct ttttggcagc aactaacatt tgtatggatc ccttaatata catattctta     960
tgtaaaaaat tcacagaaaa gctaccatgt atgcaaggga aaagaccac agcatcaagc    1020 caagaaaatc atagcagtca gacagacaac ataaccttag gctga                   1065

<210> SEQ ID NO 3
<211> LENGTH: 354
<212> TYPE: PRT
<213> ORGANISM: Homo sapiens

<400> SEQUENCE: 3

Met Thr Ala Ala Ile Arg Arg Gln Arg Glu Leu Ser Ile Leu Pro Lys
1               5                   10                  15

Val Thr Leu Glu Ala Met Asn Thr Thr Val Met Gln Gly Phe Asn Arg
            20                  25                  30

Ser Glu Arg Cys Pro Arg Asp Thr Arg Ile Val Gln Leu Val Phe Pro
        35                  40                  45

Ala Leu Tyr Thr Val Val Phe Leu Thr Gly Ile Leu Leu Asn Thr Leu
    50                  55                  60

Ala Leu Trp Val Phe Val His Ile Pro Ser Ser Ser Thr Phe Ile Ile
65                  70                  75                  80

Tyr Leu Lys Asn Thr Leu Val Ala Asp Leu Ile Met Thr Leu Met Leu
                85                  90                  95

Pro Phe Lys Ile Leu Ser Asp Ser His Leu Ala Pro Trp Gln Leu Arg
            100                 105                 110

Ala Phe Val Cys Arg Phe Ser Ser Val Ile Phe Tyr Glu Thr Met Tyr
        115                 120                 125

Val Gly Ile Val Leu Leu Gly Leu Ile Ala Phe Asp Arg Phe Leu Lys
    130                 135                 140

Ile Ile Arg Pro Leu Arg Asn Ile Phe Leu Lys Lys Pro Val Phe Ala
145                 150                 155                 160
```

```
Lys Thr Val Ser Ile Phe Ile Trp Phe Phe Leu Phe Ile Ser Leu
                165                 170                 175

Pro Asn Met Ile Leu Ser Asn Lys Glu Ala Thr Pro Ser Ser Val Lys
            180                 185                 190

Lys Cys Ala Ser Leu Lys Gly Pro Leu Gly Leu Lys Trp His Gln Met
        195                 200                 205

Val Asn Asn Ile Cys Gln Phe Ile Phe Trp Thr Val Phe Ile Leu Met
    210                 215                 220

Leu Val Phe Tyr Val Val Ile Ala Lys Lys Val Tyr Asp Ser Tyr Arg
225                 230                 235                 240

Lys Ser Lys Ser Lys Asp Arg Lys Asn Asn Lys Lys Leu Glu Gly Lys
                245                 250                 255

Val Phe Val Val Val Ala Val Phe Phe Val Cys Phe Ala Pro Phe His
            260                 265                 270

Phe Ala Arg Val Pro Tyr Thr His Ser Gln Thr Asn Asn Lys Thr Asp
        275                 280                 285

Cys Arg Leu Gln Asn Gln Leu Phe Ile Ala Lys Glu Thr Thr Leu Phe
    290                 295                 300

Leu Ala Ala Thr Asn Ile Cys Met Asp Pro Leu Ile Tyr Ile Phe Leu
305                 310                 315                 320

Cys Lys Lys Phe Thr Glu Lys Leu Pro Cys Met Gln Gly Arg Lys Thr
                325                 330                 335

Thr Ala Ser Ser Gln Glu Asn His Ser Ser Gln Thr Asp Asn Ile Thr
            340                 345                 350

Leu Gly

<210> SEQ ID NO 4
<211> LENGTH: 1014
<212> TYPE: DNA
<213> ORGANISM: Mus musculus

<400> SEQUENCE: 4
atgctcggga caatcaacac cactgggatg cagggcttca acaagtctga gcggtgcccc      60
agggacactc ggatgacaca gctgctgttc ccggttctct atactgtggt cttcctggca     120
ggcatcctgc tgaacaccgt ggccctctgg gtgttcgtcc acatcccag caattccacc     180
tttatcgtct acctcaagaa cactctggtg cagacttga taatggcact catgctgcct     240
ttcaaaatcc tttccgactc acaccttgcg ccctggcagc tccgaggatt tgtgtgcacg     300
ctctcctccg tggtcttcta tgagacgatg tatgtgggta tcatgatgct gggcctcatc     360
gctttcgaca ggttcctcaa gatcatcatg ccgttcagga aacctttgt caaaaagacg     420
gctttcgcaa aaacagtctc catttccgtc tggtccctga tgttcttcat ctccctgcca     480
aacatgatct tgaacaagga ggcaacgcca tcatccgtga agaagtgtgc atctttgaag     540
agtcccttg ggctgtggtg gcatcaggtg gtcagtcaca cctgccagtt catttctgg     600
gctgtgttta ttctgatgct tctgttttat gcggtgatta ccaaaaaggt gtacaactcc     660
tataggaagt ttaggagtaa ggacagcagg cacaagcggc tggaggtgaa ggtatttatc     720
gtcatggctg tcttctttgt ctgctttgcc ccactgcatt ttgtcagaat accatacact     780
tacagtcaaa ccaccaataa gactgactgt aggttagaaa accagctgtt tattgctaaa     840
gaagcaactc tctttctggc aacaactaac atttgtatgg accccttaat atacataatt     900
ttatgcaaga agttcacaca aaaggtgcca tgtgtgagat ggggaaaggc aagaacagca     960
ggatcaagcg aagaccacca cagtagtcag acagacaaca tcaccctagc ctga          1014
```

```
<210> SEQ ID NO 5
<211> LENGTH: 338
<212> TYPE: PRT
<213> ORGANISM: Mus musculus

<400> SEQUENCE: 5

Met Leu Gly Thr Ile Asn Thr Thr Gly Met Gln Gly Phe Asn Lys Ser
1               5                   10                  15

Glu Arg Cys Pro Arg Asp Thr Arg Met Thr Gln Leu Leu Phe Pro Val
            20                  25                  30

Leu Tyr Thr Val Val Phe Leu Ala Gly Ile Leu Leu Asn Thr Val Ala
        35                  40                  45

Leu Trp Val Phe Val His Ile Pro Ser Asn Ser Thr Phe Ile Val Tyr
50                  55                  60

Leu Lys Asn Thr Leu Val Ala Asp Leu Ile Met Ala Leu Met Leu Pro
65                  70                  75                  80

Phe Lys Ile Leu Ser Asp Ser His Leu Ala Pro Trp Gln Leu Arg Gly
                85                  90                  95

Phe Val Cys Thr Leu Ser Ser Val Val Phe Tyr Glu Thr Met Tyr Val
            100                 105                 110

Gly Ile Met Met Leu Gly Leu Ile Ala Phe Asp Arg Phe Leu Lys Ile
        115                 120                 125

Ile Met Pro Phe Arg Lys Thr Phe Val Lys Lys Thr Ala Phe Ala Lys
130                 135                 140

Thr Val Ser Ile Ser Val Trp Ser Leu Met Phe Phe Ile Ser Leu Pro
145                 150                 155                 160

Asn Met Ile Leu Asn Lys Glu Ala Thr Pro Ser Ser Val Lys Lys Cys
                165                 170                 175

Ala Ser Leu Lys Ser Pro Leu Gly Leu Trp Trp His Gln Val Val Ser
            180                 185                 190

His Thr Cys Gln Phe Ile Phe Trp Ala Val Phe Ile Leu Met Leu Leu
        195                 200                 205

Phe Tyr Ala Val Ile Thr Lys Lys Val Tyr Asn Ser Tyr Arg Lys Phe
210                 215                 220

Arg Ser Lys Asp Ser Arg His Lys Arg Leu Glu Val Lys Val Phe Ile
225                 230                 235                 240

Val Met Ala Val Phe Phe Val Cys Phe Ala Pro Leu His Phe Val Arg
                245                 250                 255

Ile Pro Tyr Thr Tyr Ser Gln Thr Thr Asn Lys Thr Asp Cys Arg Leu
            260                 265                 270

Glu Asn Gln Leu Phe Ile Ala Lys Glu Ala Thr Leu Phe Leu Ala Thr
        275                 280                 285

Thr Asn Ile Cys Met Asp Pro Leu Ile Tyr Ile Leu Cys Lys Lys
290                 295                 300

Phe Thr Gln Lys Val Pro Cys Val Arg Trp Gly Lys Ala Arg Thr Ala
305                 310                 315                 320

Gly Ser Ser Glu Asp His His Ser Ser Gln Thr Asp Asn Ile Thr Leu
                325                 330                 335

Ala Glx

<210> SEQ ID NO 6
<211> LENGTH: 2717
<212> TYPE: DNA
<213> ORGANISM: Homo sapiens
```

```
<400> SEQUENCE: 6
tatgtttatt ggtaacaggt gacactggaa gcaatgaaca ccacagtgat gcaaggcttc        60
aacagatctg agcggtgccc cagagacact cggatagtac agctggtatt cccagccctc       120
tacacagtgg ttttcttgac cggcatcctg ctgaatactt tggctctgtg ggtgtttgtt       180
cacatcccca gctcctccac cttcatcatc tacctcaaaa acactttggt ggccgacttg       240
ataatgacac tcatgcttcc tttcaaaatc ctctctgact cacacctggc accctggcag       300
ctcagagctt tgtgtgtcg tttttcttcg gtgatatttt atgagaccat gtatgtgggc        360
atcgtgctgt tagggctcat agcctttgac agattcctca agatcatcag acctttgaga       420
aatatttttc taaaaaaacc tgttttgca aaaacggtct caatcttcat ctggttcttt        480
ttgttcttca tctccctgcc aaatatgatc ttgagcaaca aggaagcaac accatcgtct       540 gtgaaaagt gtgcttcctt aaaggggcct ctggggctga atggcatca atggtaaat         600 aacatatgcc agtttatttt ctggactgtt tttatcctaa tgcttgtgtt ttatgtggtt       660
attgcaaaaa aagtatatga ttcttataga aagtccaaaa gtaaggacag aaaaaacaac       720
aaaaagctgg aaggcaaagt atttgttgtc gtggctgtct tctttgtgtg ttttgctcca      780
tttcattttg ccagagttcc atatactcac agtcaaacca acaataagac tgactgtaga       840
ctgcaaaatc aactgtttat tgctaaagaa acaactctct ttttggcagc aactaacatt       900
tgtatggatc ccttaatata catattctta tgtaaaaaat tcacagaaaa gctaccatgt       960
atgcaaggga gaaagaccac agcatcaagc caagaaaatc atagcagtca gacagacaac      1020
ataaccttag gctgacaact gtacataggg ttaacttcta tttattgatg agacttccgt      1080
agataatgtg gaaatcaaat ttaaccaaga aaaaagatt ggaacaaatg ctctcttaca      1140
ttttattatc ctggtgtaca gaaaagatta tataaaattt aaatccacat agatctattc     1200
ataagctgaa tgaaccatta ctaagagaat gcaacaggat acaaatggcc actagaggtc      1260
attatttctt tctttctttt tttttttttt aatttcaaga gcatttcact ttaacatttt      1320
ggaaaagact aaggagaaac gtatatccct acaaacctcc cctccaaaca ccttctcaca      1380
ttcttttcca caattcacat aacactactg cttttgtgcc ccttaaatgt agatatgtgc      1440
tgaaagaaaa aaaaacgcc caactcttga agtccattgc tgaaaactgc agccaggggt       1500
tgaaagggat gcagacttga agagtctgag gaactgaagt gggtcagcaa gacctctgaa      1560
atcctgggta aaggattttc tccttacaat tacaaacagc ctctttcaca ttacaataat      1620
ataccatagg aggcacaagc accattatta agccactttg cttacacctt aagtgtgtac      1680
aattcaagtg tgagaatgct gtgttaacta ttctttggaa ttctccttct gtccagcaaa      1740
tactctaatg atggttaaac atggcaccta ctcagcaatg ccttcctgga ccacaacccc      1800 tatcccctg ccccaccctc ctcattaaaa acaaatactt ctactgtttg ggtgtgtgat       1860
agggttctca atgcagatct ccctttttcta gttagctata ttcttgactg catccgctaa     1920
aaatgttaaa gcttcttgag agacagacat gccagatttt cttggtatct cccataatac      1980
gacctacagt ccatggtcta cagatgtttt aaatagaatt gctattctcg atacatacaa      2040
agacgtaatt gctgacccac aatcagtaac atccatattg ggagattttt caaaggatgg      2100
tgaccctgct tgtatttatt taccttggta ttttttcttg catccttctg tgattcaaaa      2160
aagtaaaatg tggctttctg aaatgatgga taagagtcta catcttctag aaaaaataca     2220
taaaggagta gttaagctct gtaaatgtgc cacgagctcc aacacgacca tcgtagggtg      2280
```

```
aagcccacgt tttcttccat ggcctcaaag gccctagaac ttgcctacct ttctggcctt    2340
acctcctagc tacttatcca tctcttgaac tttatactct tgtataaatt tctaactttc    2400
agaaaatgcc atactctgtt ttggcaccac acatgtatat ttcccctgg tacacttgga    2460 agactcttat ccatctgtga aaccctatgt tgtcatcact tggtccatga aatattacct    2520
ggccaatatc ccaccatcac ctcaaaccca atcaccccct cctctgtatg ctgtcacacc    2580
tatattatta aacttatcac attgcattgt aattacttcc tgacctttgt atctactctt    2640
ttagtaactg atgtatatat ctgaaaggag agattgtttc attgtgcaat cataaatgt    2700 ttgataaaat aaagccc                                                  2717

<210> SEQ ID NO 7
<211> LENGTH: 333
<212> TYPE: PRT
<213> ORGANISM: Homo sapiens

<400> SEQUENCE: 7

Met Asn Thr Thr Val Met Gln Gly Phe Asn Arg Ser Glu Arg Cys Pro
1               5                   10                  15

Arg Asp Thr Arg Ile Val Gln Leu Val Phe Pro Ala Leu Tyr Thr Val
            20                  25                  30

Val Phe Leu Thr Gly Ile Leu Leu Asn Thr Leu Ala Leu Trp Val Phe
        35                  40                  45

Val His Ile Pro Ser Ser Ser Thr Phe Ile Ile Tyr Leu Lys Asn Thr
    50                  55                  60

Leu Val Ala Asp Leu Ile Met Thr Leu Met Leu Pro Phe Lys Ile Leu
65                  70                  75                  80

Ser Asp Ser His Leu Ala Pro Trp Gln Leu Arg Ala Phe Val Cys Arg
                85                  90                  95

Phe Ser Ser Val Ile Phe Tyr Glu Thr Met Tyr Val Gly Ile Val Leu
            100                 105                 110

Leu Gly Leu Ile Ala Phe Asp Arg Phe Leu Lys Ile Ile Arg Pro Leu
        115                 120                 125

Arg Asn Ile Phe Leu Lys Lys Pro Val Phe Ala Lys Thr Val Ser Ile
    130                 135                 140

Phe Ile Trp Phe Phe Leu Phe Phe Ile Ser Leu Pro Asn Met Ile Leu
145                 150                 155                 160

Ser Asn Lys Glu Ala Thr Pro Ser Ser Val Lys Lys Cys Ala Ser Leu
                165                 170                 175

Lys Gly Pro Leu Gly Leu Lys Trp His Gln Met Val Asn Asn Ile Cys
            180                 185                 190

Gln Phe Ile Phe Trp Thr Val Phe Ile Leu Met Leu Val Phe Tyr Val
        195                 200                 205

Val Ile Ala Lys Lys Val Tyr Asp Ser Tyr Arg Lys Ser Lys Ser Lys
    210                 215                 220

Asp Arg Lys Asn Asn Lys Lys Leu Glu Gly Lys Val Phe Val Val Val
225                 230                 235                 240

Ala Val Phe Phe Val Cys Phe Ala Pro Phe His Phe Ala Arg Val Pro
                245                 250                 255

Tyr Thr His Ser Gln Thr Asn Asn Lys Thr Asp Cys Arg Leu Gln Asn
            260                 265                 270

Gln Leu Phe Ile Ala Lys Glu Thr Thr Leu Phe Leu Ala Ala Thr Asn
        275                 280                 285

Ile Cys Met Asp Pro Leu Ile Tyr Ile Phe Leu Cys Lys Lys Phe Thr
```

-continued

```
            290                 295                 300
Glu Lys Leu Pro Cys Met Gln Gly Arg Lys Thr Thr Ala Ser Ser Gln
305                 310                 315                 320

Glu Asn His Ser Ser Gln Thr Asp Asn Ile Thr Leu Gly
                325                 330
```

<210> SEQ ID NO 8
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 8
tatacatatg ttcagcagta ccaactc                                27

<210> SEQ ID NO 9
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 9
acaccagtgt atagatagca agaagtc                                27

<210> SEQ ID NO 10
<211> LENGTH: 36
<212> TYPE: DNA
<213> ORGANISM: Artificial Sequence
<220> FEATURE:
<223> OTHER INFORMATION: Oligonucleotide primer

<400> SEQUENCE: 10
cccgtcgaca tgctttcttt tatgacaaaa tccttg                      36

<210> SEQ ID NO 11
<211> LENGTH: 36
<212> TYPE: DNA
<213> ORGANISM: Artificial Sequence
<220> FEATURE:
<223> OTHER INFORMATION: Oligonucleotide primer

<400> SEQUENCE: 11
aaagcggccg cgaacagcag ctgtgtcatc cgagtg                      36

<210> SEQ ID NO 12
<211> LENGTH: 38
<212> TYPE: DNA
<213> ORGANISM: Artificial Sequence
<220> FEATURE:
<223> OTHER INFORMATION: Oligonucleotide primer

<400> SEQUENCE: 12
aaaggcgcgc caggcaagaa cagcaggatc aagcgaag                    38

<210> SEQ ID NO 13
<211> LENGTH: 35
<212> TYPE: DNA
<213> ORGANISM: Artificial Sequence
<220> FEATURE:
<223> OTHER INFORMATION: Oligonucleotide primer

<400> SEQUENCE: 13
aaacaattgt ggcttctgag gctatggaaa gagag                       35

<210> SEQ ID NO 14
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 14
atatggcaca tttggtccgc actgcac                                      27

<210> SEQ ID NO 15
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 15
gatgaggaat gatgtcacac agatgag                                      27

<210> SEQ ID NO 16
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 16
aaggtcaaga ttagcaagtg attccag                                      27

<210> SEQ ID NO 17
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 17
ataccataca cttacagtca aaccacc                                      27

<210> SEQ ID NO 18
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 18
ggtcttcgct tgatcctgct gttcttg                                      27

<210> SEQ ID NO 19
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 19
ttggctaccc gtgatattgc tgaagag                                      27

<210> SEQ ID NO 20
<211> LENGTH: 27
<212> TYPE: DNA
<213> ORGANISM: Artificial Sequence
<220> FEATURE:

-continued

<223> OTHER INFORMATION: Oligonucleotide primer

<400> SEQUENCE: 20
gtcgtgaccc atggcgatgc ctgcttg                                27

<210> SEQ ID NO 21
<211> LENGTH: 13800
<212> TYPE: DNA
<213> ORGANISM: Artificial Sequence
<220> FEATURE:
<223> OTHER INFORMATION: Knockout plasmid construct

<400> SEQUENCE: 21

```
ttacaaatat gttaaaacaa acatacaaga gaacctgaat acatatgttc agcagtaaca    60
actcaaaaag tcaaacaaat taaatgtcca tccgtaacag aatgtttata caattttgtt   120
tgtatgttct cttggactta tgtatacaag tcgtcattgt tgagttttc  agtttgttta   180
atttacaggt aggcattgtc cttaaccaaa atatgggaaa agttgtgttt atcattatga   240
tcagtgtcta tgtattaaca tagactaaga caaaaattaa cacagactaa aataagcatg   300
gaattggttt tatacccttt tcaacacaaa tagtaatact agtcacagat acataattgt   360
atctgattct gttttttaatt gtgtctgatt ttattcgtac aacacttaca cactagtata   420
aatataaatg acttcttgct atctatacac tggtgtttag agttttcaaa tagttgtttt   480
gtgtgtgtgt atgttttgtg ttgtgaatgt gtgatcatat ttatatttac tgaagaacga   540
tagatatgtg accacaaatc tcaaaagttt atcaacaaaa cacacacaca tacaaaacac   600
tgtgtgtgtg tgtgtgtgtg tgtatgtgtg tgtgtgtgca tgtcccctttg tgagtgtggg   660
cctgtgtaca ctatcacaca catataggtg tcaaaggaca acacacacac acacacacac   720
acatacacac acacacacgt acaggggaac actcacaccc ggacacatgt gatagtgtgt   780
gtatatccac agtttcctgt acctcaggtg tcagacatca tttgtcattt tgtttgagat   840
agagtctcct tttttactgct gcatatacca gaccaaccac tctgcatgct tctaaggaat   900
tggagtccac agtctgtagt aaacagtaaa acaaactcta tctcagagga aaaatgacga   960
cgtatatggt ctggttggtg agacgtacga agattcctta tctgtttcca tatccccaat  1020
ctcgcaatac gaatgacaga attacatata cacattactg tgtctacttc tatatgggct  1080
caggagatct aagtttattc agacaaaggt ataggggtta gagcgttatg cttactgtct  1140
taatgtatat gtgtaatgac acagatgaag atataccga  gtcctctaga ttcaaataag  1200
ttccatgctt gtgtggcaag tgcttttacct actgcgtcat ctcctatgta tttcatcttt  1260
aaaacatatg ctttcttta  tgacaaaatc cttgtaacta aggtacgaa  cacaccgttc  1320
acgaaatgga tgacgcagta gaggatacat aaagtagaaa ttttgtatac gaaagaaaat  1380
actgttttag gaacattgat aatattaagc atttcaagta ttgctgtgaa tatattgcct  1440
gtttctgaag agattttttct aatactgatt ttcacttcag acatctgct  tgtaaactac  1500
ttataattcg taaagttcat aacgacactt ataacggaa  caaagacttc tctaaaaga  1560
ttatgactaa aagtgaagtc ctgtagacga acatttgatg atagtgtatt taactcatta  1620
tcacttttgg ttaccctaat tggaaagttt taaaaaattc acatgctcta aggaaagtac  1680
ctcagtagat ttcagagtaa tatcacataa attgagtaat agtgaaaacc aatgggatta  1740
acctttcaaa attttttaag tgtacgagat tcctttcatg gagtcatcta aagtctcatt  1800
ataagagttc tctcctagga atatttgagt tcccacttca acttacatcc ttagtgaaaa  1860
tgaaagcaaa catctcaaca tttctaatgt tattatatga tattctcaag agaggatcct  1920
```

```
tataaactca agggtgaagt tgaatgtagg aatcactttt actttcgttt gtagagttgt    1980
aaagattaca ataatatact tgcatgttaa ctacatcacc agaagtccct tgctctttg     2040
ccttgatcca gctcaggaat cctggaggtc tagcaaagga agtaggtgta ggcaacttcc    2100
acgtacaatt gatgtagtgg tcttcaggga aacgagaaac ggaactaggt cgagtcctta    2160
ggacctccag atcgtttcct tcatccacat ccgttgaagg attacagacc agtttgtccc    2220
atctgaccat actggttgga caatttacaa atttaacctt agacctgagt gtgtaccaga    2280
cagaactgag tgtccgttca taatgtctgg tcaaacaggg tagactggta tgaccaacct    2340
gttaaatgtt taaattggaa tctggactca cacatggtct gtcttgactc acaggcaagt    2400
gcttcttttt cctgtatcaa tcattgactc ttggcataag gacttcagga tgaagtgaac    2460
cactccagct gctctctcag gggtgtggtg gggttgggac cgaagaaaaa ggacatagtt    2520
agtaactgag aaccgtattc ctgaagtcct acttcacttg gtgaggtcga cgagagagtc    2580
cccacaccac cccaaccctg aaggcaggct ctaagtgcaa attctagggc ccagtggtaa    2640
gttagtggtg gtctctatta ccactatttt gggaaggtgc ttaatttctt cattttgatt    2700
ttccgtccga gattcacgtt taagatcccg ggtcaccatt caatcaccac cagagataat    2760
ggtgataaaa cccttccacg aattaaagaa gtaaaactaa ttcacatcta aaataagact    2820
ggactatgtt gttattgtaa gggctgtgat aacatagtta cctataatac catagctatt    2880
tttattttat tactttgagt aagtgtagat tttattctga cctgatacaa caataacatt    2940
cccgacacta ttgtatcaat ggatattatg gtatcgataa aaataaaata atgaaactca    3000
ctattcttag tgcataaaag aattccagtc tttaatttat tccagtcttt aaattattca    3060
gcaggctcct aaacactgaa acttttcaat gcatggggtt gataagaatc acgtattttc    3120
ttaaggtcag aaattaaata aggtcagaaa tttaataagt cgtccgagga tttgtgactt    3180
tgaaaagtta cgtaccccaa ttttttgtttg tttgtttgtt tgtttgtttt tgtttgttttt   3240
ttgtttttta gttcttcctt cccggccttc gtgaactaat aagcccacag tattcctatt    3300
aaaaacaaac aaacaaacaa acaaacaaaa acaaacaaaa aacaaaaaat caagaaggaa    3360
gggccggaag cacttgatta ttcgggtgtc ataaggataa ttcttttttca ttgactgagg   3420
aagctcgcat gacatcgtcc atgacaggcc tcactgtgag catatgatgg acgttctttt    3480
acccctaact atatgaaaag aagaaaaagt aactgactcc ttcgagcgta ctgtagcagg    3540
tactgtccgg agtgacactc gtatactacc tgcaagaaaa tggggattga tatacttttc    3600
gacactgttg tgtatttcat cataaaaagg gggcaagtat ttcagagtga gtataaataa    3660
cttcccaaat gagggaaaca aaaagcgaca ggtggacaag ctgtgacaac acataaagta    3720
gtattttttcc cccgttcata aagtctcact catatttatt gaagggttta ctccccttgt   3780
ttttcgctgt ccacctgttc cccttggagc tacggcccgc agcttggaga tggcacttcc    3840
acacaggcct agggagcagc gtgcagagag gcccttccaa gaggaacagg ctttccaaca    3900
gggaacctcg atgccgggcg tcgaacctct accgtgaagg tgtgtccgga tccctcgtcg    3960
cacgtctctc cgggaaggtt ctccttgtcc gaaaggttgt aatatcagct aaggaactta    4020
ccaaggggag ctctcattta acaagtgtgt agtagttatg aagatgactc agctagagaa    4080
gaccaaccat gaccatgcag ttatagtcga ttccttgaat ggttcccctc gagagtaaat    4140
tgttcacaca tcatcaatac ttctactgag tcgatctctt ctggttggta ctggtacgtc    4200
agctcaatcc atgaaaccca catgttggaa agatataact aacccactga aggaaaacac    4260
```

```
acacacacat acacacacac tcacacactc acaataaata tcgagttagg tactttgggt    4320
gtacaacctt tctatattga ttgggtgact tccttttgtg tgtgtgtgta tgtgtgtgtg    4380
agtgtgtgag tgttatttat tgtatttcac aaccaaaaga atgtaccttt gtgaccctag    4440
aaatgtccat tgctgatcag ttcctctttt caaagtttcc cacatttggc attttgaaat    4500
acataaagtg ttggttttct tacatggaaa cactgggatc tttacaggta acgactagtc    4560
aaggagaaaa gtttcaaagg gtgtaaaccg taaaacttta ttgaccaaaa tgtgatttct    4620
acttctcata ttatgaaatt atcctgtaca gaatttccct tgtttaaagt aaaaatttcc    4680
agaccttcaa tgttatattg aactggtttt acactaaaga tgaagagtat aatactttaa    4740
taggacatgt cttaaaggga acaaatttca ttttttaaagg tctggaagtt acaatataac    4800
gattgggggc tattgagaaa tttaaaattg actgtgttta tggttaaaat taacaataaa    4860
cctactttaa aatattgatt ttgctaggtt tttatcctct ctaaccccccg ataactcttt    4920 aaattttaac tgacacaaat accaatttta attgttattt ggatgaaatt ttataactaa    4980
aacgatccaa aaataggaga tataaagcaa aaggatatat atttaagtta aggggcatta    5040
catcagtaaa tcctaacata ttttagccaa aaagaaaatt tttacaatgt gccatttatt    5100
atatttcgtt ttcctatata taaattcaat tccccgtaat gtagtcattt aggattgtat    5160
aaaatcggtt tttcttttaa aaatgttaca cggtaaataa ccctagagtt aaccaacgtt    5220
ccctggaaac acagtacatt tcattttaaa atgttcaaat gtggaatcaa tggattccaa    5280
attctcaacc aagtaatata gggatctcaa ttggttgcaa gggacctttg tgtcatgtaa    5340
agtaaaattt tacaagttta caccttagtt acctaaggtt taagagttgg ttcattatat    5400
ggaattacta gttagccaaa ccctgaagac ggtccatctc tacggtaagc gcgtggcaag    5460
aacggtgaag tgaaacttgc catagagaac cacacatcct ccttaatgat caatcggttt    5520
gggacttctg ccaggtagag atgccattcg cgcaccgttc ttgccacttc actttgaacg    5580
gtatctcttg gtgtgtagga ccccaggatc atctgatttc ctctttccct tcatctgtcg    5640
ggcagggaag cagactgtca cacattgtaa ctttctgcac actccctgag atttaaaacg    5700
ggggtcctag tagactaaag gagaaaggga agtagacagc ccgtcccttc gtctgacagt    5760
gtgtaacatt gaaagacgtg tgagggactc taaattttgc aaaacactgta ccaatctgag    5820 gccagccctg attcaaaact tctctaagtc tcaagaatgg aggtggtttc ccaaaagggc    5880
ttcctaaaag tgccacactg tttgtgacat ggttagactc cggtcgggac taagttttga    5940
agagattcag agttcttacc tccaccaaag ggttttcccg aaggattttc acggtgtgac    6000
tagctccact caaactgggc aattcaagga acccaagcaa tgagcggctg gcatgtttag    6060 cttttcactga tgtgccctgg gtcggtccat cggtccccct atcgaggtga gtttgacccg    6120
ttaagttcct tgggttcgtt actcgccgac cgtacaaatc gaaagtgact acacgggacc    6180
cagccaggta gccaggggga ccccacacact cctatgaagt agatgatgat ttcaaacttg    6240
ctacatgaga gaatgaggta tatagctctt aaaacatttg tttaaacata ataccgaata    6300
gggggtgtga ggatacttca tctactacta aagtttgaac gatgtactct cttactccat    6360
atatcgagaa ttttgtaaac aaatttgtat tatggcttat atgcagaggt ccaggaataa    6420
tagctaccac ttcttgggaa atgtgactca taatctgcca cagatctagg gatcaaaaga    6480
ctaacagcaa tgtctgaaga tacgtctcca ggtccttatt atcgatggtg aagaacccatt    6540 tacactgagt attagacggt gtctagatcc ctagttttct gattgtcgtt acagacttct    6600
aaggaaacaa agcaaaacaa acaagcaacc aacaaccaaa gcctagcctt agacatacaa    6660
```

```
acttcttgca cgcccaggct gtaagggaca gaagatgatt ttcctttgtt tcgttttgtt    6720
tgttcgttgg ttgttggttt cggatcggaa tctgtatgtt tgaagaacgt gcgggtccga    6780
cattccctgt cttctactaa tgattttcag atcaagtctt ctcctcctac ttgattgtaa    6840
tttcatacta ttttcttcat cattttaact cctactatta catatgaagt attcaataag    6900
actaaaagtc tagttcagaa gaggaggatg aactaacatt aaagtatgat aaagaagta    6960 gtaaaattga ggatgataat gtatacttca taagttattc gtcgctgaat gtgaataata    7020
aaaagtaaaa cactgggcct agagaaatag ttcggcggtt aaagggattt tcctggcacc    7080
cactccaggc agctcacagt cagcgactta cacttattat ttttcatttt gtgacccgga    7140
tctctttatc aagccgccaa tttccctaaa aggaccgtgg gtgaggtccg tcgagtgtca    7200
caccttggac cccagctcca gggaatccaa cacttctggc ctctgagggc acctgaatgc    7260
atatgcgccc ttacacatat aatttaatat aataaaatag gtggaacctg ggtcgaggt    7320 cccttaggtt gtgaagaccg gagactcccg tggacttacg tatacgcggg aatgtgtata    7380
ttaaattata ttatttatc accacatgtt aagaatatgg cgtggtggcg tgcctgcaga    7440
gccggtgaca gcactggatt caatactcag aacacgcaac caataactac tggtaaatgc    7500
tggtgtacaa ttcttatacc gcaccaccgc acggacgtct cggccactgt cgtgacctaa    7560
gttatgagtc ttgtgcgttg ttattgatg accatttacg tccaaaggtc taaagacaaa    7620
gaggttctag aaaatgtggg tattacagaa gcccacaagg ggaaatgagg aaggaaaagc    7680
agtataagaa agcagaacct aggtttccag atttctgttt ctccaagatc ttttacaccc    7740
ataatgtctt cgggtgttcc cctttactcc ttcctttcg tcatattctt cgtcttgga    7800 ttacttcaca agctattcgt gggttgagct agtaactgcc acaactcata cagctgagtc    7860
tcttccaaaa caaggtcag tttaattttt cttatgaatt aatgaagtgt tcgataagca    7920
cccaactcga tcattgacgg tgttgagtat gtcgactcag agaaggtttt gtttccagtc    7980
aaattaaaaa gaatacttaa tgcttgctat aaaaggtaaa aggtggttaa attttctaga    8040
aatctaaata taatattctg taatcacggg ctgcaagcat aaggtacttc ataacgcatg    8100
acgaacgata ttttccattt tccaccaatt taaaagatct ttagatttat attataagac    8160
attagtgccc gacgttcgta ttccatgaag tattgcgtac acacactacc ctgtactctt    8220
acatcttaaa ttaggttctg tcaccgccgt gtagtgattg gtgcttgcta tttggacttc    8280
acaagggtag acattaacag tgtgtgatgg gacatgagaa tgtagaattt aatccaagac    8340
agtggcggca catcactaac cacgaacgat aaacctgaag tgttcccatc tgtaattgtc    8400
gactttataa aacaaaacta aactgaacaa aaaccaacca aacaacaaca gcaacaaaac    8460
taagctatgt gctcaaaaaa gctctagcca aagaatcaaa ctgaaatatt ttgttttgat    8520
ttgacttgtt tttggttggt ttgttgttgt cgttgttttg attcgataca cgagtttttt    8580
cgagatcggt ttcttagttt tccgctgaat gagttaaata gtaagtttgt ttttacaaga    8640
agtagttatc tgccaatcca caaggaccct ttgtttacct tcctttgtat gcctgcttat    8700
aggcgactta ctcaatttat cattcaaaca aaatgttct tcatcaatag acggttaggt    8760
gttcctggga aacaaatgga aggaaacata cggacgaata gtgtaatctt tctctgtgtg    8820
catgtttatg tgtaatagct gatgctcggg acaatcaaca ccactgggat gcagggcttc    8880
aacaagtctg agcggtgccc cacattagaa agagacacac gtacaaatac acattatcga    8940
ctacgagccc tgttagttgt ggtgacccta cgtcccgaag ttgttcagac tcgccacggg    9000
```

```
cagggacact cggatgacac agctgctgtt cccggttctc tatactgtgg tcttcctggc    9060
aggcatcctg ctgaacaccg tggccctctg ggtgttcgtc gtccctgtga gcctactgtg    9120
tcgacgacaa gggccaagag atatgacacc agaaggaccg tccgtaggac gacttgtggc    9180
accgggagac ccacaagcag cacatcccca gcaattccac ctttatcgtc tacctcaaga    9240
acactctggt ggcagacttg ataatggcac tcatgctgcc tttcaaaatc ctttccgact    9300
gtgtaggggt cgttaaggtg gaaatagcag atggagttct tgtgagacca ccgtctgaac    9360
tattaccgtg agtacgacgg aaagttttag gaaaggctga cacaccttgc gccctggcag    9420
ctccgaggat ttgtgtgcac gctctcctcc gtggtcttct atgagacgat gtatgtgggt    9480
atcatgatgc tgggcctcat gtgtggaacg cgggaccgtc gaggctccta acacacgtg     9540 cgagaggagg caccagaaga tactctgcta catacaccca tagtactacg acccggagta    9600
cgctttcgac aggttcctca agatcatcat gccgttcagg aaaacctttg tcaaaaagac    9660
ggctttcgca aaaacagtct ccatttccgt ctggtccctg cgaaagctg tccaaggagt     9720 tctagtagta cggcaagtcc ttttggaaac agttttttctg ccgaaagcgt ttttgtcaga   9780
ggtaaaggca gaccagggac atgttcttca tctcccctgcc aaacatgatc ttgaacaagg   9840
aggcaacgcc atcatccgtg aagaagtgtg catctttgaa gagtccccctt gggctgtggt   9900 tacaagaagt agagggacgg tttgtactag aacttgttcc tccgttgcgg tagtaggcac    9960
ttcttcacac gtagaaactt ctcagggaa cccgacacca ggcatcaggt ggtcagtcac     10020
acctgccagt tcattttctg ggctgtgttt attctgatgc ttctgtttta tgcggtgatt    10080
accaaaaagg tgtacaactc ccgtagtcca ccagtcagtg tggacggtca agtaaaagac    10140
ccgacacaaa taagactacg aagacaaaat acgccactaa tggttttttcc acatgttgag   10200 ctataggaag tttaggagta aggacagcag gcacaagcgg ctggaggtga aggtatttat    10260
cgtcatggct gtcttctttg tctgcttttgc cccactgcat gatatccttc aaatcctcat   10320
tcctgtcgtc cgtgttcgcc gacctccact tccataaata gcagtaccga cagaagaaac    10380
agacgaaacg gggtgacgta tttgtcagaa taccatacac ttacagtcaa accaccaata    10440
agactgactg taggttagaa aaccagctgt ttattgctaa agaagcaact ctctttctgg    10500
aaacagtctt atggtatgtg aatgtcagtt tggtggttat tctgactgac atccaatctt    10560
ttggtcgaca ataacgatt tcttcgttga gagaaagacc caacaactaa catttgtatg     10620
gaccccttaa tatacataat tttatgcaag aagttcacac aaaaggtgcc atgtgtgaga    10680
tggggaaagg caagaacagc gttgttgatt gtaaacatac ctggggaatt atatgtatta    10740
aaatacgttc ttcaagtgtg ttttccacgg tacacactct acccctttcc gttcttgtcg    10800
aggatcaagc gaagaccacc acagtagtca gacagacaac atcaccctag cctgaccact    10860
gtgtcccaca ggttaatttc acgcatggcc tcacgtctat tcctagttcg cttctggtgg    10920
tgtcatcagt ctgtctgttg tagtgggatc ggactggtga cacagggtgt ccaattaaag    10980
tgcgtaccgg agtgcagata ttatggatgg gatttcaaaa gatcatttat gtggagacct    11040
catttaagca ttacaggaaa aaagagggga acaaacagtt ccctacattt tattatccta    11100
aatacctacc ctaaagtttt ctagtaaata cacctctgga gtaaattcgt aatgtccttt    11160
tttctcccct tgtttgtcaa gggatgtaaa ataataggat gtgtatggaa aaacattatg    11220 cccatttttaa ccacatagac gtatttataa gcaggataaa ttaagagacc atgtaataca    11280
```

```
gcaaatggcc actagatgtc cacataccTt tttgtaatac gggtaaaatt ggtgtatctg   11340
cataaatatt cgtcctattt aattctctgg tacattatgt cgtttaccgg tgatctacag   11400
accttttcaa gggcattcat gtactatgga aaaggttaat gggaaacagg tttgcctgaa   11460
aaatcttcct tctagttacc accccaccat ctcttcacac tggaaaagtt cccgtaagta   11520
catgatacct tttccaatta ccctttgtcc aaacggactt tttagaagga agatcaatgg   11580
tggggtggta gagaagtgtg atatattccc taaaacacca ggctggcttt tacagccttc   11640
agaatgctga cacttgtgaa cagaaaccaa ccaacttgca tatccagtgc ctgtgtggaa   11700
tatataaggg attttgtggt ccgaccgaaa atgtcggaag tcttacgact gtgaacactt   11760
gtctttggtt ggttgaacgt ataggtcacg dacacaccTt aggctaaggt ggggctcaa    11820 agagatgcag tctgaggaac caaagtgggt tggtcaaaat aaccccaggc atctcaaaag   11880
atttcctcct tacaagtgca tccgattcca ccccgagtt tctctacgtc agactccttg    11940
gtttcaccca accagtttta ttggggtccg tagagttttc taaaggagga atgttcacgt   12000
aagggctgct cctacatcta aacagagcac cagaagagag gcacatgcaa caggcaaagc   12060
cagttcacag ccatgtgcaa tccagagagg ggaagtgttt ttcccgacga ggatgtgat    12120 ttgtctcgtg gtcttctctc cgtgtacgtt gtccgtttcg gtcaagtgtc ggtacacgtt   12180
aggtctctcc ccttcacaaa agtcagcaaa accttcctgg gcaacagcat ctgcatcctg   12240
ttggaaaata cttatttccc tcactgttta tctataaatt aggttccttg ctacacactg   12300
tcagtcgttt tggaaggacc cgttgtcgta dacgtaggac aaccttttat gaataaaggg    12360
agtgacaaat agatatttaa tccaaggaac gatgtgtgac tcttatatta actgctttca   12420
ttcttagcca catttcccaa aaacagggtt cgtaaaaaga cagcaaaatc acacatttt    12480 acaaaagaaa tgggtaagg agaatataat tgacgaaagt aagaatcggt gtaagggtt     12540 tttgtcccaa gcatttttct gtcgttttag tgtgtaaaaa tgttttcttt accccattcc   12600
atatcctaga cgggatgttt gttgtacact atccttagtg catgtgagca agggatggt    12660 tggcctggca ttagtaatat tcatgtggga agatttttca tataggatct gcccctacaaa   12720 caacatgtga taggaatcac gtacactcgt tcccctacca accggaccgt aatcattata   12780
agtacaccct tctaaaagt aagcctgatt catttatt gggcctatct actttcctgg      12840
atctcattat gggtttaaga aaattaaaat atgtggctgg tgatgctggg ttttctggag    12900
ttcggactaa gtaaataaa cccggataga tgaagggacc tagagtaata cccaaattct    12960
tttaatttta tacaccgacc actacgaccc aaaagacctc aacacgacga ctcttcccct   13020
aaccgcgcct gtaatgtgaa atcctggctt ctctctttcc atagcctcag aagccacaga   13080
ggcaagagaa cttccttgtc ttgtgctgct gagaagggga ttggcgcgga cattacactt   13140
taggaccgaa gagagaaagg tatcggagtc ttcggtgtct ccgttctctt gaaggaacag   13200
ttcctggaat cacttgctaa tcttgacctt tacaaactcc atttaatatg gcacatttgg    13260
tccgcactgc actgtacata gaaccttcca tctgacccac aaggacctta gtgaacgatt   13320
agaactggaa atgtttgagg taaattatac cgtgtaaacc aggcgtgacg tgacatgtat   13380
cttggaaggt agactgggtg tttgtaagtt cctattgatt agtgacaccc aaagttgctg   13440
tcccttactc caggtaacct tacctgccca acctcctccg agtcctccag cccagtcact   13500
aaacattcaa ggataactaa tcactgtggg tttcaacgac agggaatgag gtccattgga   13560
```

```
atggacgggt tggaggaggc tcaggaggtc gggtcagtga tcctcatctg tgtgacatca  13620
ttcctcatct acttatcgaa ttgatttagg ataatttgct aaatatgcac tgtgcaatta  13680
ataaattttg ctaaaacaaa aggagtagac acactgtagt aaggagtaga tgaatagctt  13740
aactaaatcc tattaaacga tttatacgtg acacgttaat tatttaaaac gattttgttt  13800
```

USE OF THE RECEPTOR GPR86

CROSS-REFERENCE TO RELATED APPLICATIONS

This application is a continuation-in-part of International Application number PCT/GB2005/002601, filed Jul. 1, 2005, published as WO 2006/003422 on Jan. 12, 2006, and claiming priority to GB Application Nos. 0414798.9, filed Jul. 1, 2004, and 0510253.8, filed May 19, 2005, and to U.S. Application Nos. 60/586,513 filed Jul. 9, 2004 and 60/683,471 filed May 20, 2005.

The foregoing applications, and each document cited or referenced in each of the present and foregoing applications, including during the prosecution of each of the foregoing applications ("application and article cited documents"), and any manufacturer's instructions or catalogues for any products cited or mentioned in each of the foregoing applications and articles and in any of the application and article cited documents, are hereby incorporated herein by reference. Furthermore, all documents cited in this text, and all documents cited or reference in documents cited in this text, and any manufacturer's instructions or catalogues for any products cited or mentioned in this text or in any document hereby incorporated into this text, are hereby incorporated herein by reference. Documents incorporated by reference into this text or any teachings therein may be used in the practice of this invention. Documents incorporated by reference into this text are not admitted to be prior art.

FIELD OF THE INVENTION

This invention relates to newly identified functions of nucleic acids, polypeptides encoded by them and to their production and use. More particularly, the nucleic acids and polypeptides relate to a G-protein coupled receptor (GPCR), hereinafter referred to as "GPR86", and members of the purinoceptor family of GPCRs. The invention also relates to inhibiting or activating the action of such nucleic acids and polypeptides.

BACKGROUND OF THE INVENTION

It is well established that many medically significant biological processes are mediated by proteins participating in signal transduction pathways that involve G-proteins and/or second messengers, for example, cAMP (Lefkowitz, *Nature*, 1991, 351: 353-354). These proteins are referred to as proteins participating in pathways with G-proteins or "PPG proteins". Some examples of these proteins include the GPC receptors, such as those for adrenergic agents and dopamine (Kobilka, B. K., et al., *Proc. Natl. Acad. Sci., USA*, 1987, 84: 46-50; Kobilka B. K., et al., *Science*, 1987, 238: 650-656; Bunzow, J. R., et al., *Nature*, 1988, 336: 783-787), G-proteins themselves, effector proteins, for example, phospholipase C, adenyl cyclase, and phosphodiesterase, and actuator proteins, for example, protein kinase A and protein kinase C (Simon, M. I., et al., *Science*, 1991, 252: 802-8).

For example, in one form of signal transduction, the effect of hormone binding is activation of the enzyme adenylate cyclase inside the cell. Enzyme activation by hormones is dependent on the presence of the nucleotide, GTP. GTP also influences hormone binding. A G-protein connects the hormone, receptor to adenylate cyclase. G-protein is shown to exchange GTP for bound GDP when activated by a hormone receptor. The GTP carrying form then binds to activated adenylate cyclase. Hydrolysis of GTP to GDP, catalysed by the G-protein itself, returns the G-protein to its basal, inactive form. Thus, the G-protein serves a dual role, as an intermediate that relays the signal from receptor to effector, and as a clock that controls the duration of the signal.

The membrane protein gene superfamily of G-protein coupled receptors (GPCRs) has been characterised as having seven putative transmembrane domains. The domains are believed to represent transmembrane α-helices connected by extracellular or cytoplasmic loops. G-protein coupled receptors include a wide range of biologically active receptors, such as hormone, viral, growth factor and neuroreceptors.

G-protein coupled receptors (also known as 7TM receptors) have been characterised as including these seven conserved hydrophobic stretches of about 20 to 30 amino acids, connecting at least eight divergent hydrophilic loops. The G-protein family of coupled receptors includes dopamine receptors which bind neuroleptic drugs used for treating psychotic and neurological disorders. Other examples of members of this family include, but are not limited to, calcitonin, adrenergic, endothelin, adenosine, muscarinic, serotonin, histamine, thrombin, kinin, follicle stimulating hormone, opsins, endothelial differentiation gene-1, rhodopsins, odorant, and cytomegalovirus receptors.

Most G-protein coupled receptors have single conserved cysteine residues in each of the first two extracellular loops which form disulphide bonds that are believed to stabilise functional protein structure. The 7 transmembrane regions are designated as TM1, TM2, TM3, TM4, TM5, TM6, and TM7. TM3 has been implicated in signal transduction.

Phosphorylation and lipidation (pamitylation or farnesylation) of cysteine residues can influence signal transduction of some G-protein coupled receptors. Most G-protein coupled receptors contain potential phosphorylation sites within the third cytoplasmic loop and/or the carboxy terminus. For several G-protein coupled receptors, such as the β-adrenoreceptor, phosphorylation by protein kinase A and/or specific receptor kinases mediates receptor desensitization. For some receptors, the ligand binding sites of G-protein coupled receptors are believed to comprise hydrophilic sockets formed by several G-protein coupled receptor transmembrane domains, the sockets being surrounded by hydrophobic residues of the G-protein coupled receptors. The hydrophilic side of each G-protein coupled receptor transmembrane helix is thought to face inward and form a polar ligand binding site. TM3 has been implicated in several G-protein coupled receptors as having a ligand binding site, such as the TM3 aspartate residue. TM5 serines, a TM6 asparagine and TM6 or TM7 phenylalanines or tyrosines are also implicated in ligand binding.

G-protein coupled receptors can be intracellularly coupled by heterotrimeric G-proteins to various intracellular enzymes, ion channels and transporters (see, Johnson et al., *Endoc. Rev.*, 1989, 10: 317-331). Different G-protein α-subunits preferentially stimulate particular effectors to modulate various biological functions in a cell. Phosphorylation of cytoplasmic residues of G-protein coupled receptors has been identified as an important mechanism for the regulation of G-protein coupling of some G-protein coupled receptors. G-protein coupled receptors are found in numerous sites within a mammalian host. Over the past 15 years, nearly 350 therapeutic agents targeting 7 transmembrane (7 TM) receptors have been successfully introduced onto the market.

Thus, G-protein coupled receptors have an established, proven history as therapeutic targets. Clearly there is a need for identification and characterization of further receptors which can play a role in preventing, ameliorating or correcting dysfunctions or diseases.

SUMMARY OF THE INVENTION

According to a first aspect of the present invention, we provide a method of identifying a molecule suitable for the treatment, prophylaxis or alleviation of a GPR86 associated disease, in particular inflammatory disease or pain, the method comprising determining whether a candidate molecule is an agonist or antagonist of GPR86 polypeptide, in which the GPR86 polypeptide comprises the amino acid sequence shown in SEQ ID NO: 3 or SEQ ID NO: 5 or SEQ ID NO: 7, a fragment thereof or a sequence which is at least 90% identical thereto.

Preferably, the GPR86 polypeptide is encoded by a nucleic acid sequence shown in SEQ ID NO: 1, SEQ ID NO: 2 or SEQ ID NO: 4, or a sequence which is at least 90% identical thereto.

Preferably, the method comprises exposing the candidate molecule to a GPR86 polypeptide, and determining whether the candidate molecule binds to GPR86 polypeptide.

Preferably, an agonist is identified by contacting a cell comprising GPR86 receptor coupled with the GPR86 favoured G-protein $G_i$ with a candidate compound and determining whether the level of a GPCR sensitive marker such as cyclic AMP (cAMP) in said cell is lowered as a result of said contacting.

Preferably, an antagonist is identified by contacting a cell comprising GPR86 receptor coupled with the GPR86 favoured G-protein $G_i$ with a candidate compound and determining whether the level of a GPCR sensitive marker such as cyclic AMP (cAMP) in said cell is raised as a result of said contacting.

Preferably, an agonist is identified by contacting a cell comprising GPR86 receptor coupled with a promiscuous stimulatory G-protein such as $G_{\alpha 16}$ with a candidate compound and determining whether the level of a GPCR sensitive marker such as cyclic AMP (cAMP) in said cell is raised as a result of said contacting.

Preferably, an antagonist is identified by contacting a cell comprising GPR86 receptor coupled with a promiscuous stimulatory G-protein such as $G_{\alpha 16}$ with a candidate compound and determining whether the level of a GPCR sensitive marker such as cyclic AMP (cAMP) in said cell is lowered as a result of said contacting.

Preferably, the method comprises (a) providing a wild type animal or a transgenic non-human animal having a functionally disrupted endogenous GPR86 gene; (b) exposing the wild type or transgenic non-human animal to a candidate molecule; and (c) determining whether a biological parameter of the animal is changed as a result of the contacting.

Preferably, the biological parameter is selected from the group consisting of: response to stimuli, response to heat, response to light, an immune response, an inflammatory response, response to pain, preferably response to pain.

Preferably, the method comprises: (a) providing a wild type cell or a cell comprising a functionally disrupted endogenous GPR86 gene, preferably a cell isolated from a transgenic non-human animal having a functionally disrupted endogenous GPR86 gene; (b) exposing the cell to a candidate molecule; and (c) determining whether a biological activity of GPR86 polypeptide is changed as a result of the contacting.

There is provided, according to a second aspect of the present invention, use of a wild type or transgenic non-human animal having a functionally disrupted endogenous GPR86 gene in a method of identifying an agonist or antagonist of GPR86 polypeptide for use in the treatment, prophylaxis or alleviation of a GPR86 associated disease, in particular inflammatory disease or pain.

Use of a transgenic non-human animal having a functionally disrupted endogenous GPR86 gene, or an isolated cell or tissue thereof, as a model for a GPR86 associated disease, in particular inflammatory disease or pain.

Preferably, the transgenic non-human animal comprises a functionally disrupted GPR86 gene, preferably comprising a deletion in a GPR86 gene or a portion thereof. Preferably, the transgenic non-human animal displays a change in any one or more of the following phenotypes when compared with a wild type animal: response to stimuli, response to heat, response to light, an immune response, an inflammatory response, response to pain, preferably response to pain.

Preferably, the transgenic non-human animal displays at least one of the following:
(a) an altered susceptibility to pain being an increased or decreased sensitivity to pain, and
(b) an altered susceptibility to inflammatory pain being an increased or decreased susceptibility to inflammatory pain, when compared to a wild-type animal.

Preferably, the transgenic non-human animal is a rodent, preferably a mouse.

We provide, according to a third aspect of the present invention, a method of identifying an agonist or antagonist of a GPR86 polypeptide, the method comprising administering a candidate compound to a wild type or transgenic non-human animal as described and measuring a change in a biological parameter.

As a fourth aspect of the present invention, there is provided use of a GPR86 polypeptide comprising an amino acid sequence shown in SEQ ID NO: 3 or SEQ ID NO: 5 or SEQ ID NO: 7, a fragment thereof or a sequence which is at least 90% identical thereto, for the identification of an agonist or antagonist thereof for the treatment, prophylaxis of a GPR86 associated disease, in particular inflammatory disease or pain.

We provide, according to a fifth aspect of the present invention, use of a GPR86 polynucleotide comprising a nucleic acid sequence shown in SEQ ID NO: 1, SEQ ID NO: 2 or SEQ ID NO: 4, a fragment thereof or a sequence which is at least 90% identical thereto, for the identification of an agonist or antagonist thereof for the treatment, prophylaxis of a GPR86 associated disease, in particular inflammatory disease or pain.

Preferably, the pain is selected from the group consisting of acute pain, chronic pain, cutaneous pain, somatic pain, visceral pain, referred pain, including myocardial ischaemia, phantom pain and neuropathic pain (neuralgia), pain arising from injuries, diseases, headaches, migraines, cancer pain, pain arising from neurological disorders such as Parkinson's disease, pain arising from spine and peripheral nerve surgery, brain tumors, traumatic brain injury (TBI), spinal cord trauma, chronic pain syndromes, chronic fatigue syndrome, neuralgias such as trigeminal neuralgia, glossopharyngeal neuralgia, postherpetic neuralgia and causalgia, pain arising from any of the following: lupus, sarcoidosis, arachnoiditis, arthritis, rheumatic disease, period pain, back pain, lower back pain, joint pain, abdominal pain, chest pain, labour pain, musculoskeletal and skin diseases, head trauma, and fibromyalgia.

Preferably, the inflammatory disease is selected from an inflammatory disorder, preferably selected from the group consisting of inflammatory diseases (e.g. rheumatoid arthritis, multiple sclerosis, Guillain-Barre syndrome, Crohn's disease, ulcerative colitis, psoriasis, graft versus host disease, systemic lupus, erythematosus or insulin-dependent diabetes mellitus), autoimmune diseases (e.g. toxic shock syndrome, osteoarthritis, diabetes or inflammatory bowel disease), acute pain, chronic pain, neuropathic pain, contact dermatitis, atherosclerosis, glomerulonephritis, reperfusion injury, bone resorption diseases, asthma, stroke, myocardial infarction, thermal injury, adult respiratory distress syndrome (ARDS), multiple organ injury secondary to trauma, dermatoses with acute inflammatory components, acute purulent meningitis, necrotising enterocolitis, syndromes associated with hemodialysis, septic shock, leukopherisis, granulocyte transfusion, acute or chronic inflammation of the lung caused by smoke inhalation, endometriosis, Behcet's disease, uveitis, ankylosing spondylitis, pancreatitis, cancer, Lyme disease, restenosis following percutaneous transluminal coronary angioplasty, Alzheimer's disease, traumatic arthritis, sepsis, chronic obstructive pulmonary disease, congestive heart failure, osteoporosis, cachexia, Parkinson's disease, periodontal diseases, gout, allergic diseases, age-related macular degeneration, infection and cystic fibrosis.

The present invention, in a sixth aspect, provides an agonist or antagonist of GPR86 identified by a method or use as set out.

In a seventh aspect of the present invention, there is provided use of such a molecule for the treatment, prophylaxis or alleviation of a inflammatory disease or pain.

According to an eighth aspect of the present invention, we provide a diagnostic kit for a inflammatory disease or pain or susceptibility thereto comprising any one or more of the following: a GPR86 polypeptide or pair thereof; an antibody against a GPR86 polypeptide; or a nucleic acid capable of encoding such.

We provide, according to a ninth aspect of the invention, a method of treating an individual suffering from inflammatory disease or pain, the method comprising increasing or decreasing the activity or amount of GPR86 polypeptide in the individual.

Preferably, the method comprises administering a GPR86 polypeptide, an agonist of GPR86 polypeptide or an antagonist of GPR86 to the individual.

There is provided, in accordance with a tenth aspect of the present invention, a method of diagnosis of a inflammatory disease or pain, the method comprising the steps of: (a) detecting the level or pattern of expression of GPR86 polypeptide in an animal suffering or suspected to be suffering from such a disease; and (b) comparing the level or pattern of expression with that of a normal animal.

SEQUENCE LISTINGS

Figure 1:
FIG. 1 is a diagram showing the results of analysis of the human GPR86 polypeptide (SEQ ID NO: 3) using the HMM structural prediction software of pfam (available at the pfam website maintained by the Sanger Institute).

SEQ ID NO: 1 shows the cDNA sequence of human GPR86. SEQ ID NO: 2 shows an open reading frame derived from SEQ ID NO: 1. SEQ ID NO: 3 shows the amino acid sequence of human GPR86. SEQ ID NO: 4 shows the open reading frame of a cDNA for Mouse GPR86. SEQ ID NO: 5 shows the amino acid sequence of Mouse GPR86. SEQ ID NO: 6 shows an alternative cDNA sequence of human GPR86. SEQ ID NO: 7 shows the alternative amino acid sequence of human GPR86. SEQ ID NOs: 8-20 show the knockout plasmid primer sequences. SEQ ID NO: 21 shows the knockout plasmid sequence.

Methods Employed

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements, *Current Protocols in Molecular Biology*, ch. 9, 13, and 16, John Wiley & Sons, New York, N.Y.); B. Roe, J. Crabtree, and A. Kahn, 1996, *DNA Isolation and Sequencing. Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA* Methods in Enzymology, Academic Press; Using Antibodies: A Laboratory Manual: Portable Protocol NO. I by Edward Harlow, David Lane, Ed Harlow (1999, Cold Spring Harbor Laboratory Press, ISBN 0-87969-544-7); Antibodies: A Laboratory Manual by Ed Harlow (Editor), David Lane (Editor) (1988, Cold Spring Harbor Laboratory Press, ISBN 0-87969-314-2), 1855, Lars-Inge Larsson "*Immunocytochemistry. Theory and Practice*", CRC Press inc., Boca Raton, Fla., 1988, ISBN 0-8493-6078-1, John D. Pound (ed); "*Immunochemical Protocols vol 80*", in the series: "Methods in Molecular Biology", Humana Press, Totowa, N.J., 1998, ISBN 0-89603-493-3, Handbook of Drug Screening, edited by Ramakrishna Seethala, Prabhavathi B. Fernandes (2001, New York, N.Y., Marcel Dekker, ISBN 0-8247-0562-9); Lab Ref: A Handbook of Recipes, Reagents, and Other Reference Tools for Use at the Bench, Edited Jane Roskams and Linda Rodgers, 2002, Cold Spring Harbor Laboratory, ISBN 0-87969-630-3; and The Merck Manual of Diagnosis and Therapy (17th Edition, Beers, M. H., and Berkow, R, Eds, ISBN: 0911910107, John Wiley & Sons). Each of these general texts is herein incorporated by reference. Each of these general texts is herein incorporated by reference.

DETAILED DESCRIPTION

GPR86

This document describes in general a G-Protein Coupled Receptor (GPCR), in particular, a purinoceptor type G-protein coupled receptor, which we refer to as GPR86, as well as homologues, variants or derivatives thereof.

We have identified that transgenic animals lacking functional GPR86 display an altered susceptibility to pain when compared to a wild-type animal. Specifically, GPR86 knockouts are less sensitive to pain. Furthermore, such animals exhibit an altered susceptibility to inflammatory pain, particularly decreased susceptibility to inflammatory pain.

Accordingly, we disclose the use of GPR86, homologues, variants or derivatives thereof, and modulators thereof in the treatment, relief or diagnosis of pain. This and other embodiments of the invention will be described in further detail below.

Expression Profile of GPR86

Figure 7:
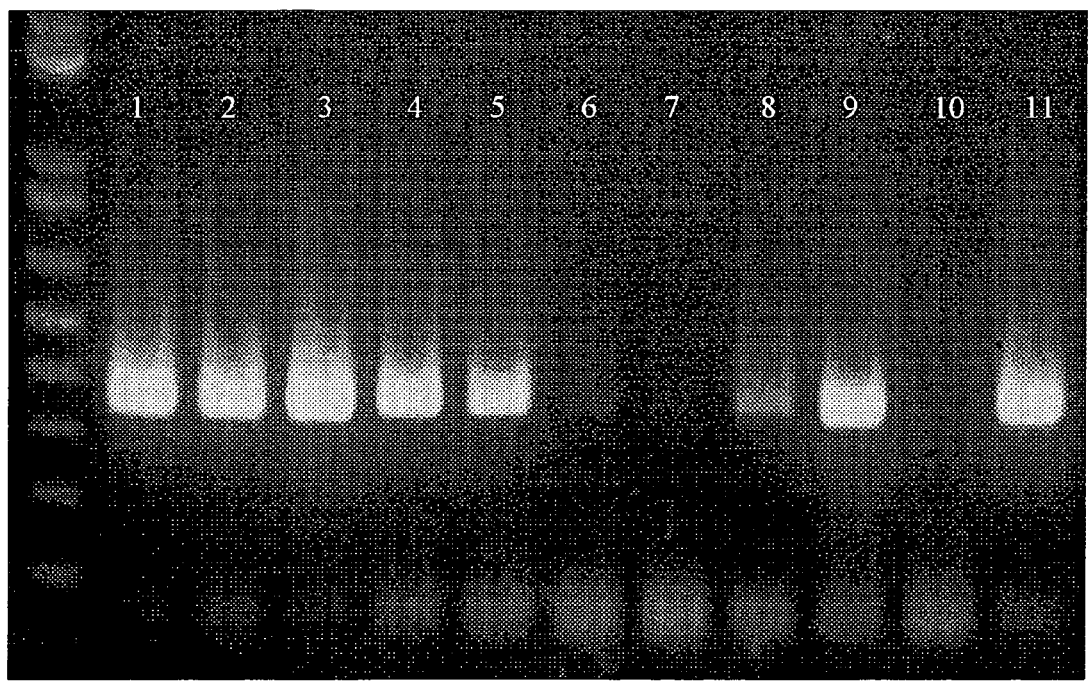
FIG. 7 is a figure showing the results of RT-PCR analysis of GPR86 expression in a number of human derived tissues. Lane 1: Bone Marrow; Lane 2: Thymus; Lane 3: Lymph node; Lane 4: Jurkat CD4+; Lane 5: Myla CD8+; Lane 6: Colo 720; Lane 7: THP1; Lane 8: Osteoblast; Lane 9: Chondrocyte; Lane 10. Negative control; Lane 11: Positive control (brain).

Polymerase chain reaction (PCR) amplification of GPR86 cDNA detects expression of GPR86 to varying abundance in bone marrow, thymus, lymph node, leukocytes, osteoblasts and chondrocytes of human derived tissues. It was also found in the human derived cell lines Jurkat CD4+ and Myla CD8+, both derived from T-cells. Low levels of expression was seen in Colo720, derived from lymphocytes, and THP1 cells which are derived from monocytes. (Example 4; FIG. 7).

Figure 8:
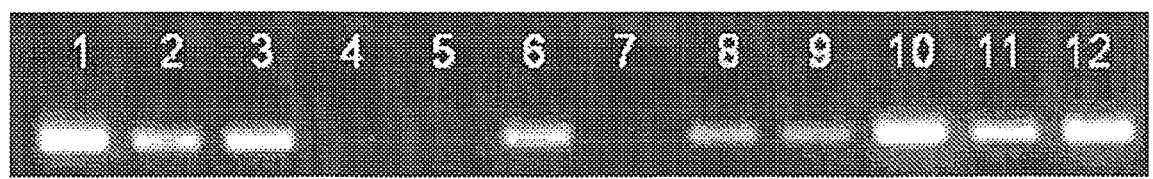
FIG. 8 is a figure showing the results of RT-PCR analysis of GPR86 expression in a number of mouse derived tissues. Lane 1: Spleen; Lane 2: Salivary gland; Lane 3: Spinal Cord; Lane 4: Muscle; Lane 5: Tongue; Lane 6: Ovary; Lane 7: Pancreas; Lane 8: Adipose; Lane 9: Testis; Lane 10: Heart; Lane 1: Eyes; Lane 12: Lung; Lane 13: Kidney; Lane 14: Thymus; Lane 15: Stomach+SI; Lane 16: Brain; Lane 17: Liver+Gb; Lane 18: Blood; Lane 19: Bladder; Lane 20: Adrenal; Lane 21: C57BL6J genomic DNA; Lane 22: 129SvEv genomic DNA.
Figure 8:
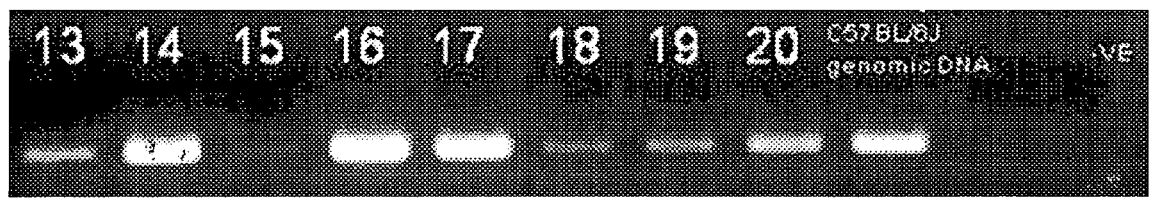

Furthermore, expression of GPR86 is also detected in spleen, salivary glands, spinal cord, tongue, adipose, testis, heart, eyes, lung, kidney, thymus, stomach and small intestine, brain, liver and gall bladder, blood, bladder and adrenal gland of mouse tissues (Example 4; FIG. 8).

Figure 3:
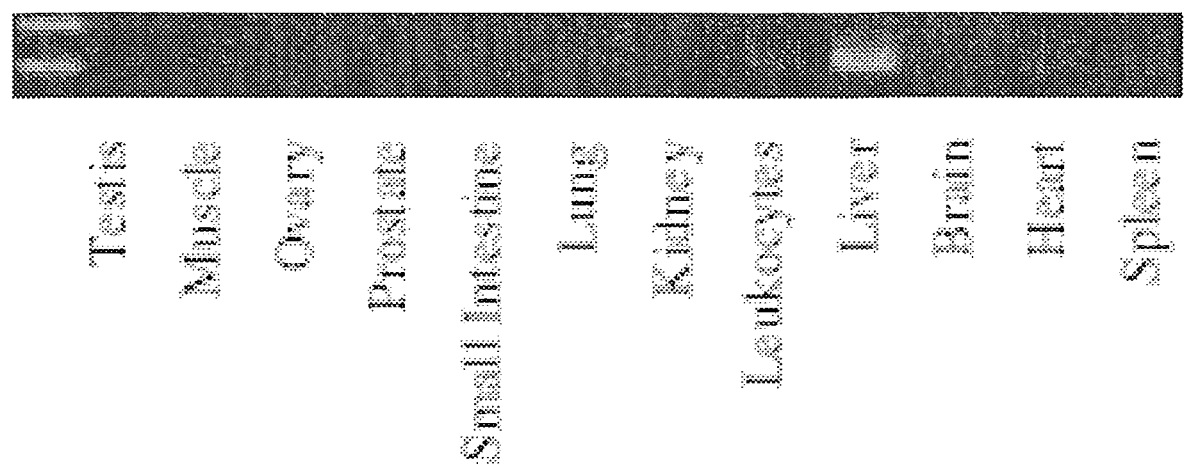
FIG. 3 is a diagram showing an expression profile for human GPR86 generated by reverse transcription-polymerase chain reaction (RT-PCR).

An expression profile of GPR86 is shown in FIG. 3.

Using GPR86 cDNA of SEQ ID NO: 1 and 6 to search the human EST data sources by BLASTN, identities are found in cDNA derived from libraries originating from human heart, placenta and colon and mouse skin, mammary and hypothalamus. This indicates that GPR86 is expressed in these normal or abnormal tissues. Accordingly, the GPR86 polypeptides, nucleic acids, probes, antibodies, expression vectors and ligands are useful for detection, diagnosis, treatment and other assays for diseases associated with over-, under- and abnormal expression of GPR86 in these and other tissues.

GPR86 Associated Diseases

According to the methods and compositions described here, GPR86 GPCR is useful for treating and diagnosing a range of diseases. These diseases are referred to for convenience as "GPR86 associated diseases".

Thus, GPR86 deficient animals may be used as models for GPR86 associated diseases. GPR86, its fragments, homologues, variants and derivatives thereof, as well as modulators, including particularly agonists and antagonists, may be used to diagnose or treat GPR86 associated diseases. In particular, GPR86 may be used in a screen for molecules capable of affecting its function, which may be used to treat a GPR86 associated disease.

We demonstrate here that human GPR86 maps to *Homo sapiens* chromosome 3q24. Accordingly, in a specific embodiment, GPR86 may be used to treat or diagnose a disease which maps to this locus, chromosomal band, region, arm or the same chromosome.

Known diseases which have been determined as being linked to the same locus, chromosomal band, region, arm or chromosome as the chromosomal location of GPR86 (i.e., *Homo sapiens* chromosome 3q24) include the following (locations in brackets): acute myelogenous leukemia (3q24), Hermansky-Pudlak syndrome (3q24), platelet ADP receptor defect (3q24-q25) and Dandy walker syndrome (3q24).

Accordingly, according to a preferred embodiment, GPR86 and its modulators (such as agonists and antagonists) may be used to diagnose or treat, by any means as described in this document, dopamine related diseases, such as Parkinson's disease, cardiac disease such as supraventricular or ventricular arrhythmias, hypotension, nausea, Tourette syndrome, stress, and pain.

Knockout mice deficient in GPR86 display a range of phenotypes, as demonstrated in the Examples.

Figure 4:
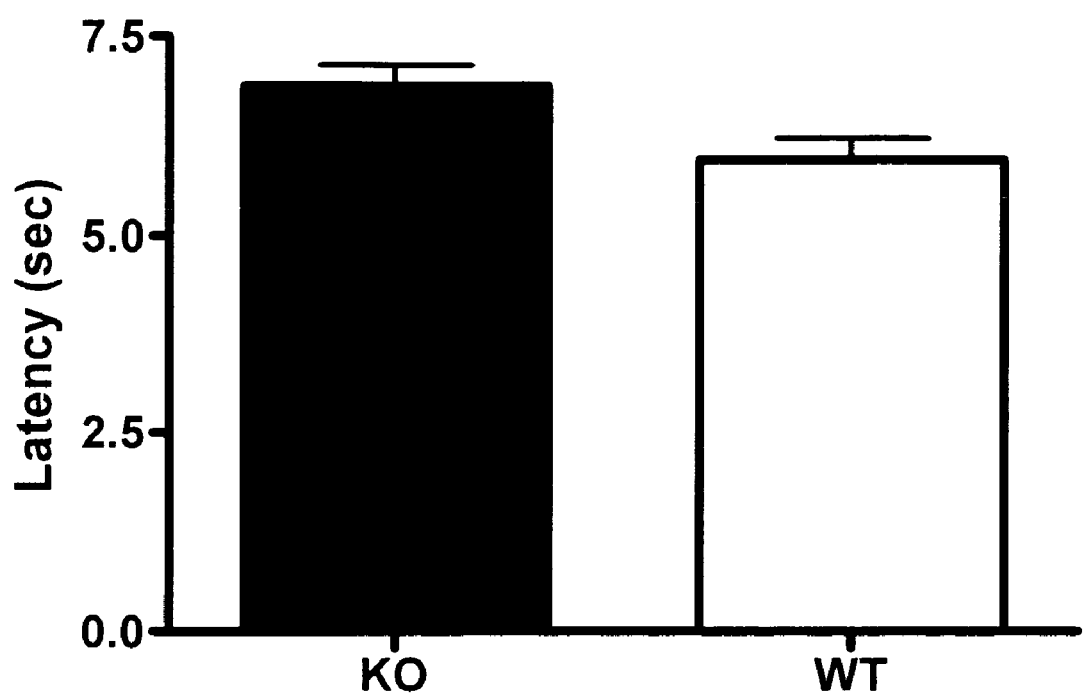
FIG. 4 is a graph of data from the Tail Flick Test, showing results from GPR86 knockout versus wild type animals.
Figure 6:
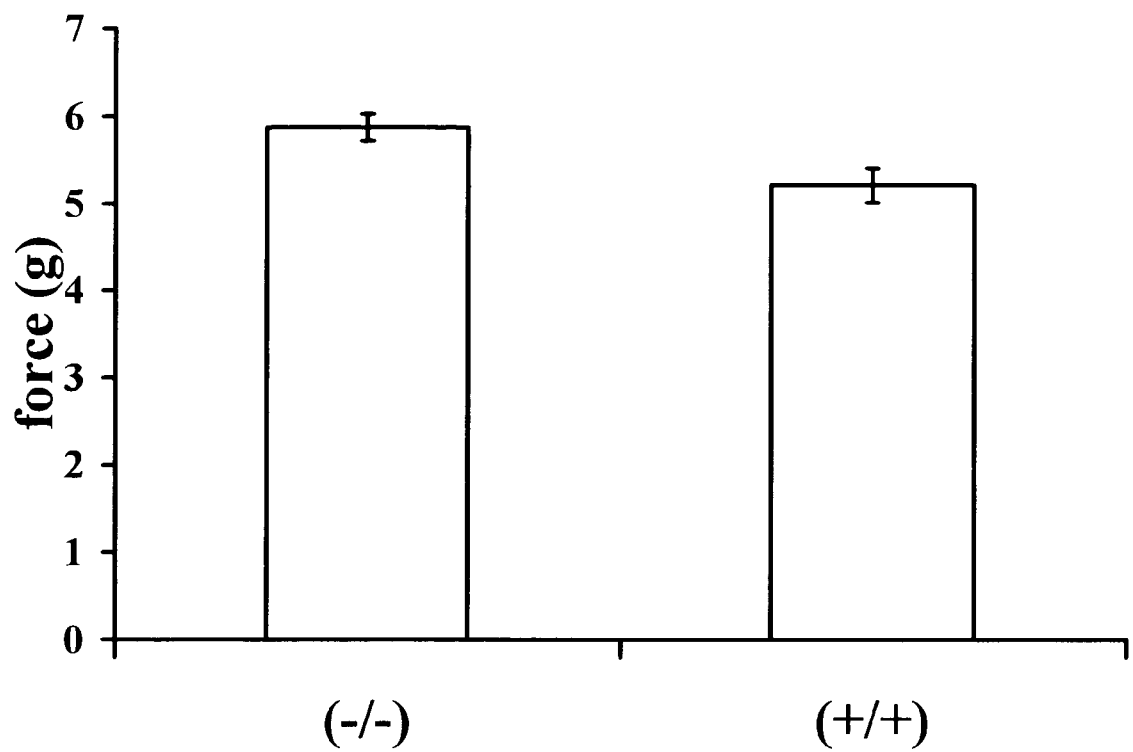
FIG. 6 is a graph of the Electronic Vonfrey test results (−/− knockout animals; +/+wildtype controls).

In particular, Example 5 and FIG. 4 demonstrate that, when tested in a Tail Flick Test, knockout animals deficient in functional GPR86 are less sensitive to external stimuli and pain than wild type animals. Similarly, Example 7 and FIG. 6 show that, when tested in a Von Frey Hair Test, knockout animals deficient in functional GPR86 are less sensitive to external stimuli and pain than wild type animals.

Accordingly, according to a preferred embodiment of the invention, GPR86 and its modulators (such as agonists and preferably antagonists) may be used to diagnose or treat, by any means as described in this document, pain and cancer. Particularly, pain includes neuropathic, post herpatic neuralgia, diabetic neuralgia, trigeminal neuralgia, alcohol (ethanol) related neuropathy, neuralgia of leprosy, vasculitic neuralgia, uremic neuralgia, Guillain Barre syndrome, multiple sclerosis, acute immune neuropathies, thoracic outlet syndrome, carpal tunnel syndrome, tarsal tunnel syndrome, meralgia paresthetica, complex regional pain syndrome, temperomandibular joint syndrome, atypical facial pain, lower back pain, lumbar spine stenosis, disc disease. Cervical pain, cervical spondylitic myeloneuropathy, cervical spondylosis, cervical disc disease, cervical myelofacial pain. Inflammatory pain, osteoarthritis, rheumatoid arthritis, inflammatory bowel disease. Cancer pain particularly cancer includes breast, prostate, colon, lung, ovarian, and bone cancer. Headache, migraine, tension headache, cluster headache, chronic paroxysmal hemicrania are included, as are visceral pain, dysmenorrhea, non peptic dyspepsia, non-cardiac chest pain, irritable bowel syndrome, phantom rectum pain. Thermal hyperalgesia and post operative pain.

Example 8 describes a test to measure the perception of pain to non-noxious stimuli (allodynia) following ligation of the 15 spinal nerve of an anaesthetised mouse. The results of Example 8 clearly show that knock-out mice lacking functional GPR86, have a decreased number of paw withdrawals when compared to wild type mice with functional GPR86. This shows that knock-out mice lacing GPR86 are resistant to the development of allodynia. Hence, GPR86 plays a role in the perception of pain and compounds which modulate, agonise or antagonise GPR86 activity have utility in the treatment, prevention or alleviation of neuropathic and inflammatory pain.

Furthermore, we demonstrate in the Examples that GPR86 is expressed in cells derived from immune responsive cells (Examples 3 and 4). Transgenic animals lacking functional GPR86 display a decreased tendency for inflammation, as shown in Example 6 and FIG. 5. This demonstrates that GPR86 is involved in inflammatory responses which include those that are involved in inflammatory and neuropathic aspects of pain.

According to another aspect, GPR86 and its modulators (such as agonists and antagonists) may be used to diagnose or treat, by any means as described in this document, inflammatory diseases (e.g. rheumatoid arthritis, multiple sclerosis, Guillain-Barre syndrome, Crohn's disease, ulcerative colitis, psoriasis, graft versus host disease, systemic lupus, erythematosus or insulin-dependent diabetes mellitus), autoimmune diseases (e.g. toxic shock syndrome, osteoarthritis, diabetes or inflammatory bowel disease), acute pain, chronic pain, neuropathic pain, contact dermatitis, atherosclerosis, glomerulonephritis, reperfusion injury, bone resorption diseases, asthma, stroke, myocardial infarction, thermal injury, adult respiratory distress syndrome (ARDS), multiple organ injury secondary to trauma, dermatoses with acute inflammatory components, acute purulent meningitis, necrotising enterocolitis, syndromes associated with hemodialysis, septic shock, leukopherisis, granulocyte transfusion, acute or chronic inflammation of the lung caused by smoke inhalation, endometriosis, Behcet's disease, uveitis, ankylosing spondylitis, pancreatitis, cancer, Lyme disease, restenosis following percutaneous transluminal coronary angioplasty, Alzheimer's disease, traumatic arthritis, sepsis, chronic obstructive pulmonary disease, congestive heart failure, osteoporosis, cachexia, Parkinson's disease, periodontal diseases, gout, allergic diseases, age-related macular degeneration, infection and cystic fibrosis.

For ease of convenience, the diseases which are treatable and/or diagnosable by use of GPR86 are referred to as "GPR86 associated diseases". In particularly preferred embodiments, the GPR86 associated diseases include those which include as a symptom pain (see paragraph above).

As noted above, GPR86 and its modulators (such as agonists and antagonists) may be used to diagnose and/or treat any of these specific diseases using any of the methods and compositions described here.

In particular, we specifically envisage the use of nucleic acids, vectors comprising GPR86 nucleic acids, polypeptides, including homologues, variants or derivatives thereof, pharmaceutical compositions, host cells, and transgenic animals comprising GPR86 nucleic acids and/or polypeptides, for the treatment or diagnosis of the specific diseases listed above. Furthermore, we envisage the use of compounds capable of interacting with or binding to GPR86 and capable of altering the level of endogenous cAMP, antibodies against GPR86, as well as methods of making or identifying these, in diagnosis or treatment of the specific diseases mentioned above. In particular, we include the use of any of these compounds, compositions, molecules, etc, in the production of vaccines for treatment or prevention of the specific diseases. We also disclose diagnostic kits for the detection of the specific diseases in an individual.

Methods of linkage mapping to identify such or further specific diseases treatable or diagnosable by use of GPR86 are known in the art, and are also described elsewhere in this document.

Pain

GPR86 and its variants as well as sequences encoding such, antibodies thereto, etc, as described in this document, may be used to diagnose and/or treat a number of diseases associated with pain.

Acute Pain

Acute pain is defined as short-term pain or pain with an easily identifiable cause. Acute pain is the body's warning of present damage to tissue or disease. It is often fast and sharp followed by aching pain. Acute pain is centralized in one area before becoming somewhat spread out.

Chronic Pain

Chronic pain is medically defined as pain that has lasted 6 months or longer. This constant or intermittent pain has often outlived its purpose, as it does not help the body to prevent injury. It is often more difficult to treat than acute pain. Expert care is generally necessary to treat any pain that has become chronic. When opioids are used for prolonged periods drug tolerance, chemical dependency and even psychological addiction may occur. While drug tolerance and chemical dependency are common among opioid users, psychological addiction is rare.

The experience of physiological pain can be grouped into four categories according to the source and related nociceptors (pain detecting nerves).

Cutaneous Pain

Cutaneous pain is caused by injury to the skin or superficial tissues. Cutaneous nociceptors terminate just below the skin, and due to the high concentration of nerve endings, produce a well-defined, localised pain of short duration. Example injuries that produce cutaneous pain include paper cuts, minor (first degree) burns and lacerations.

Somatic Pain

Somatic pain originates from ligaments, tendons, bones, blood vessels, and even nerves themselves, and are detected with somatic nociceptors. The scarcity of pain receptors in these areas produces a dull, poorly-localised pain of longer duration than cutaneous pain; examples include sprained ankle and broken bones.

Visceral Pain

Visceral pain originates from body organs visceral nociceptors are located within body organs and internal cavities. The even greater scarcity of nociceptors in these areas produces a pain usually more aching and of a longer duration than somatic pain. Visceral pain is extremely difficult to localise, and several injuries to visceral tissue exhibit "referred" pain, where the sensation is localised to an area completely unrelated to the site of injury. Myocardial ischaemia (the loss of blood flow to a pair of the heart muscle tissue) is possibly the best known example of referred pain; the sensation can occur in the upper chest as a restricted feeling, or as an ache in the left shoulder, arm or even hand.

Other Types of Pain

Phantom limb pain is the sensation of pain from a limb that one no longer has or no longer gets physical signals from—an experience almost universally reported by amputees and quadriplegics. Neuropathic pain ("neuralgia") can occur as a result of injury or disease to the nerve tissue itself. This can disrupt the ability of the sensory nerves to transmit correct information to the thalamus, and hence the brain interprets painful stimuli even though there is no obvious or documented physiologic cause for the pain.

Trigeminal neuralgia ("tic douloureux") refers to pain caused by injury or damage to the trigeminal nerve. The trigeminal nerve has 3 branches: V1 gives sensation to the area of the forehead and eye and V2 gives sensation to the nose and face and V3 gives sensation to the jaw and chin area. Each side of the face has a trigeminal nerve that gives sensation The one-sided pain of trigeminal neuralgia may extend through the cheek, mouth, nose and/or jaw muscles. Trigeminal neuralgia generally affects older people, although younger people or those with multiple sclerosis may also experience trigeminal neuralgia.

The primary symptom of trigeminal neuralgia is pain in either the forehead, cheek, chin or jawline. Severe cases may involve all three areas or both left and right sides. Pain episodes are severe, spastic and short, and are described as similar to what would be felt as electrical shock. The pain can be triggered by common daily activities such as brushing the teeth, talking, chewing, drinking, shaving or even kissing. The frequency of the pain episodes increases over time, becoming more disruptive and disabling.

Glossopharyngeal neuralgia is a clinical entity characterized by bursts of pain in the sensory distribution of the ninth cranial nerve. Except for the location of the pain and the stimulus for the pain the attacks are identical to trigeminal neuralgia. The typical pain is a severe lancinating, repetitive series of electrical-like stabs in the region of the tonsils or the back of the tongue, on one side. In addition, the pain may radiate to or originate in the ear.

The sensory stimulus which induces the pain is swallowing, and during severe attacks the patient may sit motionless, head flexed forward, allowing saliva to freely drool from the mouth. Cardiac arrest, syncope (fainting), and seizures have been associated with attacks of glossopharyngeal neuralgia. The cause of glossopharyngeal neuralgia in most cases is unknown. However, a certain number of cases have been ascribed to tumors, compression of the ninth nerve by the vertebral artery, and vascular malformations.

Postherpetic neuralgia refers to chronic pain continuing after an infection of herpes zoster virus. Herpes zoster, also known as shingles, is a recurrent infection of varicella-zoster (chickenpox) viral infection. The virus lies dormant within nerves until the patient's immunity wanes. The acute lesion of shingles causes pain which usually goes away. However, in a number of patients the pain continues chronically—postherpetic neuralgia.

The symptoms of herpes zoster include a lancinating, deep, continuous pain: the pain is in the thoracic region 65% and the face 20%. When the face is involved the virus shows a predilection for the ophthalmic division of the trigeminal nerve (top of the face above the eyebrows). The pain usually resolves spontaneously in 2 to 4 weeks. However, a few patients will have persistent pain. The pain is in the region of the previous rash and is exacerbated by gently stroking the affected skin and is relieved by applying pressure to the area. The rubbing of clothing is often very painful. This continuing pain is called postherpetic neuralgia. There is a higher incidence of postherpetic neuralgia in cases of herpes zoster involving the face.

Causalgia is a rare syndrome that follows partial peripheral nerve injuries. It is characterized by a triad of burning pain, autonomic dysfunction and trophic changes. Severe cases are called major causalgia. Minor causalgia describes less severe forms, similar to reflex sympathetic dystrophy (RSD). RSD has predominant muscular and joint symptoms, with osteoporosis being common on x-ray.

Causalgia is caused by peripheral nerve injuries, usually brachial plexus injuries. Denervation causes hypersensitivity resulting in increased pain and increased norepinephrine release causes the sympathetic findings. Symptoms include Pain: usually burning, and prominent in hand or foot. Onset in the majority is within 24 hours of injury. The median, ulnar and sciatic nerves are the most commonly involved. Almost any sensory stimulation worsens the pain. Vascular changes: Either increased blood by vasodilatation (warm and pink) or decreased blood by vasoconstriction (cold, mottled blue). Trophic changes: dry/scaly skin, stiff joints, tapering fingers, ridged uncut nails, either long/coarse hair or loss of hair, sweating alteration.

Identities and Similarities to GPR86

GPR86 is structurally related to other proteins of the G-protein coupled receptor family, as shown by the results of sequencing the amplified cDNA products encoding human GPR86. The cDNA sequence of SEQ ID NO: 1 contains an open reading flame (SEQ ID NO: 2, nucleotide numbers 19 to 1084) encoding a polypeptide of 354 amino acids shown in SEQ ID NO: 3. Human GPR86 is found to map to *Homo sapiens* chromosome 3q24. The alternative cDNA sequence of SEQ ID NO: 6 encodes a polypeptide shown in SEQ ID NO: 7.

P2Y12 platelet ADP receptor [*Homo sapiens*] Identities=154/316 (48%), Positives=211/316 (66%)

KIAA0001 putative G-protein-coupled receptor; G protein coupled receptor for UDP-glucose; Identities=140/295 (47%), Positives=193/295 (64%)

Platelet activating receptor homolog [*Homo sapiens*]; Identities=42/144 (29%), Positives=78/144 (54%)

Analysis of the GPR86 polypeptide (SEQ ID NO: 3) using the HMM structural prediction software of pfam (available at the pfam website maintained by the Sanger Institute) confirms that GPR86 peptide is a GPCR of the 7TM-1 structural class (see FIG. 1).

The mouse homologue of the human GPR86 has been cloned, and its nucleic acid sequence and amino acid sequence are shown as SEQ ID NO: 4 and SEQ ID NO: 5 respectively. The mouse GPR86 cDNA of SEQ ID NO: 4 shows a high degree of identity with human GPR86 (SEQ ID NO: 2) sequence, while the amino acid sequence (SEQ ID NO: 5) of mouse GPR86 shows a high degree of identity and similarity with human GPR86 (SEQ ID NO: 3 and SEQ ID NO: 7).

Human and mouse GPR86 are therefore members of a large family of G Protein Coupled Receptors (GPCRs).

GPR86 Polypeptides

As used here, the term "GPR86 polypeptide" is intended to refer to a polypeptide comprising the amino acid sequence shown in SEQ ID NO: 3 or SEQ ID NO: 5 or SEQ ID NO: 7, or a homologue, variant or derivative thereof. Preferably, the polypeptide comprises or is a homologue, variant or derivative of the sequence shown in SEQ ID NO: 3 or SEQ ID NO: 7. Most preferably, the polypeptide comprises or is a homologue, variant or derivative of the sequence shown in SEQ ID NO: 7.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids.

"Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications.

Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-inking, cyclization, disulfide bond formation, demethylation, formation of covalent cross-inks, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, *Proteins—Structure and Molecular Properties,* 2nd Ed., T. E. Creighton, W. H. Freeman and Company, New York, 1993 and Wold, F., *Posttranslational Protein Modifications: Perspectives and Prospects*, pgs. 1-12 in *Posttranslational Covalent Modification of Proteins*, B. C. Johnson, Ed., Academic Press, New York, 1983, Seifter et al., "Analysis for protein modifications and nonprotein cofactors", *Meth Enzymol* (1990) 182:626-646 and Rattan et al., "Protein Synthesis: Posttranslational Modifications and Aging", *Ann NY Acad Sci* (1992) 663:48-62.

The terms "variant", "homologue", "derivative" or "fragment" in relation to the present document include any substitution of, variation of, modification of, replacement of, deletion of or addition of one (or more) amino acid from or to a sequence. Unless the context admits otherwise, references to "GPR86" and "GPR86 GPCR" include references to such variants, homologues, derivatives and fragments of GPR86.

Preferably, as applied to GPR86, the resultant amino acid sequence has GPCR activity, more preferably having at least the same activity of GPR86 shown as SEQ ID NO: 3 or SEQ ID NO: 5 or SEQ ID NO: 7. In particular, the term "homologue" covers identity with respect to structure and/or function providing the resultant amino acid sequence has GPCR activity. With respect to sequence identity (i.e. similarity), preferably there is at least 70%, more preferably at least 75%, more preferably at least 85%, even more preferably at least 90% sequence identity. More preferably there is at least 95%, more preferably at least 98%, sequence identity. These terms also encompass polypeptides derived from amino acids which are allelic variations of GPR86 nucleic acid sequence.

Where reference is made to the "receptor activity" or "biological activity" of a receptor such as GPR86, these terms are intended to refer to the metabolic or physiological function of the GPR86 receptor, including similar activities or improved activities or these activities with decreased undesirable side effects. Also included are antigenic and immunogenic activities of the GPR86 receptor. Examples of GPCR activity, and methods of assaying and quantifying these activities, are known in the art, and are described in detail elsewhere in this document.

As used herein a "deletion" is defined as a change in either nucleotide or amino acid sequence in which one or more nucleotides or amino acid residues, respectively, are absent. As used herein an "insertion" or "addition" is that change in a nucleotide or amino acid sequence which has resulted in the addition of one or more nucleotides or amino acid residues, respectively, as compared to the naturally occurring substance. As used herein "substitution" results from the replacement of one or more nucleotides or amino acids by different nucleotides or amino acids, respectively.

GPR86 polypeptides described here may also have deletions, insertions or substitutions of amino acid residues which produce a silent change and result in a functionally equivalent amino acid sequence. Deliberate amino acid substitutions may be made on the basis of similarity in polarity, charge, solubility, hydrophobicity, hydrophilicity, and/or the amphipathic nature of the residues. For example, negatively charged amino acids include aspartic acid and glutamic acid, positively charged amino acids include lysine and arginine, and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

GPR86 polypeptides may further comprise heterologous amino acid sequences, typically at the N-terminus or C-terminus, preferably the N-terminus. Heterologous sequences may include sequences that affect intra or extracellular protein targeting (such as leader sequences). Heterologous sequences may also include sequences that increase the immunogenicity of the polypeptide and/or which facilitate identification, extraction and/or purification of the polypeptides. Another heterologous sequence that is particularly preferred is a polyamino acid sequence such as polyhistidine which is preferably N-terminal. A polyhistidine sequence of at least 10 amino acids, preferably at least 17 amino acids but fewer than 50 amino acids is especially preferred.

The GPR86 polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

GPR86 polypeptides are advantageously made by recombinant means, using known techniques. However they may also be made by synthetic means using techniques well known to skilled persons such as solid phase synthesis. Such polypeptides may also be produced as fusion proteins, for example to aid in extraction and purification. Examples of fusion protein partners include glutathione-S-transferase (GST), 6× His, GAL4 (DNA binding and/or transcriptional activation domains) and β-galactosidase. It may also be convenient to include a proteolytic cleavage site between the fusion protein partner and the protein sequence of interest to allow removal of fusion protein sequences, such as a thrombin cleavage site. Preferably the fusion protein will not hinder the function of the protein of interest sequence.

GPR86 polypeptides may be in a substantially isolated form. This term is intended to refer to alteration by the hand of man from the natural state. If an "isolated" composition or substance occurs in nature, it has been changed or removed from its original environment, or both. For example, a polynucleotide, nucleic acid or a polypeptide naturally present in a living animal is not "isolated," but the same polynucleotide, nucleic acid or polypeptide separated from the coexisting materials of its natural state is "isolated", as the term is employed herein.

It will however be understood that the GPR86 protein may be mixed with carriers or diluents which will not interfere with the intended purpose of the protein and still be regarded as substantially isolated. Such a polypeptide may also be in a substantially purified form, in which case it will generally comprise the protein in a preparation in which more than 90%, for example, 95%, 98% or 99% of the protein in the preparation is a GPR86 polypeptide.

This document also relates to peptides comprising a portion of a GPR86 polypeptide. Thus, fragments of GPR86 and its homologues, variants or derivatives are included. The peptides may be between 2 and 200 amino acids, preferably between 4 and 40 amino acids in length. The peptide may be derived from a GPR86 polypeptide as disclosed here, for example by digestion with a suitable enzyme, such as trypsin. Alternatively the peptide, fragment, etc may be made by recombinant means, or synthesised synthetically, The term "peptide" includes the various synthetic peptide variations known in the art, such as a retroinverso D peptides. The peptide may be an antigenic determinant and/or a T-cell epitope. The peptide may be immunogenic in vivo. Preferably the peptide is capable of inducing neutralising antibodies in vivo.

By aligning GPR86 sequences from different species, it is possible to determine which regions of the amino acid sequence are conserved between different species ("homologous regions"), and which regions vary between the different species ("heterologous regions").

The GPR86 polypeptides may therefore comprise a sequence which corresponds to at least part of a homologous region. A homologous region shows a high degree of homology between at least two species. For example, the homologous region may show at least 70%, preferably at least 80%, more preferably at least 90%, even more preferably at least 95% identity at the amino acid level using the tests described above. Peptides which comprise a sequence which corresponds to a homologous region may be used in therapeutic strategies as explained in further detail below. Alternatively, the GPR86 peptide may comprise a sequence which corresponds to at least part of a heterologous region. A heterologous region shows a low degree of homology between at least two species.

GPR86 Polynucleotides and Nucleic Acids

We further describe GPR86 polynucleotides, GPR86 nucleotides and GPR86 nucleic acids, methods of production, uses of these, etc, as described in further detail elsewhere in this document.

The terms "GPR86 polynucleotide", "GPR86 nucleotide" and "GPR86 nucleic acid" may be used interchangeably, and are intended to refer to a polynucleotide/nucleic acid comprising a nucleic acid sequence as shown in SEQ ID NO: 1, SEQ ID NO: 2, SEQ ID NO: 4, or SEQ ID NO: 6 or a homologue, variant or derivative thereof. Preferably, the polynucleotide/nucleic acid comprises or is a homologue, variant or derivative of the nucleic acid sequence SEQ ID NO: 1 or SEQ ID NO: 2, SEQ ID NO: 6, most preferably, SEQ ID NO: 2.

These terms are also intended to include a nucleic acid sequence capable of encoding a polypeptides and/or a peptide as described here, i.e., a GPR86 polypeptide. Thus, GPR86 polynucleotides and nucleic acids comprise a nucleotide sequence capable of encoding a polypeptide comprising the amino acid sequence shown in SEQ ID NO: 3, SEQ ID NO: 5 or SEQ ID NO: 7, or a homologue, variant or derivative thereof. Preferably, the GPR86 polynucleotides and nucleic acids comprise a nucleotide sequence capable of encoding a polypeptide comprising the amino acid sequence shown in SEQ ID NO: 7, or a homologue, variant or derivative thereof.

"Polynucleotide" generally refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA, thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

It will be understood by the skilled person that numerous nucleotide sequences can encode the same polypeptide as a result of the degeneracy of the genetic code.

As used herein, the term "nucleotide sequence" refers to nucleotide sequences, oligonucleotide sequences, polynucleotide sequences and variants, homologues, fragments and derivatives thereof (such as portions thereof). The nucleotide sequence may be DNA or RNA of genomic or synthetic or recombinant origin which may be double-stranded or single-stranded whether representing the sense or antisense strand or combinations thereof. The term nucleotide sequence may be prepared by use of recombinant DNA techniques (for example, recombinant DNA).

Preferably, the term "nucleotide sequence" means DNA.

The terms "variant", "homologue", "derivative" or "fragment" as used here include any substitution of, variation of, modification of, replacement of, deletion of or addition of one (or more) nucleic acids from or to the sequence of a GPR86 nucleotide sequence. Unless the context admits otherwise, references to "GPR86" and "GPR86 GPCR" include references to such variants, homologues, derivatives and fragments of GPR86.

Preferably, the resultant nucleotide sequence encodes a polypeptide having GPCR activity, preferably having at least the same activity of the GPCR shown as SEQ ID NO: 3, SEQ ID NO: 5, or SEQ ID NO:7. Preferably, the term "homologue" is intended to cover identity with respect to structure and/or function such that the resultant nucleotide sequence encodes a polypeptide which has GPCR activity. With respect to sequence identity (i.e. similarity), preferably there is at least 70%, more preferably at least 75%, more preferably at least 85%, more preferably at least 90% sequence identity. More preferably there is at least 95%, more preferably at least 98%, sequence identity. These terms also encompass allelic variations of the sequences.

Calculation of Sequence Homology

Sequence identity with respect to any of the sequences presented here can be determined by a simple "eyeball" comparison (i.e. a strict comparison) of any one or more of the sequences with another sequence to see if that other sequence has, for example, at least 70% sequence identity to the sequence(s).

Relative sequence identity can also be determined by commercially available computer programs that can calculate % identity between two or more sequences using any suitable algorithm for determining identity, using for example default parameters. A typical example of such a computer program is CLUSTAL. Other computer program methods to determine identify and similarity between the two sequences include but are not limited to the GCG program package (Devereux et al 1984 Nucleic Acids Research 12: 387) and FASTA (Atschul et al 1990 J Molec Biol 403-410).

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by insetting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (Ausubel et al., 1999 ibid, pages 7-58 to 7-60).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied. It is preferred to use the public default values for the GCG package, or in the case of other software, the default matrix, such as BLOSUM62.

Advantageously, the BLAST algorithm is employed, with parameters set to default values. The BLAST algorithm is described in detail at the website maintained by the National Center for Biotechnology Information, which is incorporated herein by reference. The search parameters, defined as follows, can be advantageously set to the defined default parameters.

Advantageously, "substantial identity" when assessed by BLAST equates to sequences which match with an EXPECT value of at least about 7, preferably at least about 9 and most preferably 10 or more. The default threshold for EXPECT in BLAST searching is usually 10.

BLAST (Basic Local Alignment Search Tool) is the heuristic search algorithm employed by the programs blastp, blastn, blastx, tblastn, and tblastx; these programs ascribe significance to their findings using the statistical methods of Karlin and Altschul (Karlin and Altschul 1990, Proc. Natl. Acad. Sci. USA 87:2264-68; Karlin and Altschul, 1993, Proc. Natl. Acad. Sci. USA 90:5873-7; see the website maintained by the National Center for Biotechnology Information) with a few enhancements. The BLAST programs are tailored for sequence similarity searching, for example to identify homologues to a query sequence. For a discussion of basic issues in similarity searching of sequence databases, see Altschul et al (1994) Nature Genetics 6:119-129.

The five BLAST programs available at the website maintained by the National Center for Biotechnology Information, perform the following tasks: blastp—compares an amino acid query sequence against a protein sequence database; blastn—compares a nucleotide query sequence against a nucleotide sequence database; blastx—compares the six-frame conceptual translation products of a nucleotide query sequence (both strands) against a protein sequence database; tblastn—compares a protein query sequence against a nucleotide sequence database dynamically translated in all six reading frames (both strands); tblastx—compares the six-frame translations of a nucleotide query sequence against the six-frame translations of a nucleotide sequence database.

BLAST uses the following search parameters:

HISTOGRAM—Display a histogram of scores for each search; default is yes. (See parameter H in the BLAST Manual).

DESCRIPTIONS—Restricts the number of short descriptions of matching sequences reported to the number specified; default limit is 100 descriptions. (See parameter V in the manual page).

EXPECT—The statistical significance threshold for reporting matches against database sequences; the default value is 10, such that 10 matches are expected to be found merely by chance, according to the stochastic model of Karlin and Altschul (1990). If the statistical significance ascribed to a match is greater than the EXPECT threshold, the match will not be reported. Lower EXPECT thresholds are more stringent, leading to fewer chance matches being reported. Fractional values are acceptable. (See parameter E in the BLAST Manual).

CUTOFF—Cutoff score for reporting high-scoring segment pairs. The default value is calculated from the EXPECT value (see above). HSPs are reported for a database sequence only if the statistical significance ascribed to them is at least as high as would be ascribed to a lone HSP having a score equal to the CUTOFF value. Higher CUTOFF values are more stringent, leading to fewer chance matches being reported. (See parameter S in the BLAST Manual). Typically, significance thresholds can be more intuitively managed using EXPECT.

ALIGNMENTS—Restricts database sequences to the number specified for which high-scoring segment pairs (HSPs) are reported; the default limit is 50. If more database sequences than this happen to satisfy the statistical significance threshold for reporting (see EXPECT and CUTOFF below), only the matches ascribed the greatest statistical significance are reported. (See parameter B in the BLAST Manual).

MATRIX—Specify an alternate scoring matrix for BLASTP, BLASTX, TBLASTN and TBLASTX. The default matrix is BLOSUM62 (Henikoff & Henikoff, 1992). The valid alternative choices include: PAM40, PAM120, PAM250 and IDENTITY. No alternate scoring matrices are available for BLASTN; specifying the MATRIX directive in BLASTN requests returns an error response.

STRAND—Restrict a TBLASTN search to just the top or bottom strand of the database sequences; or restrict a BLASTN, BLASTX or TBLASTX search to just reading frames on the top or bottom strand of the query sequence.

FILTER—Mask off segments of the query sequence that have low compositional complexity, as determined by the SEG program of Wootton & Federhen (1993) Computers and Chemistry 17:149-163, or segments consisting of short-periodicity internal repeats, as determined by the XNU program of Claverie & States (1993) Computers and Chemistry 17:191-201, or, for BLASTN, by the DUST program of Tatusov and Lipman (see the website maintained by the National Center for Biotechnology Information). Filtering can eliminate statistically significant but biologically uninteresting reports from the blast output (e.g., hits against common acidic-, basic- or proline-rich regions), leaving the more biologically interesting regions of the query sequence available for specific matching against database sequences.

Low complexity sequence found by a filter program is substituted using the letter "N" in nucleotide sequence (e.g., "NNNNNNNNNNNNN") and the letter "X" in protein sequences (e.g., "XXXXXXXXX").

Filtering is only applied to the query sequence (or its translation products), not to database sequences. Default filtering is DUST for BLASTN, SEG for other programs.

It is not unusual for nothing at all to be masked by SEG, XNU, or both, when applied to sequences in SWISS-PROT, so filtering should not be expected to always yield an effect. Furthermore, in some cases, sequences are masked in their entirety, indicating that the statistical significance of any matches reported against the unfiltered query sequence should be suspect.

NCBI-gi—Causes NCBI gi identifiers to be shown in the output, in addition to the accession and/or locus name.

Most preferably, sequence comparisons are conducted using the simple BLAST search algorithm provided at the website maintained by the National Center for Biotechnology Information. In some embodiments, no gap penalties are used when determining sequence identity.

Hybridisation

We further describe nucleotide sequences that are capable of hybridising to the sequences presented herein, or any fragment or derivative thereof, or to the complement of any of the above.

Hybridization means a "process by which a strand of nucleic acid joins with a complementary strand through base pairing" (Coombs J (1994) Dictionary of Biotechnology, Stockton Press, New York N.Y.) as well as the process of amplification as carried out in polymerase chain reaction technologies as described in Dieffenbach C W and G S Dveksler (1995, PCR Primer, a Laboratory Manual, Cold Spring Harbor Press, Plainview N.Y.).

Hybridization conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.), and confer a defined "stringency" as explained below.

Nucleotide sequences capable of selectively hybridising to the nucleotide sequences presented herein, or to their complement, will be generally at least 70%, preferably at least 75%, more preferably at least 85 or 90% and even more preferably at least 95% or 98% homologous to the corresponding nucleotide sequences presented herein over a region of at least 20, preferably at least 25 or 30, for instance at least 40, 60 or 100 or more contiguous nucleotides. Preferred nucleotide sequences will comprise regions homologous to SEQ ID NO: 1, 2 or 4, preferably at least 70%, 80% or 90% and more preferably at least 95% homologous to one of the sequences.

The term "selectively hybridizable" means that the nucleotide sequence used as a probe is used under conditions where a target nucleotide sequence is found to hybridize to the probe at a level significantly above background. The background hybridization may occur because of other nucleotide sequences present, for example, in the cDNA or genomic DNA library being screened. In this event, background implies a level of signal generated by interaction between the probe and a non-specific DNA member of the library which is less than 10 fold, preferably less than 100 fold as intense as the specific interaction observed with the target DNA. The intensity of interaction may be measured, for example, by radiolabelling the probe, e.g. with $^{32}P$.

Also included within the scope of the present document are nucleotide sequences that are capable of hybridizing to the nucleotide sequences presented herein under conditions of intermediate to maximal stringency. Hybridization conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego Calif.), and confer a defined "stringency" as explained below.

Maximum stringency typically occurs at about Tm-5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridization can be used to identify or detect identical nucleotide sequences while an intermediate (or low) stringency hybridization can be used to identify or detect similar or related nucleotide sequences.

In a preferred embodiment, we disclose nucleotide sequences that can hybridise to one or more of the GPR86 nucleotide sequences under stringent conditions (e.g. 65° C. and 0.1×SSC {1×SSC=0.15 M NaCl, 0.015 M $Na_3$ Citrate pH 7.0). Where the nucleotide sequence is double-stranded, both strands of the duplex, either individually or in combination, are encompassed. Where the nucleotide sequence is single-stranded, it is to be understood that the complementary sequence of that nucleotide sequence is also included within the scope of this document.

We further describe nucleotide sequences that are capable of hybridising to the sequences that are complementary to the sequences presented herein, or any fragment or derivative thereof. Likewise, nucleotide sequences that are complementary to sequences that are capable of hybridising to the sequences described here are also included. These types of nucleotide sequences are examples of variant nucleotide sequences. In this respect, the term "variant" encompasses sequences that are complementary to sequences that are capable of hybridising to the nucleotide sequences presented herein. Preferably, however, the term "variant" encompasses sequences that are complementary to sequences that are capable of hybridising under stringent conditions (e.g. 65° C. and 0.1×SSC {1×SSC=0.15 M NaCl, 0.015 Na$_3$ citrate pH 7.0}) to the nucleotide sequences presented herein.

Cloning of GPR86 and Homologues

We describe nucleotide sequences that are complementary to the sequences presented here, or any fragment or derivative thereof. If the sequence is complementary to a fragment thereof then that sequence can be used as a probe to identify and clone similar GPCR sequences in other organisms etc.

Our disclosure thus enables the cloning of GPR86, its homologues and other structurally or functionally related genes from human and other species such as mouse, pig, sheep, etc to be accomplished. Polynucleotides which are identical or sufficiently identical to a nucleotide sequence contained in SEQ ID NO: 1, SEQ ID NO: 2, SEQ ID NO: 4 or a fragment thereof, may be used as hybridization probes for cDNA and genomic DNA, to isolate partial or full-length cDNAs and genomic clones encoding GPR86 from appropriate libraries. Such probes may also be used to isolate cDNA and genomic clones of other genes (including genes encoding homologues and orthologues from species other than human) that have sequence similarity, preferably high sequence similarity, to the GPR86 gene. Hybridization screening, cloning and sequencing techniques are known to those of skill in the art and are described in, for example, Sambrook et al (supra).

Typically nucleotide sequences suitable for use as probes are 70% identical, preferably 80% identical, more preferably 90% identical, even more preferably 95% identical to that of the referent. The probes generally will comprise at least 15 nucleotides. Preferably, such probes will have at least 30 nucleotides and may have at least 50 nucleotides.

Particularly preferred probes will range between 150 and 500 nucleotides, more particularly about 300 nucleotides.

In one embodiment, to obtain a polynucleotide encoding a GPR86 polypeptide, including homologues and orthologues from species other than human, comprises the steps of screening an appropriate library under stringent hybridization conditions with a labelled probe having the SEQ ID NO: 1, SEQ ID NO: 2, SEQ ID NO: 4 or a fragment thereof and isolating partial or full-length cDNA and genomic clones containing said polynucleotide sequence. Such hybridization techniques are well known to those of skill in the art. Stringent hybridization conditions are as defined above or alternatively conditions under overnight incubation at 42 degrees C. in a solution comprising: 50% formamide, 5×SSC (150 mM NaCl, 15 mM trisodium citrate), 50 mM sodium phosphate (pH7.6), 5× Denhardt's solution, 10% dextran sulphate, and 20 microgram/ml denatured, sheared salmon sperm DNA, followed by washing the filters in 0.1×SSC at about 65 degrees C.

Functional Assay for GPR86

The cloned putative GPR86 polynucleotides may be verified by sequence analysis or functional assays. For example, the putative GPR86 or homologue may be assayed for receptor activity as follows. Capped RNA transcripts from linearized plasmid templates encoding the GPR86 receptor cDNAs are synthesized in vitro with RNA polymerases in accordance with standard procedures. In vitro transcripts are suspended in water at a final concentration of 0.2 mg/ml. Ovarian lobes are removed from adult female toads, Stage V defolliculated oocytes are obtained, and RNA transcripts (10 ng/oocyte) are injected in a 50 nl bolus using a microinjection apparatus. Two electrode voltage clamps are used to measure the currents from individual Xenopus oocytes in response to agonist exposure. Recordings are made in standard medium consisting of (in mM) NaCl 115, KCl 2.5, CaCl$_2$ 1.8, NaOH-HEPES 10, pH7.2 at room temperature. The Xenopus system may also be used to screen known ligands and tissue/cell extracts for activating ligands, as described in further detail below.

Expression Assays for GPR86

In order to design useful therapeutics for treating GPR86 associated diseases, it is useful to determine the expression profile of GPR86 (whether wild-type or a particular mutant). Thus, methods known in the art may be used to determine the organs, tissues and cell types (as well as the developmental stages) in which GPR86 is expressed. For example, traditional or "electronic" Northerns may be conducted. Reverse-transcriptase PCR (RT-PCR) may also be employed to assay expression of the GPR86 gene or mutant. More sensitive methods for determining the expression profile of GPR86 include RNAse protection assays, as known in the art.

Northern analysis is a laboratory technique used to detect the presence of a transcript of a gene and involves the hybridization of a labeled nucleotide sequence to a membrane on which RNAs from a particular cell type or tissue have been bound. (Sambrook, supra, ch. 7 and Ausubel, F. M. et al. supra, ch. 4 and 16). Analogous computer techniques ("electronic Northerns") applying BLAST may be used to search for identical or related molecules in nucleotide databases such as GenBank or the LIFESEQ database (Incyte Pharmaceuticals). This type of analysis has advantages in that they may be faster than multiple membrane-based hybridizations. In addition, the sensitivity of the computer search can be modified to determine whether any particular match is categorized as exact or homologous.

The polynucleotides and polypeptides described here, including the probes described above, may be employed as research reagents and materials for discovery of treatments and diagnostics to animal and human disease, as explained in further detail elsewhere in this document.

Expression of GPR86 Polypeptides

We further include a process for producing a GPR86 polypeptide. The method comprises in general culturing a host cell comprising a nucleic acid encoding GPR86 polypeptide, or a homologue, variant, or derivative thereof, under suitable conditions (i.e., conditions in which the GPR86 polypeptide is expressed).

In order to express a biologically active GPR86, the nucleotide sequences encoding GPR86 or homologues, variants, or derivatives thereof are inserted into appropriate expression vector, i.e., a vector which contains the necessary elements for the transcription and translation of the inserted coding sequence.

Methods which are well known to those skilled in the art are used to construct expression vectors containing sequences encoding GPR86 and appropriate transcriptional and translational control elements. These methods include in vitro recombinant DNA techniques, synthetic techniques, and in vivo genetic recombination. Such techniques are described in Sambrook, J. et al. (1989; Molecular Cloning, A Laboratory Manual, ch. 4, 8, and 16-17, Cold Spring Harbor Press, Plainview, N.Y.) and Ausubel, F. M. et al. (1995 and periodic supplements; Current Protocols in Molecular Biology, ch. 9, 13, and 16, John Wiley & Sons, New York, N.Y.).

A variety of expression vector/host systems may be utilized to contain and express sequences encoding GPR86. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus (CaMV) or tobacco mosaic virus (TMV)) or with bacterial expression vectors (e.g., Ti or pBR322 plasmids); or animal cell systems. It does not matter which host cell is employed.

The "control elements" or "regulatory sequences" are those non-translated regions of the vector (i.e., enhancers, promoters, and 5' and 3' untranslated regions) which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, La Jolla, Calif.) or PSPORT1 plasmid (GIBCO/BRL), and the like, may be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding GPR86, vectors based on SV40 or EBV may be used with an appropriate selectable marker.

In bacterial systems, a number of expression vectors may be selected depending upon the use intended for GPR86. For example, when large quantities of GPR86 are needed for the induction of antibodies, vectors which direct high level expression of fusion proteins that are readily purified may be used. Such vectors include, but are not limited to, multifunctional *E. coli* cloning and expression vectors such as BLUESCRIPT (Stratagene), in which the sequence encoding GPR86 may be ligated into the vector in frame with sequences for the amino-terminal Met and the subsequent 7 residues of β-galactosidase so that a hybrid protein is produced, pIN vectors (Van Heeke, G. and S. M. Schuster (1989) J. Biol. Chem. 264:5503-5509), and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast *Saccharomyces cerevisiae*, a number of vectors containing constitutive or inducible promoters, such as alpha factor, alcohol oxidase, and PGH, may be used. For reviews, see Ausubel (supra) and Grant et al. (1987; Methods Enzymol. 153:516-544).

In cases where plant expression vectors are used, the expression of sequences encoding GPR86 may be driven by any of a number of promoters. For example, viral promoters such as the 35S and 19S promoters of CaMV may be used alone or in combination with the omega leader sequence from TMV. (Takamatsu, N. (1987) EMBO J. 6:307-311). Alternatively, plant promoters such as the small subunit of RUBISCO or heat shock promoters may be used. (Coruzzi, G. et al. (1984) EMBO J. 3:1671-1680; Broglie, R. et al. (1984) Science 224:838-843; and Winter, J. et al. (1991) Results Probl. Cell Differ. 17:85-105). These constructs can be introduced into plant cells by direct DNA transformation or pathogen-mediated transfection. Such techniques are described in a number of generally available reviews. (See, for example, Hobbs, S. or Murry, L. E. in McGraw Hill Yearbook of Science and Technology (1992) McGraw Hill, New York, N.Y., pp. 191-196).

An insect system may also be used to express GPR86. For example, in one such system, *Autographa californica* nuclear polyhedrosis virus (AcNPV) is used as a vector to express foreign genes in *Spodoptera frungiperda* cells or in *Trichophusia larvae*. The sequences encoding GPR86 may be cloned into a non-essential region of the virus, such as the polyhedrin gene, and placed under control of the polyhedrin promoter. Successful insertion of GPR86 will render the polyhedrin gene inactive and produce recombinant virus lacking coat protein. The recombinant viruses may then be used to infect, for example, *S. frugiperda* cells or *Trichoplusia larvae* in which GPR86 may be expressed. (Engelhard, E. K. et al. (1994) Proc. Nat. Acad. Sci. 91:3224-3227).

In mammalian host cells, a number of viral-based expression systems may be utilized. In cases where an adenovirus is used as an expression vector, sequences encoding GPR86 may be ligated into an adenovirus transcription/translation complex consisting of the late promoter and tripartite leader sequence. Insertion in a non-essential E1 or E3 region of the viral genome may be used to obtain a viable virus which is capable of expressing GPR86 in infected host cells. (Logan, J. and T. Shenk (1984) Proc. Natl. Acad. Sci. 81:3655-3659). In addition, transcription enhancers, such as the Rous sarcoma virus (RSV) enhancer, may be used to increase expression in mammalian host cells.

Thus, for example, the GPR86 receptors may be expressed in either human embryonic kidney 293 (HEK293) cells or adherent dhfr CHO cells. To maximize receptor expression, typically all 5' and 3' untranslated regions (UTRs) are removed from the receptor cDNA prior to insertion into a pCDN or pCDNA3 vector. The cells are transfected with individual receptor cDNAs by lipofectin and selected in the presence of 400 mg/ml G418. After 3 weeks of selection, individual clones are picked and expanded for further analysis. HEK293 or CHO cells transfected with the vector alone serve as negative controls. To isolate cell lines stably expressing the individual receptors, about 24 clones are typically selected and analyzed by Northern blot analysis. Receptor mRNAs are generally detectable in about 50% of the G418-resistant clones analyzed.

Human artificial chromosomes (HACs) may also be employed to deliver larger fragments of DNA than can be contained and expressed in a plasmid. HACs of about 6 kb to 10 Mb are constructed and delivered via conventional delivery methods (liposomes, polycationic amino polymers, or vesicles) for therapeutic purposes.

Specific initiation signals may also be used to achieve more efficient translation of sequences encoding GPR86. Such signals include the ATG initiation codon and adjacent sequences. In cases where sequences encoding GPR86 and its initiation codon and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers appropriate for the particular cell system used, such as those described in the literature. (Scharf, D. et al. (1994) Results Probl. Cell Differ. 20:125-162).

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding, and/or function. Different host cells which have specific cellular machinery and characteristic mechanisms for post-translational activities (e.g., CHO, HeLa, MDCK, HEK293, and WI38), are available from the American Type Culture Collection (ATCC, Bethesda, Md.) and may be chosen to ensure the correct modification and processing of the foreign protein.

For long term, high yield production of recombinant proteins, stable expression is preferred. For example, cell lines capable of stably expressing GPR86 can be transformed using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase genes (Wigler, M. et al. (1977) Cell 11:223-32) and adenine phosphoribosyltransferase genes (Lowy, I. et al. (1980) Cell 22:817-23), which can be employed in tk$^-$ or apr$^-$ cells, respectively. Also, antimetabolite, antibiotic, or herbicide resistance can be used as the basis for, selection. For example, dhfr confers resistance to methotrexate (Wigler, M. et al. (1980) Proc. Natl. Acad. Sci. 77:3567-70), npt confers resistance to the aminoglycosides neomycin and G-418 (Colbere-Garapin, F. et al (1981) J. Mol. Biol. 150:1-14), and als or pat confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine. (Hartman, S. C. and R. C. Mulligan (1988) Proc. Natl. Acad. Sci. 85:8047-51). Recently, the use of visible markers has gained popularity with such markers as anthocyanins, β-glucuronidase and its substrate GUS, and luciferase and its substrate luciferin. These markers can be used not only to identify transformants, but also to quantify the amount of transient or stable protein expression attributable to a specific vector system. (Rhodes, C. A. et al. (1995) Methods Mol. Biol. 55:121-131).

Although the presence/absence of marker gene expression suggests that the gene of interest is also present, the presence and expression of the gene may need to be confirmed. For example, if the sequence encoding GPR86 is inserted within a marker gene sequence, transformed cells containing sequences encoding GPR86 can be identified by the absence of marker gene function. Alternatively, a marker gene can be placed in tandem with a sequence encoding GPR86 under the control of a single promoter. Expression of the marker gene in response to induction or selection usually indicates expression of the tandem gene as well.

Alternatively, host cells which contain the nucleic acid sequence encoding GPR86 and express GPR86 may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein sequences.

The presence of polynucleotide sequences encoding GPR86 can be detected by DNA-DNA or DNA-RNA hybridization or amplification using probes or fragments or fragments of polynucleotides encoding GPR86. Nucleic acid amplification based assays involve the use of oligonucleotides or oligomers based on the sequences encoding GPR86 to detect transformants containing DNA or RNA encoding GPR86.

A variety of protocols for detecting and measuring the expression of GPR86, using either polyclonal or monoclonal antibodies specific for the protein, are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on GPR86 is preferred, but a competitive binding assay may be employed. These and other assays are well described in the art, for example, in Hampton, R. et al. (1990; Serological Methods, a Laboratory Manual, Section IV, APS Press, St Paul, Minn.) and in Maddox, D. E. et al. (1983; J. Exp. Med. 158:1211-1216).

A wide variety of labels and conjugation techniques are known by those skilled in the art and may be used in various nucleic acid and amino acid assays. Means for producing labeled hybridization or PCR probes for detecting sequences related to polynucleotides encoding GPR86 include oligolabeling, nick translation, end-labeling, or PCR amplification using a labeled nucleotide. Alternatively, the sequences encoding GPR86, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Mich.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding GPR86 may be cultured under conditions suitable for the expression and recovery of the protein from cell culture. The protein produced by a transformed cell may be located in the cell membrane, secreted or contained intracellularly depending on the sequence and/or the vector used. As will be understood by those of skill in the art, expression vectors containing polynucleotides which encode GPR86 may be designed to contain signal sequences which direct secretion of GPR86 through a prokaryotic or eukaryotic cell membrane. Other constructions may be used to join sequences encoding GPR86 to nucleotide sequences encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences, such as those specific for Factor XA or enterokinase (Invitrogen, San Diego, Calif.), between the purification domain and the GPR86 encoding sequence may be used to facilitate purification. One such expression vector provides for expression of a fusion protein containing GPR86 and a nucleic acid encoding 6 histidine residues preceding a thioredoxin or an enterokinase cleavage site. The histidine residues facilitate purification on immobilized metal ion affinity chromatography (IMIAC; described in Porath, J. et al. (1992) Prot. Exp. Purif. 3: 263-281), while the enterokinase cleavage site provides a means for purifying GPR86 from the fusion protein. A discussion of vectors which contain fusion proteins is provided in Kroll, D. J. et al. (1993; DNA Cell Biol. 12:441-453).

Fragments of GPR86 may be produced not only by recombinant production, but also by direct peptide synthesis using solid-phase techniques. (Merrifield J. (1963) J. Am. Chem. Soc. 85:2149-2154). Protein synthesis may be performed by manual techniques or by automation. Automated synthesis may be achieved, for example, using the Applied Biosystems 431A peptide synthesizer (Perkin Elmer). Various fragments of GPR86 may be synthesized separately and then combined to produce the full length molecule.

Biosensors

The GPR86 polypeptides, nucleic acids, probes, antibodies, expression vectors and ligands are useful as (and for the production of) biosensors.

According to Aizawa (1988), *Anal. Chem. Symp.* 17: 683, a biosensor is defined as being a unique combination of a receptor for molecular recognition, for example a selective layer with immobilized antibodies or receptors such as a GPR86 G-protein coupled receptor, and a transducer for transmitting the values measured. One group of such biosensors will detect the change which is caused in the optical properties of a surface layer due to the interaction of the receptor with the surrounding medium. Among such techniques may be mentioned especially ellipso-metry and surface plasmon resonance. Biosensors incorporating GPR86 may be used to detect the presence or level of GPR86 ligands, for example, nucleotides such as purines or purine analogues, or analogues of these ligands. The construction of such biosensors is well known in the art.

Thus, cell lines expressing GPR86 receptor may be used as reporter systems for detection of ligands such as ATP via receptor-promoted formation of [3H]inositol phosphates or other second messengers (Watt et al., 1998, *J Biol Chem* May 29; 273(22):14053-8). Receptor-ligand biosensors are also described in Hoffman et al., 2000, *Proc Natl Acad Sci USA* Oct. 10; 97 (21):11215-20. Optical and other biosensors comprising GPR86 may also be used to detect the level or presence of interaction with G-proteins and other proteins, as described by, for example, Figler et al, 1997, *Biochemistry* Dec. 23; 36 (51):16288-99 and Sarrio et al., 2000, *Mol Cell Biol* 2000 July; 20(14):5164-74). Sensor units for biosensors are described in, for example, U.S. Pat. No. 5,492,840.

Screening Assays

The GPR86 polypeptide, including homologues, variants, and derivatives, whether natural or recombinant, may be employed in a screening process for compounds which bind the receptor and which activate (agonists) or inhibit activation of (antagonists) of GPR86.

Thus, the polypeptides may also be used to assess the binding of small molecule substrates and ligands in, for example, cells, cell-free preparations, chemical libraries, and natural product mixtures. These substrates and ligands may be natural substrates and ligands or may be structural or functional mimetics. See Coligan et al., *Current Protocols in Immunology* 1(2):Chapter 5 (1991).

GPR86 polypeptides are responsible for many biological functions, including many pathologies such as those described above under "GPR86 associated diseases". Accordingly, it is desirous to find compounds and drugs which stimulate GPR86 on the one hand and which can inhibit the function of GPR86 on the other hand. In general, agonists and antagonists are employed for therapeutic and prophylactic purposes for such conditions as dopamine related diseases, such as Parkinson's disease, cardiac disease such as supraventricular or ventricular arrhythmias, hypotension, nausea, Tourette syndrome, stress and pain.

An agonist may activate the GPR86 receptor to any degree. Similarly, an antagonist may deactivate, or inhibit the activation of, the GPR86 to any degree. The GPR86 receptor may therefore be deactivated partially to any degree to its inherent, basal or background level of activity by an antagonist (partial antagonist) or fully to such a level (antagonist or full antagonist). The antagonist may deactivate the receptor even further, for example to zero activity (inverse agonist). The term "antagonist" therefore specifically includes both full antagonists, partial antagonists and inverse agonists.

Also included within the terms "agonist" and "antagonist" are those molecules which modulate the expression of GPR86, at the transcriptional level and/the translational level, as well as those which modulate its activity.

Rational design of candidate compounds likely to be able to interact with GPR86 protein may be based upon structural studies of the molecular shapes of a polypeptide. One means for determining which sites interact with specific other proteins is a physical structure determination, e.g., X-ray crystallography or two-dimensional NMR techniques. These will provide guidance as to which amino acid residues form molecular contact regions. For a detailed description of protein structural determination, see, e.g., Blundell and Johnson (1976) *Protein Crystallography*, Academic Press, New York.

An alternative to rational design uses a screening procedure which involves in general allowing GPR86 to contact a candidate modulator and detecting an effect thereof. In general, such a method comprises producing appropriate cells which express the GPR86 receptor polypeptide on the surface thereof, optionally together with a partner protein, and contacting the GPR86 or the cell or both with a candidate modulator, and detecting a change in the intracellular level of a relevant molecule.

Molecules whose concentrations are affected by activity of GPCRs, in particular GPR86, and which may be used as markers for GPR86 activity, are known in the art. These are referred to for convenience as "GPCR sensitive markers". Examples of such GPCR sensitive markers include intracellular calcium levels, calcium flux, adenylate cyclase levels, and cyclic AMP levels. In a preferred embodiment, the GPCR sensitive marker comprises intracellular cyclic AMP (cAMP), and the screen includes detecting a change in the intracellular level of cyclic AMP.

In particularly preferred embodiments, GPR86 may be screened in the presence of a partner protein; such a partner protein may be co-expressed together with the GPR86 receptor polypeptide, preferably intracellularly. The partner protein may preferably comprise a G protein such as the GPR86 favoured G-protein, $G_i$ or a promiscuous stimulatory G-protein such as $G_{\alpha 16}$.

In screens which employ cells bearing GPR86 and the GPR86 favoured G-protein, $G_i$, agonists lower the level of intracellular cAMP concentration, while antagonists raise the intracellular cAMP concentration.

Where the screen employs GPR86 and a promiscuous stimulatory G-protein such as $G_{\alpha 16}$, agonists raise the level of intracellular cAMP concentration, while antagonists lower the intracellular cAMP concentration.

We therefore disclose a method for identifying an agonist of GPR86 when coupled to the GPR86 favoured G-protein, $G_i$, the method comprising contacting a cell which expresses GPR86 receptor with a candidate compound and determining whether the level of cyclic AMP (cAMP) in said cell is lowered as a result of said contacting. Alternatively, GPR86 may be co-expressed with a promiscuous stimulatory G-protein such as $G_{\alpha 16}$, and the method may comprise contacting a cell which expresses GPR86 and $G_{\alpha 16}$ with a candidate compound and determining whether the level of cyclic cAMP in said cell is raised as a result of said contacting.

We further disclose a method for identifying an antagonist of GPR86 when coupled to the GPR86 favoured G-protein, $G_i$, the method comprising contacting a cell which expresses GPR86 receptor with a candidate compound and determining whether the level of cyclic AMP (cAMP) in said cell is raised as a result of said contacting. Alternatively, if GPR86 is co-expressed with a promiscuous stimulatory G-protein such as $G_{\alpha 16}$, contacting a cell which expresses GPR86 and $G_{\alpha 16}$ with a candidate compound and determining whether the level of cyclic cAMP in said cell is lowered as a result of said contacting.

Cells which may be used for the screen may be of various types. Such cells include cells from animals, yeast, *Drosophila* or *E. coli*. Cells expressing the receptor (or cell membrane containing the expressed receptor) are then contacted with a test compound to observe binding, or stimulation or inhibition of a functional response. For example, *Xenopus* oocytes may be injected with GPR86 mRNA or polypeptide, and currents induced by exposure to test compounds measured by use of voltage clamps measured, as described in further detail elsewhere.

Furthermore, microphysiometric assays may be employed to assay GPR86 receptor activity. Activation of a wide variety of secondary messenger systems results in extrusion of small amounts of acid from a cell. The acid formed is largely as a result of the increased metabolic activity required to fuel the intracellular signalling process. The pH changes in the media surrounding the cell are very small but are detectable by, for example, the CYTOSENSOR microphysiometer (Molecular Devices Ltd., Menlo Park, Calif.). The CYTOSENSOR is thus capable of detecting the activation of a receptor which is coupled to an energy utilizing intracellular signaling pathway such as the G-protein coupled receptor described here.

Instead of testing each candidate compound individually with the GPR86 receptor, a library or bank of candidate ligands may advantageously be produced and screened. Thus, for example, a bank of over 200 putative receptor ligands has been assembled for screening. The bank comprises: transmitters, hormones and chemokines known to act via a human seven transmembrane (7TM) receptor, naturally occurring compounds which may be putative agonists for a human 7TM receptor, non-mammalian, biologically active peptides for which a mammalian counterpart has not yet been identified; and compounds not found in nature, but which activate 7TM receptors with unknown natural ligands. This bank is used to screen the receptor for known ligands, using both functional (i.e. calcium, cAMP, microphysiometer, oocyte electrophysiology, etc, see elsewhere) as well as binding assays as described in further detail elsewhere. However, a large number of mammalian receptors exist for which there remains, as yet, no cognate activating ligand (agonist) or deactivating ligand (antagonist). Thus, active ligands for these receptors may not be included within the ligands banks as identified to date. Accordingly, the GPR86 receptor is also functionally screened (using calcium, cAMP, microphysiometer, oocyte electrophysiology, etc., functional screens) against tissue extracts to identify natural ligands. Extracts that produce positive functional responses can be sequentially subfractionated, with the fractions being assayed as described here, until an activating ligand is isolated and identified.

7TM receptors which are expressed in HEK 293 cells have been shown to be coupled functionally to activation of PLC and calcium mobilization and/or cAMP stimulation or inhibition. One screening technique therefore includes the use of cells which express the GPR86 receptor (for example, transfected *Xenopus* oocytes, CHO or HEK293 cells) in a system which measures extracellular or intracellular pH or intracellular calcium changes caused by receptor activation. In this technique, compounds may be contacted with cells expressing the receptor polypeptide. A second messenger response, e.g., signal transduction, pH changes, or changes in calcium level, is then measured to determine whether the potential compound activates or inhibits the receptor.

In such experiments, basal calcium levels in the HEK 293 cells in receptor-transfected or vector control cells are observed to be in the normal, 100 nM to 200 nM, range. HEK 293 cells expressing GPR86 or recombinant GPR86 are loaded with fura 2 and in a single day more than 150 selected ligands or tissue/cell extracts are evaluated for agonist induced calcium mobilization. Similarly, HEK 293 cells expressing GPR86 or recombinant GPR86 are evaluated for the stimulation or inhibition of cAMP production using standard cAMP quantitation assays. Agonists presenting a calcium transient or cAMP fluctuation are tested in vector control cells to determine if the response is unique to the transfected cells expressing receptor.

Another method involves screening for receptor inhibitors by determining inhibition or stimulation of GPR86 receptor-mediated cAMP and/or adenylate cyclase accumulation. Such a method involves transfecting a eukaryotic cell with the receptor to express the receptor on the cell surface. The cell is then exposed to potential antagonists in the presence of the receptor. The amount of cAMP accumulation is then measured. If the potential antagonist binds the receptor, and thus inhibits receptor binding, the levels of receptor-mediated cAMP, or adenylate cyclase, activity will be reduced or increased.

Another method for detecting agonists or antagonists for the GPR86 receptor is the yeast based technology as described in U.S. Pat. No. 5,482,835, incorporated by reference herein.

Where the candidate compounds are proteins, in particular antibodies or peptides, libraries of candidate compounds may be screened using phage display techniques. Phage display is a protocol of molecular screening which utilises recombinant bacteriophage. The technology involves transforming bacteriophage with a gene that encodes one compound from the library of candidate compounds, such that each phage or phagemid expresses a particular candidate compound. The transformed bacteriophage (which preferably is tethered to a solid support) expresses the appropriate candidate compound and displays it on their phage coat. Specific candidate compounds which are capable of binding to a GPR86 polypeptide or peptide are enriched by selection strategies based on affinity interaction. The successful candidate agents are then characterised. Phage display has advantages over standard affinity ligand screening technologies. The phage surface displays the candidate agent in a three dimensional configuration, more closely resembling its naturally occurring conformation. This allows for more specific and higher affinity binding for screening purposes.

Another method of screening a library of compounds utilises eukaryotic or prokaryotic host cells which are stably transformed with recombinant DNA molecules expressing a library of compounds. Such cells, either in viable or fixed form, can be used for standard binding-partner assays. See also Parce et al. (1989) Science 246:243-247, and Owicki et al. (1990) Proc. Nat'l Acad. Sci. USA 87; 4007-4011, which describe sensitive methods to detect cellular responses. Competitive assays are particularly useful, where the cells expressing the library of compounds are contacted or incubated with a labelled antibody known to bind to a GPR86 polypeptide, such as $^{125}$I-antibody, and a test sample such as a candidate compound whose binding affinity to the binding composition is being measured. The bound and free labelled binding partners for the polypeptide are then separated to assess the degree of binding. The amount of test sample bound is inversely proportional to the amount of labelled antibody binding to the polypeptide.

Any one of numerous techniques can be used to separate bound from free binding partners to assess the degree of binding. This separation step could typically involve a procedure such as adhesion to filters followed by washing, adhesion to plastic following by washing, or centrifugation of the cell membranes.

Still another approach is to use solubilized, unpurified or solubilized purified polypeptide or peptides, for example extracted from transformed eukaryotic or prokaryotic host cells. This allows for a "molecular" binding assay with the advantages of increased specificity, the ability to automate, and high drug test throughput.

Another technique for candidate compound screening involves an approach which provides high throughput screening for new compounds having suitable binding affinity, e.g., to a GPR86 polypeptide, and is described in detail in International Patent application no. WO 84/03564 (Commonwealth Serum Labs), published on Sep. 13, 1984. First, large numbers of different small peptide test compounds are synthesized on a solid substrate, e.g., plastic pins or some other appropriate surface, see Fodor et al. (1991). Then all the pins are reacted with solubilized polypeptide and washed. The next step involves detecting bound polypeptide. Compounds which interact specifically with the polypeptide will thus be identified.

Ligand binding assays provide a direct method for ascertaining receptor pharmacology and are adaptable to a high throughput format. The purified ligand for a receptor may be radiolabeled to high specific activity (50-2000 Ci/mmol) for binding studies. A determination is then made that the process of radiolabeling does not diminish the activity of the ligand towards its receptor. Assay conditions for buffers, ions, pH and other modulators such as nucleotides are optimized to establish a workable signal to noise ratio for both membrane and whole cell receptor sources. For these assays, specific receptor binding is defined as total associated radioactivity minus the radioactivity measured in the presence of an excess of unlabeled competing ligand. Where possible, more than one competing ligand is used to define residual nonspecific binding.

The assays may simply test binding of a candidate compound wherein adherence to the cells bearing the receptor is detected by means of a label directly or indirectly associated with the candidate compound or in an assay involving competition with a labeled competitor. Further, these assays may test whether the candidate compound results in a signal generated by activation of the receptor, using detection systems appropriate to the cells bearing the receptor at their surfaces. Inhibitors of activation are generally assayed in the presence of a known agonist and the effect on activation by the agonist by the presence of the candidate compound is observed.

Further, the assays may simply comprise the steps of mixing a candidate compound with a solution containing a GPR86 polypeptide to form a mixture, measuring GPR86 activity in the mixture, and comparing the GPR86 activity of the mixture to a standard.

The GPR86 cDNA, protein and antibodies to the protein may also be used to configure assays for detecting the effect of added compounds on the production of GPR86 mRNA and protein in cells. For example, an ELISA may be constructed for measuring secreted or cell associated levels of GPR86 protein using monoclonal and polyclonal antibodies by standard methods known in the art, and this can be used to discover agents which may inhibit or enhance the production of GPR86 (also called antagonist or agonist, respectively) from suitably manipulated cells or tissues. Standard methods for conducting screening assays are well understood in the art.

Examples of potential GPR86 antagonists include antibodies or, in some cases, nucleotides and their analogues, including purines and purine analogues, oligonucleotides or proteins which are closely related to the ligand of the GPR86, e.g., a fragment of the ligand, or small molecules which bind to the receptor but do not elicit a response, so that the activity of the receptor is prevented.

We therefore also provide a compound capable of binding specifically to a GPR86 polypeptide and/or peptide.

The term "compound" refers to a chemical compound (naturally occurring or synthesised), such as a biological macromolecule (e.g., nucleic acid, protein, non-peptide, or organic molecule), or an extract made from biological materials such as bacteria, plants, fungi, or animal (particularly mammalian) cells or tissues, or even an inorganic element or molecule. Preferably the compound is an antibody.

The materials necessary for such screening to be conducted may be packaged into a screening kit. Such a screening kit is useful for identifying agonists, antagonists, ligands, receptors, substrates, enzymes, etc. for GPR86 polypeptides or compounds which decrease or enhance the production of GPR86 polypeptides. The screening kit comprises: (a) a GPR86 polypeptide; (b) a recombinant cell expressing a GPR86 polypeptide, (c) a cell membrane expressing a GPR86 polypeptide, or (d) antibody to a GPR86 polypeptide. The screening kit may optionally comprise instructions for use.

Transgenic Animals

We further disclose transgenic animals capable of expressing natural or recombinant GPR86, or a homologue, variant or derivative, at normal, elevated or reduced levels compared to the normal expression level. Preferably, such a transgenic animal is a non-human mammal, such as a pig, a sheep or a rodent. Most preferably the transgenic animal is a mouse or a rat.

We disclose transgenic animals in which all or a portion of the native GPR86 gene is replaced by GPR86 sequences from another organism. Preferably this organism is another species, most preferably a human. In highly preferred embodiments, we disclose a mouse which has substantially its entire GPR86 gene replaced with a human GPR86 gene. Such transgenic animals, as well as animals which are wild type for GPR86, may be used for screening agonists and/or antagonists of GPR86.

For example, such assays may involve exposing the wild type or transgenic animal, or a portion thereof, preferably a cell, tissue or organ of the transgenic animal, to a candidate substance, and assaying for a GPR86 associated phenotype such as pain or inflammation. Cell-based screens employing cells derived from the relevant animal and assaying for effects on intracellular cyclic AMP concentration may also be conducted.

We further disclose transgenic animals comprising functionally disrupted GPR86 gene, in which any one or more of the functions of GPR86 as disclosed in this document is partially or totally abolished. Included are transgenic animals ("GPR86 knockout"s) which do not express functional GPR86 as a result of one or more loss of function mutations, including a deletion, of the GPR86 gene.

Transgenic animals lacking functional GPR86 (GPR86 knockouts) display an altered susceptibility to pain when compared to a wild-type animal. Specifically, GPR86 knockouts are less sensitive to pain. Furthermore, GPR86 knockouts animals exhibit an altered susceptibility to inflammatory pain, particularly decreased susceptibility to inflammatory pain.

Also included are partial loss-of-function mutants, e.g., an incomplete knockout, which may for example have deletions in selected portions of the GPR86 gene. Such animals may be generated by selectively replacing or deleting relevant portions of the GPR86 sequence, for example, functionally important protein domains.

Such complete or partial loss of function mutants are useful as models for GPR86 related diseases, particularly pain or inflammatory disease. An animal displaying partial-loss-of-function may be exposed to a candidate substance to identify substances which enhance the phenotype, that is to say, to increase (in the case of GPR86) the reduced sensitivity to pain phenotype observed. Other parameters such as change in intracellular cyclic AMP levels may also be detected using the methods identified elsewhere in this document.

Partial and complete knockouts may also be used to identify selective agonists and/or antagonists of GPR86. For example, an agonist and/or antagonist may be administered to a wild type and a GPR86 deficient animal (knockout). A selective agonist or antagonist of GPR86 will be seen to have an effect on the wild type animal but not in the GPR86 deficient animal. In detail, a specific assay is designed to evaluate a potential drug (a candidate ligand or compound) to determine if it produces side effects in the absence of GPR86. This may be accomplished by administering the drug to a transgenic animal as discussed above, and then assaying the animal for a particular response. Analogous cell-based methods employing cells derived from the relevant animal and assaying for effects on intracellular cyclic AMP concentration may also be conducted. Such animals may also be used to test for efficacy of drugs identified by the screens described in this document.

In another embodiment, a transgenic animal having a partial loss-of-function phenotype is employed for screening. In such an embodiment, the screen may involve assaying for partial or complete restoration or reversion to the wild type phenotype. Cell-based screens employing cells derived from the relevant animal and assaying for effects on intracellular cyclic AMP concentration may also be conducted. A candidate compound which is found to be capable of such can be regarded as a GPR86 agonist or analogue. Such agonists may be used for example to restore or increase sensitivity to stimuli, for example pain.

In preferred embodiments, the transgenic GPR86 animals, particularly GPR86 knockouts (complete loss of function), display the phenotypes set out in the Examples, preferably as measured by the tests set out therein. Thus, the GPR86 animals, particularly GPR86 knockouts, preferably display any one or more of the following: lower sensitivity to pain (hypoalgesia), lower susceptibility to inflammation.

In highly preferred embodiments, the transgenic GPR86 animals, particularly GPR86 knockouts, display at least 10%, preferably at least 20%, more preferably at least 30%, 40%, 50%, 60%, 70%, 80%, 90%, or 100% higher or lower (as the case may be) of the measured parameter as compared to the corresponding wild-type mice. Thus, for example, GPR86 knockouts have an increased pain threshold in response to the Tail Flick test set out in the examples, of 1 second, 2 seconds, 5 seconds, 10 seconds, 30 seconds or more, or 5%, 10%, 20%, 50% or more when compared to wild type mice.

It will be evident that the phenotypes now disclosed for GPR86 deficient transgenic animals may be usefully employed in a screen using wild type animals, to detect compounds which cause similar effects to loss-of-function of GPR86. In other words, a wild type animal may be exposed to a candidate compound, and a change in a relevant GPR86 phenotype observed, such reduction in sensitivity to pain, etc, to identify modulators of GPR86 function, particularly antagonists. Cellular phenotypes such as change in intracellular cyclic AMP levels may also be detected using the methods identified elsewhere in this document.

A compound identified by such a screen could be used as an antagonist of GPR86, e.g., as an analgesic particularly for the treatment or relief of a GPR86 associated disease.

The screens described above may involve observation of any suitable parameter, such as a behavioural, physiological or biochemical response. Preferred responses include one or more of the following: changes to disease resistance; altered inflammatory responses; altered tumour susceptibility: a change in blood pressure; neovascularization; a change in eating behavior; a change in body weight; a change in bone density; a change in body temperature; insulin secretion; gonadotropin secretion; nasal and bronchial secretion; vasoconstriction; loss of memory; anxiety; hyporeflexia or hyperreflexia; pain or stress responses.

Tissues derived from the GPR86 knockout animals may be used in receptor binding assays to determine whether the potential drug (a candidate ligand or compound) binds to the GPR86 receptor. Such assays can be conducted by obtaining a first receptor preparation from the transgenic animal engineered to be deficient in GPR86 receptor production and a second receptor preparation from a source known to bind any identified GPR86 ligands or compounds. In general, the first and second receptor preparations will be similar in all respects except for the source from which they are obtained. For example, if brain tissue from a transgenic animal (such as described above and below) is used in an assay, comparable brain tissue from a normal (wild type) animal is used as the source of the second receptor preparation. Each of the receptor preparations is incubated with a ligand known to bind to GPR86 receptors, both alone and in the presence of the candidate ligand or compound. Preferably, the candidate ligand or compound will be examined at several different concentrations.

The extent to which binding by the known ligand is displaced by the test compound is determined for both the first and second receptor preparations. Tissues derived from transgenic animals may be used in assays directly or the tissues may be processed to isolate membranes or membrane proteins, which are themselves used in the assays. A preferred transgenic animal is the mouse. The ligand may be labeled using any means compatible with binding assays. This would include, without limitation, radioactive, enzymatic, fluorescent or chemiluminescent labeling (as well as other labelling techniques as described in further detail above).

Furthermore, antagonists of GPR86 receptor may be identified by administering candidate compounds, etc, to wild type animals expressing functional GPR86, and animals identified which exhibit any of the phenotypic characteristics associated with reduced or abolished expression of GPR86 receptor function.

Detailed methods for generating non-human transgenic animal are described in further detail below. Transgenic gene constructs can be introduced into the germ line of an animal to make a transgenic mammal. For example, one or several copies of the construct may be incorporated into the genome of a mammalian embryo by standard transgenic techniques.

In an exemplary embodiment, the transgenic non-human animals described here are produced by introducing transgenes into the germline of the non-human animal. Embryonal target cells at various developmental stages can be used to introduce transgenes. Different methods are used depending on the stage of development of the embryonal target cell. The specific line(s) of animals used for this purpose are selected for general good health, good embryo yields, good pronuclear visibility in the embryo, and good reproductive fitness. In addition, the haplotype is a significant factor.

Introduction of the transgene into the embryo can be accomplished by any means known in the art such as, for example, microinjection, electroporation, or lipofection. For example, the GPR86 receptor transgene can be introduced into a mammal by microinjection of the construct into the pronuclei of the fertilized mammalian egg(s) to cause one or more copies of the construct to be retained in the cells of the developing mammal(s). Following introduction of the transgene construct into the fertilized egg, the egg may be incubated in vitro for varying amounts of time, or reimplanted into the surrogate host, or both. In vitro incubation to maturity is within the scope of this document. One common method in to incubate the embryos in vitro for about 1-7 days, depending on the species, and then reimplant them into the surrogate host.

The progeny of the transgenically manipulated embryos can be tested for the presence of the construct by Southern blot analysis of the segment of tissue. If one or more copies of the exogenous cloned construct remains stably integrated into the genome of such transgenic embryos, it is possible to establish permanent transgenic mammal lines carrying the transgenically added construct.

The litters of transgenically altered mammals can be assayed after birth for the incorporation of the construct into the genome of the offspring. Preferably, this assay is accomplished by hybridizing a probe corresponding to the DNA sequence coding for the desired recombinant protein product or a segment thereof onto chromosomal material from the progeny. Those mammalian progeny found to contain at least one copy of the construct in their genome are grown to maturity.

For the purposes of this document, a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000-20,000 copies of the transgene construct, in order to insure that one copy is functional. There will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance our description will include exogenous genetic material. As set out above, the exogenous genetic material will, in certain embodiments, be a DNA sequence which results in the production of a GPR86 receptor. Further, in such embodiments the sequence will be attached to a transcriptional control element, e.g., a promoter, which preferably allows the expression of the transgene product in a specific type of cell.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) PNAS 73:1260-1264). Efficient infection of the blastomeres is obtained by enzymatic treatment to remove the zona pellucida (Manipulating the Mouse Embryo, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) PNAS 82:6927-6931; Van der Putten et al. (1985) PNAS 82:6148-6152). Transfection is easily and efficiently obtained by culturing the blastomeres on a monolayer of virus-producing cells (Van der Putten, supra; Stewart et al. (1987) EMBO J. 6:383-388). Alternatively, infection can be performed at a later stage. Virus or virus-producing cells can be injected into the blastocoele (Jahner et al. (1982) Nature 298:623-628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) Nature 292:154-156; Bradley et al. (1984) Nature 309:255-258; Gossler et al. (1986) PNAS 83: 9065-9069; and Robertson et al. (1986) Nature 322:445-448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) Science 240:1468-1474.

We also provide non-human transgenic animals, where the transgenic animal is characterized by having an altered GPR86 gene, preferably as described above, as models for GPR86 receptor function. Alterations to the gene include deletions or other loss of function mutations, introduction of an exogenous gene having a nucleotide sequence with targeted or random mutations, introduction of an exogenous gene from another species, or a combination thereof. The transgenic animals may be either homozygous or heterozygous for the alteration. The animals and cells derived there from are useful for screening biologically active agents that may modulate GPR86 receptor function. The screening methods are of particular use for determining the specificity and action of potential therapies for pain and inflammatory disorders such as osteoarthritis, rheumatoid arthritis, asthma, irritable bowel syndrome and allergies. The animals are useful as a model to investigate the role of GPR86 receptors in normal brain, heart, spleen and liver function.

Another aspect pertains to a transgenic nonhuman animal having a functionally disrupted endogenous GPR86 gene but which also carries in its genome, and expresses, a transgene encoding a heterologous GPR86 protein (i.e., a GPR86 from another species). Preferably, the animal is a mouse and the heterologous GPR86 is a human GPR86. An animal, or cell lines derived from such an animal, which has been reconstituted with human GPR86, can be used to identify agents that inhibit human GPR86 in vivo and in vitro. For example, a stimulus that induces signalling through human GPR86 can be administered to the animal, or cell line, in the presence and absence of an agent to be tested and the response in the animal, or cell line, can be measured. An agent that inhibits human GPR86 in vivo or in vitro can be identified based upon a decreased response in the presence of the agent compared to the response in the absence of the agent.

We also provide for a GPR86 deficient transgenic non-human animal (a "GPR86 knock-out"). Such an animal is one which expresses lowered or no GPR86 activity, preferably as a result of an endogenous GPR86 genomic sequence being disrupted or deleted. Preferably, such an animal expresses no GPCR activity. More preferably, the animal expresses no activity of the GPR86 shown as SEQ ID NO: 3 or SEQ ID NO: 5. GPR86 knock-outs may be generated by various means known in the art, as described in further detail below.

This document also pertains to a nucleic acid construct for functionally disrupting a GPR86 gene in a host cell. The nucleic acid construct comprises: a) a non-homologous replacement portion; b) a first homology region located upstream of the non-homologous replacement portion, the first homology region having a nucleotide sequence with substantial identity to a first GPR86 gene sequence, and c) a second homology region located downstream of the non-homologous replacement portion, the second homology region having a nucleotide sequence with substantial identity to a second GPR86 gene sequence, the second GPR86 gene sequence having a location downstream of the first GPR86 gene sequence in a naturally occurring endogenous GPR86 gene. Additionally, the first and second homology regions are of sufficient length for homologous recombination between the nucleic acid construct and an endogenous GPR86 gene in a host cell when the nucleic acid molecule is introduced into the host cell. In a preferred embodiment, the non-homologous replacement portion comprises an expression reporter, preferably including lacZ and a positive selection expression cassette, preferably including a neomycin phosphotransferase gene operatively linked to a regulatory element(s).

Preferably, the first and second GPR86 gene sequences are derived from SEQ ID NO: 1, SEQ ID NO: 2 or SEQ ID NO: 4, or a homologue, variant or derivative thereof.

Another aspect pertains to recombinant vectors into which the nucleic acid construct described here has been incorporated. Yet another aspect pertains to host cells into which the nucleic acid construct described here has been introduced to thereby allow homologous recombination between the nucleic acid construct and an endogenous GPR86 gene of the host cell, resulting in functional disruption of the endogenous GPR86 gene. The host cell can be a mammalian cell that normally expresses GPR86 from the liver, brain, spleen or heart, or a pluripotent cell, such as a mouse embryonic stem cell. Further development of an embryonic stem cell into which the nucleic acid construct has been introduced and homologously recombined with the endogenous GPR86 gene produces a transgenic nonhuman animal having cells that are descendant from the embryonic stem cell and thus carry the GPR86 gene disruption in their genome. Animals that carry the GPR86 gene disruption in their germline can then be selected and bred to produce animals having the GPR86 gene disruption in all somatic and germ cells. Such mice can then be bred to homozygosity for the GPR86 gene disruption.

Antibodies

For the purposes of this document, the term "antibody", unless specified to the contrary, includes but is not limited to, polyclonal, monoclonal, chimeric, single chain, Fab fragments and fragments produced by a Fab expression library. Such fragments include fragments of whole antibodies which retain their binding activity for a target substance, Fv, F(ab') and F(ab')$_2$ fragments, as well as single chain antibodies (scFv), fusion proteins and other synthetic proteins which comprise the antigen-binding site of the antibody. The antibodies and fragments thereof may be humanised antibodies, for example as described in EP-A-239400. Furthermore, antibodies with fully human variable regions (or their fragments), for example, as described in U.S. Pat. Nos. 5,545,807 and 6,075,181 may also be used. Neutralizing antibodies, i.e., those which inhibit biological activity of the substance amino acid sequences, are especially preferred for diagnostics and therapeutics.

Antibodies may be produced by standard techniques, such as by immunisation or by using a phage display library.

A GPR86 polypeptide or peptide may be used to develop an antibody by known techniques. Such an antibody may be capable of binding specifically to the GPR86 protein or homologue, fragment, etc.

If polyclonal antibodies are desired, a selected mammal (e.g., mouse, rabbit, goat, horse, etc.) may be immunised with an immunogenic composition comprising a GPR86 polypeptide or peptide. Depending on the host species, various adjuvants may be used to increase immunological response. Such adjuvants include, but are not limited to, Freund's, mineral gels such as aluminium hydroxide, and surface active substances such as lysolecithin, pluronic polyols, polyanions, peptides, oil emulsions, keyhole limpet hemocyanin, and dinitrophenol. BCG (*Bacilli Calmette-Guerin*) and *Corynebacterium parvum* are potentially useful human adjuvants which may be employed if purified the substance amino acid sequence is administered to immunologically compromised individuals for the purpose of stimulating systemic defence.

Serum from the immunised animal is collected and treated according to known procedures. If serum containing polyclonal antibodies to an epitope obtainable from a GPR86 polypeptide contains antibodies to other antigens, the polyclonal antibodies can be purified by immunoaffinity chromatography. Techniques for producing and processing polyclonal antisera are known in the art. In order that such antibodies may be made, we further provide GPR86 amino acid sequences or fragments thereof haptenised to another amino acid sequence for use as immunogens in animals or humans.

Monoclonal antibodies directed against epitopes obtainable from a GPR86 polypeptide or peptide can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced against orbit epitopes can be screened for various properties; i.e., for isotype and epitope affinity.

Monoclonal antibodies may be prepared using any technique which provides for the production of antibody molecules by continuous cell lines in culture. These include, but are not limited to, the hybridoma technique originally described by Koehler and Milstein (1975 Nature 256:495-497), the trioma technique, the human B-cell hybridoma technique (Kosbor et al (1983) Immunol Today 4:72; Cote et al (1983) Proc Natl Acad Sci 80:2026-2030) and the EBV-hybridoma technique (Cole et al., *Monoclonal Antibodies and Cancer Therapy*, pp. 77-96, Alan R. Liss, Inc., 1985).

In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851-6855; Neuberger et al (1984) Nature 312:604-608; Takeda et al (1985) Nature 314:452-454). Alternatively, techniques described for the production of single chain antibodies (U.S. Pat. No. 4,946,779) can be adapted to produce the substance specific single chain antibodies.

Antibodies, both monoclonal and polyclonal, which are directed against epitopes obtainable from a GPR86 polypeptide or peptide are particularly useful in diagnosis, and those which are neutralising are useful in passive immunotherapy. Monoclonal antibodies, in particular, may be used to raise anti-idiotype antibodies. Anti-idiotype antibodies are immunoglobulins which carry an "internal image" of the substance and/or agent against which protection is desired. Techniques for raising anti-idiotype antibodies are known in the art. These anti-idiotype antibodies may also be useful in therapy.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833-3837), and Winter G and Milstein C (1991, Nature 349:293-299).

Antibody fragments which contain specific binding sites for the polypeptide or peptide may also be generated. For example, such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse W D et al (1989) Science 256:1275-128 1).

Techniques for the production of single chain antibodies (U.S. Pat. No. 4,946,778) can also be adapted to produce single chain antibodies to GPR86 polypeptides. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against GPR86 polypeptides may also be employed to treat pain and inflammatory disorders such as osteoarthritis, rheumatoid arthritis, asthma, irritable bowel syndrome and allergies.

Diagnostic Assays

We further describe the use of GPR86 polynucleotides and polypeptides (as well as homologues, variants and derivatives thereof) for use in diagnosis as diagnostic reagents or in genetic analysis. Nucleic acids complementary to or capable of hybridising to GPR86 nucleic acids (including homologues, variants and derivatives), as well as antibodies against GPR86 polypeptides are also useful in such assays.

Detection of a mutated form of the GPR86 gene associated with a dysfunction will provide a diagnostic tool that can add to or define a diagnosis of a disease or susceptibility to a disease which results from under-expression, over-expression or altered expression of GPR86. Individuals carrying mutations in the GPR86 gene (including control sequences) may be detected at the DNA level by a variety of techniques.

For example, DNA may be isolated from a patient and the DNA polymorphism pattern of GPR86 determined. The identified pattern is compared to controls of patients known to be suffering from a disease associated with over-, under- or abnormal expression of GPR86. Patients expressing a genetic polymorphism pattern associated with GPR86 associated disease may then be identified. Genetic analysis of the GPR86 gene may be conducted by any technique known in the art. For example, individuals may be screened by determining DNA sequence of a GPR86 allele, by RFLP or SNP analysis, etc. Patients may be identified as having a genetic predisposition for a disease associated with the over-, under-, or abnormal expression of GPR86 by detecting the presence of a DNA polymorphism in the gene sequence for GPR86 or any sequence controlling its expression.

Patients so identified can then be treated to prevent the occurrence of GPR86 associated disease, or more aggressively in the early stages of GPR86 associated disease to prevent the further occurrence or development of the disease. GPR86 associated diseases include dopamine related diseases, such as Parkinson's disease, cardiac disease such as supraventricular or ventricular arrhythmias, hypotension, nausea, Tourette syndrome, stress and pain.

We further disclose a kit for the identification of a patient's genetic polymorphism pattern associated with GPR86 associated disease. The kit includes DNA sample collecting means and means for determining a genetic polymorphism pattern, which is then compared to control samples to determine a patient's susceptibility to GPR86 associated disease. Kits for diagnosis of a GPR86 associated disease comprising GPR86 polypeptide and/or an antibody against such a polypeptide (or fragment of it) are also provided.

Nucleic acids for diagnosis may be obtained from a subject's cells, such as from blood, urine, saliva, tissue biopsy or autopsy material. In a preferred embodiment, the DNA is obtained from blood cells obtained from a finger prick of the patient with the blood collected on absorbent paper. In a further preferred embodiment, the blood will be collected on an AmpliCard™ (University of Sheffield, Department of Medicine and Pharmacology, Royal Hallamshire Hospital, Sheffield, England S10 2JF).

The DNA may be used directly for detection or may be amplified enzymatically by using PCR or other amplification techniques prior to analysis. Oligonucleotide DNA primers that target the specific polymorphic DNA region within the genes of interest may be prepared so that in the PCR reaction amplification of the target sequences is achieved. RNA or cDNA may also be used as templates in similar fashion. The amplified DNA sequences from the template DNA may then be analyzed using restriction enzymes to determine the genetic polymorphisms present in the amplified sequences and thereby provide a genetic polymorphism profile of the patient. Restriction fragments lengths may be identified by gel analysis. Alternatively, or in conjunction, techniques such as SNP (single nucleotide polymorphisms) analysis may be employed.

Deletions and insertions can be detected by a change in size of the amplified product in comparison to the normal genotype. Point mutations can be identified by hybridizing amplified DNA to labeled GPR86 nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al, Science (1985) 230:1242. Sequence changes at specific locations may also be revealed by nuclease protection assays, such as RNase and S1 protection or the chemical cleavage method. See Cotton et al., *Proc Natl Acad Sci USA* (1985) 85: 4397-4401. In another embodiment, an array of oligonucleotides probes comprising the GPR86 nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See for example: M. Chee et al., *Science*, Vol 274, pp 610-613 (1996)).

Single strand conformation polymorphism (SSCP) may be used to detect differences in electrophoretic mobility between mutant and wild type nucleic acids (Orita et al. (1989) *Proc Natl. Acad. Sci. USA:* 86:2766, see also Cotton (1993) *Mutat Res* 285:125-144, and Hayashi (1992) *Genet Anal Tech Appl* 9:73-79). Single-stranded DNA fragments of sample and control GPR86 nucleic acids may be denatured and allowed to renature. The secondary structure of single-stranded nucleic acids varies according to sequence, the resulting alteration in electrophoretic mobility enables the detection of even a single base change. The DNA fragments may be labelled or detected with labelled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet* 7:5).

The diagnostic assays offer a process for diagnosing or determining a susceptibility to infections through detection of mutation in the GPR86 gene by the methods described.

The presence of GPR86 polypeptides and nucleic acids may be detected in a sample. Thus, infections and diseases as listed above can be diagnosed by methods comprising determining from a sample derived from a subject an abnormally decreased or increased level of the GPR86 polypeptide or GPR86 mRNA. The sample may comprise a cell or tissue sample from an organism suffering or suspected to be suffering from a disease associated with increased, reduced or otherwise abnormal GPR86 expression, including spatial or temporal changes in level or pattern of expression. The level or pattern of expression of GPR86 in an organism suffering from or suspected to be suffering from such a disease may be usefully compared with the level or pattern of expression in a normal organism as a means of diagnosis of disease.

In general therefore, we disclose a method of detecting the presence of a nucleic acid comprising a GPR86 nucleic acid in a sample, by contacting the sample with at least one nucleic acid probe which is specific for said nucleic acid and monitoring said sample for the presence of the nucleic acid. For example, the nucleic acid probe may specifically bind to the GPR86 nucleic acid, or a portion of it, and binding between the two detected, the presence of the complex itself may also be detected. Furthermore, we disclose a method of detecting the presence of a GPR86 polypeptide by contacting a cell sample with an antibody capable of binding the polypeptide and monitoring said sample for the presence of the polypeptide. This may conveniently be achieved by monitoring the presence of a complex formed between the antibody and the polypeptide, or monitoring the binding between the polypeptide and the antibody. Methods of detecting binding between two entities are known in the art, and include FRET (fluorescence resonance energy transfer), surface plasmon resonance, etc.

Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as a GPR86, in a sample derived from a host are well-known to those of skill in the art. Such assay methods include radioimmunoassays, competitive-binding assays, Western Blot analysis and ELISA assays.

This disclosure also relates to a diagnostic kit for a disease or susceptibility to a disease (including an infection), for example, dopamine related diseases, such as Parkinson's disease, cardiac disease such as supraventricular or ventricular arrhythmias, hypotension, nausea, Tourette syndrome, stress and pain. The diagnostic kit comprises a GPR86 polynucleotide or a fragment thereof, a complementary nucleotide sequence, a GPR86 polypeptide or a fragment thereof, or an antibody to a GPR86 polypeptide.

Chromosome Assays

The GPR86 nucleotide sequences are also valuable for chromosome identification. The sequence is specifically targeted to and can hybridize with a particular location on an individual human chromosome. As described above, human GPR86 is found to map to Homo sapiens chromosome 3q24.

The mapping of relevant sequences to chromosomes is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian heritance in Man (available on line through Johns Hopkins University Welch Medical Library). The relationship between genes and diseases that have been mapped to the same chromosomal region are then identified through linkage analysis (coinheritance of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease.

Prophylactic and Therapeutic Methods

We further provide methods of treating an abnormal conditions related to both an excess of and insufficient amounts of GPR86 activity.

If the activity of GPR86 is in excess, several approaches are available. One approach comprises administering to a subject an inhibitor compound (antagonist) as hereinabove described along with a pharmaceutically acceptable carrier in an amount effective to inhibit activation by blocking binding of ligands to the GPR86, or by inhibiting a second signal, and thereby alleviating the abnormal condition.

In another approach, soluble forms of GPR86 polypeptides still capable of binding the ligand in competition with endogenous GPR86 may be administered. Typical embodiments of such competitors comprise fragments of the GPR86 polypeptide.

In still another approach, expression of the gene encoding endogenous GPR86 can be inhibited using expression blocking techniques. Known such techniques involve the use of antisense sequences, either internally generated or separately administered. See, for example, O'Connor, *J Neurochem* (1991) 56:560 in Oligodeoxynucleotides as Antisense Inhibitors of Gene Expression, CRC Press, Boca Raton, Fla. (1988). Alternatively, oligonucleotides which form triple helices with the gene can be supplied. See, for example, Lee et al., *Nucleic Acids Res* (1979) 6:3073, Cooney et al., *Science* (1988) 241: 456, Dervan et al., *Science* (1991) 251:1360. These oligomers can be administered per se or the relevant oligomers can be expressed in vivo.

For treating abnormal conditions related to an under-expression of GPR86 and its activity, several approaches are also available. One approach comprises administering to a subject a therapeutically effective amount of a compound which activates GPR86, i.e., an agonist as described above, in combination with a pharmaceutically acceptable carrier, to thereby alleviate the abnormal condition. Alternatively, gene therapy may be employed to effect the endogenous production of GPR86 by the relevant cells in the subject. For example, a GPR86 polynucleotide may be engineered for expression in a replication defective retroviral vector, as discussed above. The retroviral expression construct may then be isolated and introduced into a packaging cell transduced with a retroviral plasmid vector containing RNA encoding a GPR86 polypeptide such that the packaging cell now produces infectious viral particles containing the gene of interest. These producer cells may be administered to a subject for engineering cells in vivo and expression of the polypeptide in vivo. For overview of gene therapy, see Chapter 20, Gene Therapy and other Molecular Genetic-based Therapeutic Approaches, (and references cited therein) in Human Molecular Genetics, T Strachan and A P Read, BIOS Scientific Publishers Ltd (1996).

Formulation and Administration

Peptides, such as the soluble form of GPR86 polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. This document also relates to pharmaceutical packs and kits comprising one or more containers filled with one or more of the ingredients of the aforementioned compositions.

The GPR86 polypeptides and other compounds may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include transmucosal and transdermal administration using penetrants such as bile salts or fusidic acids or other detergents. In addition, if properly formulated in enteric or encapsulated formulations, oral administration may also be possible. Administration of these compounds may also be topical and/or localize, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1-100 μg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

Pharmaceutical Compositions

We also provide a pharmaceutical composition comprising administering a therapeutically effective amount of the GPR86 polypeptide, polynucleotide, peptide, vector or antibody thereof described here and optionally a pharmaceutically acceptable carrier, diluent or excipients (including combinations thereof).

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of described here may be formulated to be delivered using a mini-pump or by a mucosal route, for example, as a nasal spray or aerosol for inhalation or ingestible solution, or parenterally in which the composition is formulated by an injectable form, for delivery, by, for example, an intravenous, intramuscular or subcutaneous route. Alternatively, the formulation may be designed to be delivered by both routes.

Where the agent is to be delivered mucosally through the gastrointestinal mucosa, it should be able to remain stable during transit though the gastrointestinal tract, for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Vaccines

Another embodiment relates to a method for inducing an immunological response in a mammal which comprises inoculating the mammal with the GPR86 polypeptide, or a fragment thereof, adequate to produce antibody and/or T cell immune response to protect said animal from GPR86 associated diseases.

Yet another embodiment relates to a method of inducing immunological response in a mammal which comprises delivering a GPR86 polypeptide via a vector directing expression of a GPR86 polynucleotide in vivo in order to induce such an immunological response to produce antibody to protect said animal from diseases.

A further embodiment relates to an immunological/vaccine formulation (composition) which, when introduced into a mammalian host, induces an immunological response in that mammal to a GPR86 polypeptide wherein the composition comprises a GPR86 polypeptide or GPR86 gene. The vaccine formulation may further comprise a suitable carrier.

Since the GPR86 polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Vaccines may be prepared from one or more GPR86 polypeptides or peptides.

The preparation of vaccines which contain an immunogenic polypeptide(s) or peptide(s) as active ingredient(s), is known to one skilled in the art. Typically, such vaccines are prepared as injectables, either as liquid solutions or suspensions; solid forms suitable for solution in, or suspension in, liquid prior to injection may also be prepared. The preparation may also be emulsified, or the protein encapsulated in liposomes. The active immunogenic ingredients are often mixed with excipients which are pharmaceutically acceptable and compatible with the active ingredient. Suitable excipients are, for example, water, saline, dextrose, glycerol, ethanol, or the like and combinations thereof.

In addition, if desired, the vaccine may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion.

Further examples of adjuvants and other agents include aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid X, *Corynebacterium parvum* (*Propionobacterium acnes*), *Bordetella pertussis*, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.).

Typically, adjuvants such as Amphigen (oil-in-water), Alhydrogel (aluminum hydroxide), or a mixture of Amphigen and Alhydrogel are used. Only aluminum hydroxide is approved for human use.

The proportion of immunogen and adjuvant can be varied over a broad range so long as both are present in effective amounts. For example, aluminum hydroxide can be present in an amount of about 0.5% of the vaccine mixture ($Al_2O_3$ basis). Conveniently, the vaccines are formulated to contain a final concentration of immunogen in the range of from 0.2 to 200 µg/ml, preferably 5 to 50 µg/ml, most preferably 15 µg/ml.

After formulation, the vaccine may be incorporated into a sterile container which is then sealed and stored at a low temperature, for example 4° C., or it may be freeze-dried. Lyophilisation permits long-term storage in a stabilised form.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides, such suppositories may be formed from mixtures containing the active ingredient in the range of 0.5% to 10%, preferably 1% to 2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the vaccine composition is lyophilised, the lyophilised material may be reconstituted prior to administration, e.g. as a suspension. Reconstitution is preferably effected in buffer Capsules, tablets and pills for oral administration to a patient may be provided with an enteric coating comprising, for example, Eudragit "S", Eudragit "L", cellulose acetate, cellulose acetate phthalate or hydroxypropylmethyl cellulose.

The GPR86 polypeptides may be formulated into the vaccine as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric and maleic. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine and procaine.

Administration

Typically, a physician will determine the actual dosage which will be most suitable for an individual subject and it will vary with the age, weight and response of the particular patient. The dosages below are exemplary of the average case. There can, of course, be individual instances where higher or lower dosage ranges are merited.

The pharmaceutical and vaccine compositions described here may be administered by direct injection. The composition may be formulated for parenteral, mucosal, intramuscular, intravenous, subcutaneous, intraocular or transdermal administration. Typically, each protein may be administered at a dose of from 0.01 to 30 mg/kg body weight, preferably from 0.1 to 10 mg/kg, more preferably from 0.1 to 1 mg/kg body weight.

The term "administered" includes delivery by viral or non-viral techniques. Viral delivery mechanisms include but are not limited to adenoviral vectors, adeno-associated viral (AAV) vectors, herpes viral vectors, retroviral vectors, lentiviral vectors, and baculoviral vectors. Non-viral delivery mechanisms include lipid mediated transfection, liposomes, immunoliposomes, lipofectin, cationic facial amphiphiles (CFAs) and combinations thereof. The routes for such delivery mechanisms include but are not limited to mucosal, nasal, oral, parenteral, gastrointestinal, topical, or sublingual routes.

The term "administered" includes but is not limited to delivery by a mucosal route, for example, as a nasal spray or aerosol for inhalation or as an ingestible solution; a parenteral route where delivery is by an injectable form, such as, for example, an intravenous, intramuscular or subcutaneous route.

The term "co-administered" means that the site and time of administration of each of for example, the GPR86 polypeptide and an additional entity such as adjuvant are such that the necessary modulation of the immune system is achieved. Thus, whilst the polypeptide and the adjuvant may be administered at the same moment in time and at the same site, there may be advantages in administering the polypeptide at a different time and to a different site from the adjuvant. The polypeptide and adjuvant may even be delivered in the same delivery vehicle—and the polypeptide and the antigen may be coupled and/or uncoupled and/or genetically coupled and/or uncoupled.

The GPR86 polypeptide, polynucleotide, peptide, nucleotide or antibody thereof and optionally an adjuvant may be administered separately or co-administered to the host subject as a single dose or in multiple doses.

The vaccine composition and pharmaceutical compositions described here may be administered by a number of different routes such as injection (which includes parenteral, subcutaneous and intramuscular injection) intranasal, mucosal, oral, intra-vaginal, urethral or ocular administration.

The vaccines and pharmaceutical compositions described here may be conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, may be 1% to 2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the vaccine composition is lyophilised, the lyophilised material may be reconstituted prior to administration, e.g. as a suspension. Reconstitution is preferably effected in buffer.

Further Aspects

Further aspects and embodiments of the invention are now set out in the following numbered Paragraphs; it is to be understood that the invention encompasses these aspects:

Paragraph 1. A GPR86 polypeptide comprising the amino acid sequence shown in SEQ ID NO: 3 or SEQ ID NO: 5, or a homologue, variant or derivative thereof.

Paragraph 2. A nucleic acid encoding a polypeptide according to Paragraph 1.

Paragraph 3. A nucleic acid according to Paragraph 2, comprising the nucleic acid sequence shown in SEQ ID NO: 1, SEQ ID NO: 2 or SEQ ID NO: 4, or a homologue, variant or derivative thereof.

Paragraph 4. A polypeptide comprising a fragment of a polypeptide according to Paragraph 1.

Paragraph 5. A polypeptide according to Paragraph 3 which comprises one or more regions which are homologous between SEQ ID NO: 3 and SEQ ID NO: 5, or which comprises one or more regions which are heterologous between SEQ ID NO: 3 and SEQ ID NO: 5.

Paragraph 6. A nucleic acid encoding a polypeptide according to Paragraph 4 or 5.

Paragraph 7. A vector comprising a nucleic acid according to Paragraph 2, 3, or 6.

Paragraph 8. A host cell comprising a nucleic acid according to Paragraph 2, 3, or 6, or vector according to Paragraph 7.

Paragraph 9. A transgenic non-human animal comprising a nucleic acid according to Paragraph 2, 3 or 6, or a vector according to Paragraph 7.

Paragraph 10. A transgenic non-human animal according to Paragraph 9 which is a mouse.

Paragraph 11. Use of a polypeptide according to Paragraph 1, 4 or 5 in a method of identifying a compound which is capable of interacting specifically with a G protein coupled receptor.

Paragraph 12. Use of a transgenic non-human animal according to Paragraph 9 or 10 in a method of identifying a compound which is capable of interacting specifically with a G protein coupled receptor.

Paragraph A method for identifying a compound capable of raising the endogenous level of cyclic AMP in a cell which method comprises contacting a cell which expresses GPR86 with a candidate compound and determining whether the level of cyclic AMP (cAMP) in the cell is raised as a result of said contacting.

Paragraph 14. A method for identifying a compound capable of lowering the endogenous level of cyclic AMP in a cell which method comprises contacting a cell which expresses GPR86 with a candidate compound and determining whether the level of cyclic AMP (cAMP) in the cell is lowered as a result of said contacting.

Paragraph 15. A method of identifying a compound capable of binding to a GPR86 polypeptide, the method comprising contacting a GPR86 polypeptide with a candidate compound and determining whether the candidate compound binds to the GPR86 polypeptide.

Paragraph 16. A compound identified by a method according to any of Paragraphs 11 to 15.

Paragraph 17. A compound capable of binding specifically to a polypeptide according to Paragraph 1, 4 or 5.

Paragraph 18. Use of a polypeptide according to Paragraph 1, 4 or 5, or part thereof or a nucleic acid according to Paragraph 2, 3 or 6, in a method for producing antibodies.

Paragraph 19. An antibody capable of binding specifically to a polypeptide according to Paragraph 1, 4 or 5, or part thereof or a polypeptide encoded by a nucleotide according to Paragraph 2, 3 or 6, or part thereof.

Paragraph 20. A pharmaceutical composition comprising any one or more of the following: a polypeptide according to Paragraph 1, 4 or 5, or part thereof; a nucleic acid according to Paragraph 2, 3 or 6, or part thereof; a vector according to Paragraph 7; a cell according to Paragraph 8; a compound according to Paragraph 16 or 17; and an antibody according to Paragraph 19, together with a pharmaceutically acceptable carrier or diluent.

Paragraph 21. A vaccine composition comprising any one or more of the following: a polypeptide according to Paragraph 1, 4 or 5, or part thereof, a nucleic acid according to Paragraph 2, 3 or 6, or part thereof; a vector according to Paragraph 7; a cell according to Paragraph 8; a compound according to Paragraph 16 or 17; and an antibody according to Paragraph 19.

Paragraph 22. A diagnostic kit for a disease or susceptibility to a disease comprising any one or more of the following: a polypeptide according to Paragraph 1, 4 or 5, or part thereof; a nucleic acid according to Paragraph 2, 3 or 6, or part thereof; a vector according to Paragraph 7; a cell according to Paragraph 8; a compound according to Paragraph 16 or 17; and an antibody according to Paragraph 19.

Paragraph 23. A method of treating a patient suffering from a disease associated with enhanced activity of GPR86, which method comprises administering to the patient an antagonist of GPR86.

Paragraph 24. A method of treating a patient suffering from a disease associated with reduced activity of GPR86, which method comprises administering to the patient an agonist of GPR86.

Paragraph 25. A method according to Paragraph 23 or 24, in which the GPR86 comprises a polypeptide having the sequence shown in SEQ ID NO: 3 or SEQ ID NO: 5.

Paragraph 26. A method for treating and/or preventing a disease in a patient, which comprises the step of administering any one or more of the following to the patient: a polypeptide according to Paragraph 1, 4 or 5, or part thereof; a nucleic acid according to Paragraph 2, 3 or 6, or part thereof; a vector according to Paragraph 7; a cell according to Paragraph 8, a compound according to Paragraph 16 or 17; an antibody according to Paragraph 19; a pharmaceutical composition according to Paragraph 20; and a vaccine according to Paragraph 20.

Paragraph 27. An agent comprising a polypeptide according to Paragraph 1, 4 or 5, or part thereof; a nucleic acid according to Paragraph 2, 3 or 6, or part thereof; a vector according to Paragraph 7; a cell according to Paragraph 8; a compound according to Paragraph 16 or 177; and/or an antibody according to Paragraph 19, said agent for use in a method of treatment or prophylaxis of disease.

Paragraph 28. Use of a polypeptide according to Paragraph 1, 4 or 5, or part thereof; a nucleic acid according to Paragraph 2, 3 or 6, or part thereof; a vector according to Paragraph 7; a cell according to Paragraph 8; a compound according to Paragraph 16 or 17; and an antibody according to Paragraph 19, for the preparation of a pharmaceutical composition for the treatment or prophylaxis of a disease.

Paragraph 29. A non-human transgenic animal, characterised in that the transgenic animal comprises an altered GPR86 gene.

Paragraph 30. A non-human transgenic animal according to Paragraph 29, in which the alteration is selected from the group consisting of: a deletion of GPR86, a mutation in GPR86 resulting in loss of function, introduction of an exogenous gene having a nucleotide sequence with targeted or random mutations into GPR86, introduction of an exogenous gene from another species into GPR86, and a combination of any of these.

Paragraph 31. A non-human transgenic animal having a functionally disrupted endogenous GPR86 gene, in which the transgenic animal comprises in its genome and expresses a transgene encoding a heterologous GPR86 protein.

Paragraph 32. A nucleic acid construct for functionally disrupting a GPR86 gene in a host cell, the nucleic acid construct comprising: (a) a non-homologous replacement portion; (b) a first homology region located upstream of the non-homologous replacement portion, the first homology region having a nucleotide sequence with substantial identity to a first GPR86 gene sequence; and (c) a second homology region located downstream of the non-homologous replacement portion, the second homology region having a nucleotide sequence with substantial identity to a second GPR86 gene sequence, the second GPR86 gene sequence having a location downstream of the first GPR86 gene sequence in a naturally occurring endogenous GPR86 gene.

Paragraph 33. A process for producing a GPR86 polypeptide, the method comprising culturing a host cell according to Paragraph 8 under conditions in which a nucleic acid encoding a GPR86 polypeptide is expressed.

Paragraph 34. A method of detecting the presence of a nucleic acid according to Paragraph 2, 3 or 6 in a sample, the method comprising contacting the sample with at least one nucleic acid probe which is specific for said nucleic acid and monitoring said sample for the presence of the nucleic acid.

Paragraph 35. A method of detecting the presence of a polypeptide according to Paragraph 1, 4 or 5 in a sample, the method comprising contacting the sample with an antibody according to Paragraph 19 and monitoring said sample for the presence of the polypeptide.

Paragraph 36. A method of diagnosis of a disease or syndrome caused by or associated with increased, decreased or otherwise abnormal expression of GPR86, the method comprising the steps of: (a) detecting the level or pattern of expression of GPR86 in an animal suffering or suspected to be suffering from such a disease, and (b) comparing the level or pattern of expression with that of a normal animal.

Paragraph 37. A kit according to Paragraph 22, a method according to any of Paragraphs 23 to 26, an agent according to Paragraph 27, a use according to Paragraph 28, or a method according to Paragraph 36, in which the disease is associated with inflammatory disorders, preferably selected from the group consisting of inflammatory diseases (e.g. rheumatoid arthritis, multiple sclerosis, Guillain-Barre syndrome, Crohn's disease, ulcerative colitis, psoriasis, graft versus host disease, systemic lupus, erythematosus or insulin-dependent diabetes mellitus), autoimmune diseases (e.g. toxic shock syndrome, osteoarthritis, diabetes or inflammatory bowel disease), acute pain, chronic pain, neuropathic pain, contact dermatitis, atherosclerosis, glomerulonephritis, reperfusion injury, bone resorption diseases, asthma, stroke, myocardial infarction, thermal injury, adult respiratory distress syndrome (ARDS), multiple organ injury secondary to trauma, dermatoses with acute inflammatory components, acute purulent meningitis, necrotising enterocolitis, syndromes associated with hemodialysis, septic shock, leukopherisis, granulocyte transfusion, acute or chronic inflammation of the lung caused by smoke inhalation, endometriosis, Behcet's disease, uveitis, ankylosing spondylitis, pancreatitis, cancer, Lyme disease, restenosis following percutaneous transluminal coronary angioplasty, Alzheimer's disease, traumatic arthritis, sepsis, chronic obstructive pulmonary disease, congestive heart failure, osteoporosis, cachexia, Parkinson's disease, periodontal diseases, gout, allergic diseases, age-related macular degeneration, infection and cystic fibrosis.

EXAMPLES

Example 1

Transgenic GPR86 Knock-Out Mouse: Construction of GPR86 Gene Targeting Vector

A PAC containing the GPR86 gene is identified from a PAC library using a radioactively labelled probe derived from a section of the coding sequence. A 8.0 kb genomic contig is assembled using an in-house restriction site anchored PCR method similar to GeneWalker (Clontech). Further bio-informatic work increased the contig size to 300 kb. This contig provided sufficient flanking sequence information to enable the design of homologous arms to clone into the targeting vector.

Figure 2:
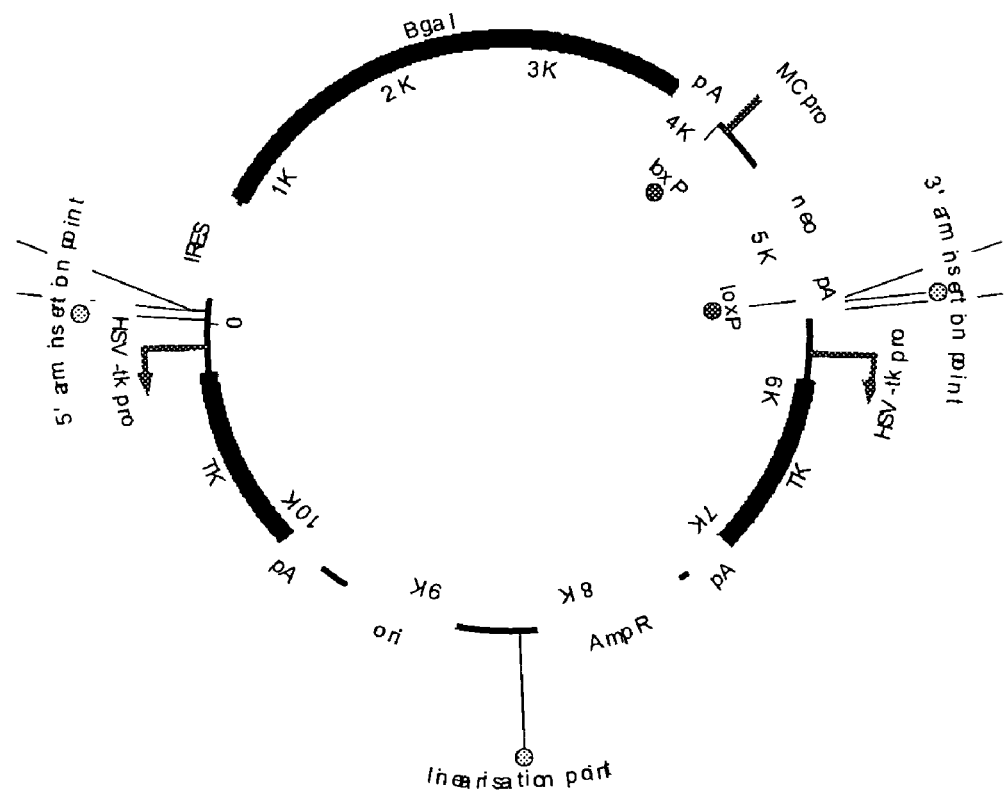
FIG. 2 is a diagram showing a representation of the knockout plasmid.

The murine GPR86 gene has 1 coding exon. The targeting strategy is designed to remove the majority of the coding sequence, including the entirety of the transmembrane domains. A 3.9 kb 5' homologous arm and a 1.2 kb 3' homologous arm flanking the region to be deleted are amplified by PCR and the fragments are cloned into the targeting vector. The 5' end of each oligonucleotide primer used to amplify the arms is synthesised to contain a different recognition site for a rare-cutting restriction enzyme, compatible with the cloning sites of the vector polylinkers and absent from the arms themselves. In the case of GPR86, the primers are designed as listed in the primer table below, with 5' arm cloning sites of Sal/Not and 3' arm cloning sites of Asc/Mfe (the structure of the targeting vector used, including the relevant restriction sites, is shown in FIG. 2).

In addition to the arm primer pairs (5' armF/5' armR) and (3' armF/3' armR), further primers specific to the GPR86 locus are designed for the following purposes: 5' and 3' probe primer pairs (5' prF/5' prR and 3' prF/3' prR) to amplify two short 150-300 bp fragments of non-repetitive genomic DNA external to and extending beyond each arm, to allow Southern analysis of the targeted locus, in isolated putative targeted clones; a mouse genotyping primer pair (hetF and hetR) which allows differentiation between wild-type, heterozygote and homozygous mice, when used in a multiplex PCR with a vector specific primer, in this case, Asc350; and lastly, a target screening primer (3' scr) which anneals downstream of the end of the 3' arm region, and which produces a target event specific 1.25 kb amplimer when paired with a primer specific to the 3' end of the vector (TK5IBLMNL), in this case Asc236. This amplimer can only be derived from template DNA from cells where the desired genomic alteration has occurred and allows the identification of correctly targeted cells from the background of clones containing randomly integrated copies of the vector. The location of these primers and the genomic structure of the regions of the GPR86 locus used in the targeting strategy is shown in SEQ ID NO: 21.

TABLE 1

GPR86 Primer Sequences musGPR86 5' pr F
TATACATATGTTCAGCAGTACCAACTC-SEQ ID NO: 8 musGPR86 5' pr R
ACACCAGTGTATAGATAGCAAGAAGTC-SEQ ID NO: 9 musGPR86 5' arm F
cccgtcgacATGCTTTCTTTTATGACAAAATCCTTG-SEQ ID NO: 10 musGPR86 5' arm R
aaagcggccGcGAACAGCAGCTGTGTCATCCGAGTG-SEQ ID NO: 11 musGPR86 3' arm F
aaaggcgcgccAGGCAAGAACAGCAGGATCAAGCGAAG-SEQ ID NO: 12 musGPR86 3' arm R
aaacaattGTGGCTTCTGAGGCTATGGAAAGAGAG-SEQ ID NO: 13 musGPR86 3' pr F
ATATGGCACATTTGGTCCGCACTGCAC-SEQ ID NO: 14 musGPR86 3' pr R
GATGAGGAATGATGTCACACAGATGAG-SEQ ID NO: 15 musGPR86 3' scr
AAGGTCAAGATTAGCAAGTGATTCCAG-SEQ ID NO: 16 musGPR86 hetF
ATACCATACACTTACAGTCAAACCACC-SEQ ID NO: 17 musGPR86 hetR
GGTCTTCGCTTGATCCTGCTGTTCTTG-SEQ ID NO: 18

Asc236
TTGGCTACCCGTGATATTGCTGAAGAG-SEQ ID NO: 19

Asc350
GTCGTGACCCATGGCGATGCCTGCTTG-SEQ ID NO: 20

The position of the homology arms is chosen to functionally disrupt the GPR86 gene. A targeting vector is prepared where the GPR86 region to be deleted is replaced with non-homologous sequences composed of an endogenous gene expression reporter (a frame independent lacZ gene) upstream of a selection cassette composed of a promoted neomycin phosphotransferase (neo) gene arranged in the same orientation as the GPR86 gene.

Once the 5' and 3' homology arms have been cloned into the targeting vector TK5IBLMNL (see FIG. 2), a large highly pure DNA preparation is made using standard molecular biology techniques. 20 µg of the fleshly prepared endotoxin-free DNA is restricted with another rare-cutting restriction enzyme SwaI, present at a unique site in the vector backbone between the ampicillin resistance gene and the bacterial origin of replication. The linearized DNA is then precipitated and resuspended in 100 µl of Phosphate Buffered Saline, ready for electroporation.

24 hours following electroporation the transfected cells are cultured for 9 days in medium containing 200 µg/ml neomycin. Clones are picked into 96 well plates, replicated and expanded before being screened by PCR (using primers 3' scr and Asc236, as described above) to identify clones in which homologous recombination has occurred between the endogenous GPR86 gene and the targeting construct. Positive clones can be identified at a rate of 1 to 5%. These clones are expanded to allow replicas to be frozen and sufficient high quality DNA to be prepared for Southern blot confirmation of the targeting event using the external 5' and 3' probes prepared as described above, all using standard procedures (Russ et al, Nature 2000 Mar. 2; 404 (6773):95-99). When Southern blots of DNA digested with diagnostic restriction enzymes are hybridized with an external probe, homologously targeted ES cell clones are verified by the presence of a mutant band as well an unaltered wild-type band. For instance, using the 5' probe, HindIII digested genomic DNA will give a 14.9 kb wild-type band and a 12.0 kb targeted band; and with the 3' probe, HinDIII cut DNA will give a 14.9 kb wild-type band and an 7.0 kb targeted band.

Example 2

Transgenic GPR86 Knock-Out Mouse: Generation of GPR86 Deficient Mice

C57BL/6 female and male mice are mated and blastocysts are isolated at 3.5 days of gestation. 10-12 cells from a chosen clone are injected per blastocyst and 7-8 blastocysts are implanted in the uterus of a pseudopregnant F1 female. A litter of chimeric pups are born containing several high level (up to 100%) agouti males (the agouti coat colour indicates the contribution of cells descended from the targeted clone). These male chimeras are mated with female MF1 and 129 mice, and germline transmission is determined by the agouti coat colour and by PCR genotyping respectively.

PCR Genotyping is carried out on lysed tail clips, using the primers hetF and hetR with a third, vector specific primer (Asc350). This multiplex PCR allows amplification from the wild-type locus (if present) from primers hetF and hetR giving a 207 bp band. The site for hetF is deleted in the knockout mice, so this amplification will fail from a targeted allele. However, the Asc350 primer will amplify a 380 bp band from the targeted locus, in combination with the hetR primer which anneals to a region just inside the 3' arm. Therefore, this multiplex PCR reveals the genotype of the litters as follows: wild-type samples exhibit a single 207 bp band; heterozygous DNA samples yield two bands at 207 bp and 380 bp; and the homozygous samples will show only the target specific 380 bp band.

Example 3

Biological Data: Gene Expression Patterns RT-PCR

Using RT-PCR, expression of the gene is shown in the liver and leukocytes (FIG. 3).

Example 4

Biological Data: Expression of GPR86 by RT-PCR

Expression of GPR86 mRNA was examined using RT-PCR using cDNA libraries from both human and mouse. For human sequences the primers

```
Forward    5'-GGTGTTTGTTCACATCCCCAGC-3'

Reverse    5'-TGGTGTTGCTTCCTTGTTGCTC-3'
``` can be used to give a product of 364 bp.
The conditions for the reaction are as follows:

| | |
|---|---|
| 85° C. | Hot start |
| 94° C. | 15 seconds |
| 60° C. | 30 seconds for 40 cycles |
| 72° C. | 60 seconds |
| 4° C. | Hold |

Products are separated on a Tris acetate EDTA agarose gel containing ethidium bromide and were viewed using a UV light source.

Expression in human derived tissues (FIG. 7) and cells was found in bone marrow, thymus, lymph node, osteoblasts and chondrocytes. It was also found in the human derived cell lines Jurkat CD4+ and Myla CD8+, both derived from T-cells. Low levels of expression was seen in Colo720, derived from lymphocytes, and THP1 cells which are derived from monocytes.

In mouse tissues (FIG. 8) expression was found in spleen, salivary glands, spinal cord, tongue, adipose, testis, heart, eyes, lung, kidney, thymus, stomach and small intestine, brain, liver and gall bladder, blood, bladder and adrenal gland.

Expression of GPR86 included cells derived from immune responsive cells implying that GPR86 is involved in immune cell function including those that are involved in inflammatory and neuropathic aspects of pain.

Example 5

Tests for Sensitivity to External Stimuli and Pain (Analgesia Testing) in GPR86 Knock-Out Mouse: Tail Flick Test A tail flick analgesia test is performed using a Tail-Flick Analgesia Meter. This equipment provides an easy to use method to determine pain sensitivity accurately and reproducibly in rodents (D'Amour, F. E. and D. L. Smith, 1941, Expt. Clin. Pharmacol., 16: 179-184). The instrument has a shutter-controlled lamp as a heat source. The lamp is located below the animal to provide a less confining environment. Tail flick is detected by the automatic detection circuitry, which leaves the user's hands free to handle the animal. The animal is restrained in a ventilated tube and its tail placed on a sensing groove on top of the equipment.

Activation of an intense light beam to the tail through opening of the shutter results in discomfort at some point when the animal will flick its tail out of the beam. In the automatic mode a photo-detector detects the tail motion causing the clock to stop and the shutter to close. The total time elapsed between the shutter opening and the animal's reaction is recorded.

Responses of mutant transgenic mice are compared with age and sex matched wild-type mice. A single animal may be subjected to different heat settings to produce an increase in tail temperature no greater than 55° C.

Knockout and wildtype control animals are tested on the tail flick apparatus. There is a significant difference between the latency to withdraw the tail between the knockout animals (6.88±0.26 sec) compared to the wildtype controls (5.95±0.28). Therefore, the knockout animals are less sensitive than wild type animals (FIG. 4).

Example 6

Tests for Sensitivity to External Stimuli and Pain (Analgesia Testing) in GPR86 Knock-Out Mouse: Formalin Test The formalin test measures the response to a noxious substances injected into a hind paw. A volume of 20 µl of a 5% formalin solution is injected through a fine gauge needle subcutaneously into the dorsal surface of one hindpaw. Licking, shaking and biting the hindpaw is quantitated as cumulative number of seconds engaged in the behaviours. A rating scale is used: 1=the formalin injected paw rests lightly on the floor bearing less weight, 2=the injected paw is elevated, 3=the injected paw is licked, bitten or shaken.

Two phases of responses are seen in the formalin test. Phase 1 begins immediately after injection and lasts about 10 mins, representing the acute burst of activity from pain fibres. Phase two begins about 20 mins after injection and continues for about one hour. This phase appears to represent responses to tissue damage, including inflammatory hyperalgesia.

Figure 5:
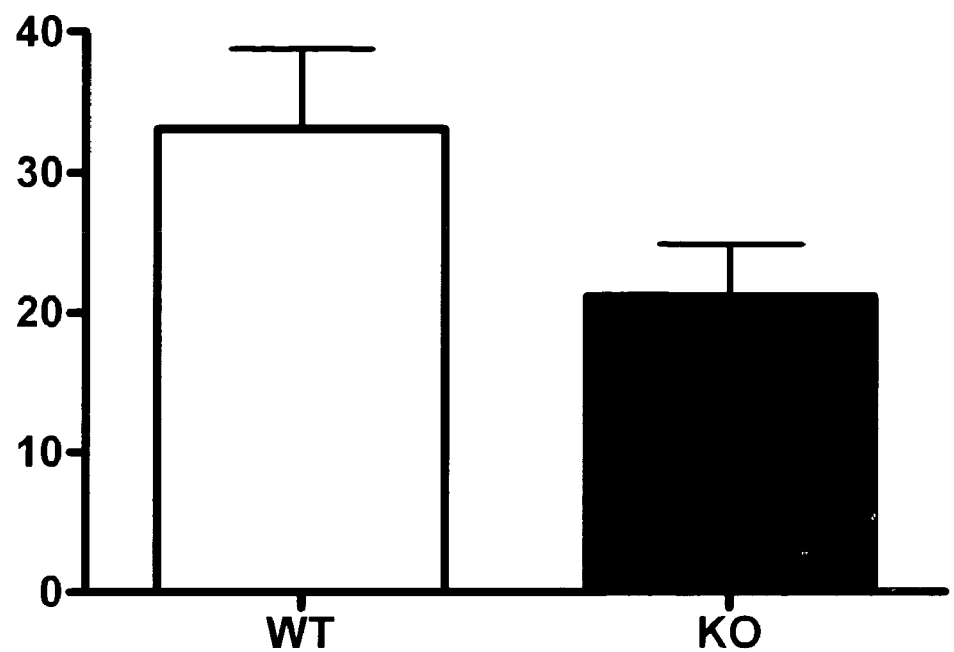
FIG. 5 is a graph of data from the Formalin test, showing results expressed as percentage increase in paw width from GPR86 knockout (white) versus wild type animals (black).

GPR86 mutants are tested in the formalin test and found to less responsive, as measured by number of licks bites or shakes of the injected foot. The inflammatory oedema of the foot in response to the injected formalin is also reduced in the KO mice by 12% compared to wildtype oedema (FIG. 5).

Example 7

Tests for Sensitivity to External Stimuli and Pain (Analgesia Testing) in GPR86 Knock-Out Mouse: Von Frey Hair Test A test for touch, which is used to measure pain thresholds, employs von Frey hairs. These hairs are a set of very fine gauge calibrated wires. Withdrawal threshold to mechanical stimulation is measured. The animal stands on an elevated platform in which the surface is a wide gauge wire mesh. The Von Frey hair is inserted from below, up through the holes in the mesh, to poke the undersurface of the hindpaw. At threshold, the mouse responds by flicking its paw away from the hair, generally followed by raising the paw, licking the paw, and or vocalisation. Mechanical withdrawal threshold is defined as the minimum gauge wire stimulus that elicits withdrawal reactions in two out of three consecutive trials.

Knockout and wildtype control animals are tested on Electronic Vonfrey (5 test on each rear paw). There is a significant difference between the latency to withdraw the paw between the knockout animals (5.9±0.2 sec) compared to the wildtype controls (5.2±0.2, p=0.03, t test). Therefore, the knockout animals are less sensitive than wild types (FIG. 6).

Example 8

Tests for Sensitivity to External Stimuli in GPR86 Knock-Out Mouse: Neuropathic Pain Neuropathic pain is induced by loosely ligating the sciatic nerve of an anaesthetised mouse. Adult male mice are anaesthetised with 5% isofluorane followed by an i.p. injection of pentobarbitone (50 mg/kg) and a chronic constriction injury (CCI) of the sciatic nerve is produced according to the method of Bennett & Xie (1988). Briefly, the skin over the operation area is shaved, sterilized and an incision made in the mid-thigh level along the femur. The left common sciatic nerve is exposed at mid-thigh level by blunt separation and 3 loose ligatures about 1 mm apart from each other are placed proximal to the bifurcation with 6-0 silk thread. The wound is closed in layers using stitch. After surgery, infection is prevented by an intraperitoneal injection of antibiotics and the animals placed on a soft cushion in a recovering chamber with temperature maintained at 30° C. The animals are placed back to the home cage with clean soft bedding after complete recovery. Following recovery the development and maintenance of neuropathic pain is measured in terms of allodynia (perception of pain to non-noxious stimuli) using von Frey filaments (as described in Example 7) over a period of 2-3 weeks. Each hind paw is tested and the responses of the ipsilateral (injury side) and contralateral (naïve side) paw responses compared between knock-out and wild type mice.

Figure 9:
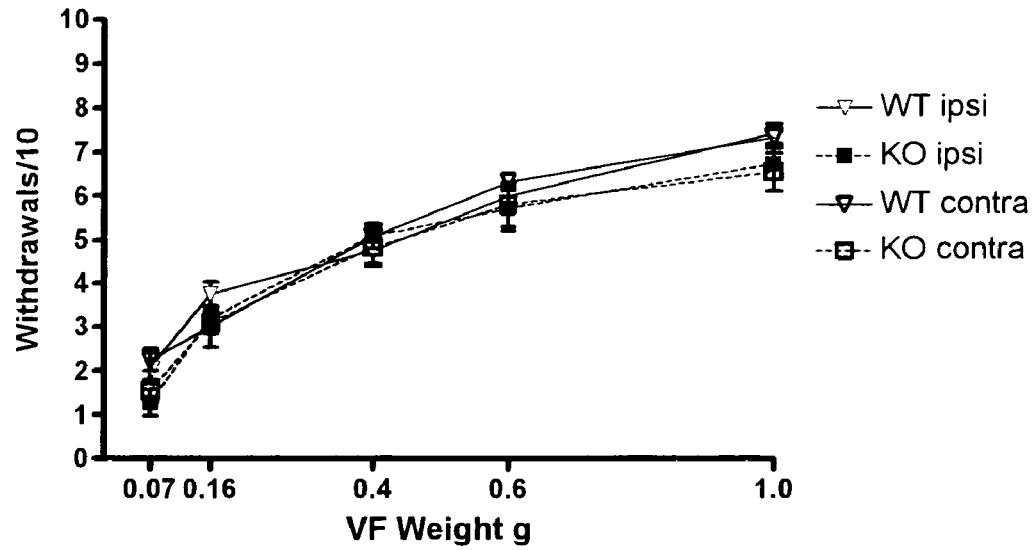
FIG. 9 shows the results of tests for sensitivity to external stimuli in GPR86 knock-out mouse: neuropathic pain. Wild type (n=12) and GPR86 knockout mice (n=10) paw withdrawal frequency as measured per 10 Von Frey hair applications. Data is plotted for each hair weight pre (day−1) and post surgery (day 14).
Figure 9:
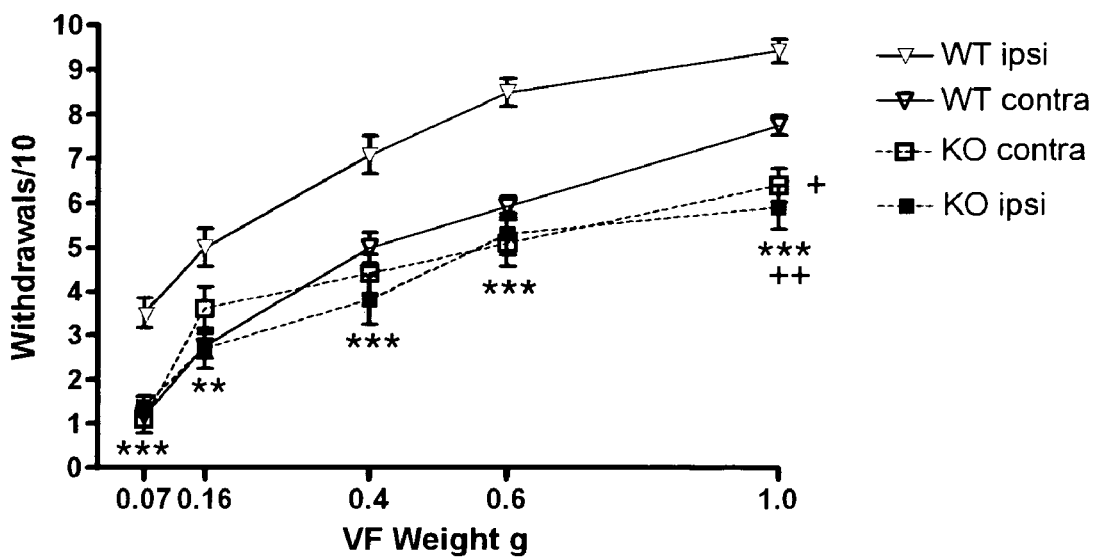

FIG. 9 shows pre and post surgery paw withdrawal frequency. The results show that the knockout mice have a significant decreased paw withdrawal frequency compared to wt mice (FIG. 9) and are therefore resistant to the development of allodynia and hence neuropathic pain. This would indicate that a compound/reagent to GPR86 would have utility in the prevention & treatment of neuropathic pain, inflammatory pain and inflammation.

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments and that many modifications and additions thereto may be made within the scope of the invention. Indeed, various modifications of the described modes for carrying out the invention which are obvious to those skilled in molecular biology or related fields are intended to be within the scope of the claims. Furthermore, various combinations of the features of the following dependent claims can be made with the features of the independent claims without departing from the scope of the present invention.

```
SEQ ID NO: 1 shows the cDNA sequence of human GPR86
TCATTTGTAGGCTGAACTAATGACTGCCGCCATAAGAAGACAGAGAGAACTGAGTATCCTCCCAAAGGTGACACTGGAAGCAATGAACACCACAGTGATGCAA GGCTTCAACAGATCTGAGCGGTGCCCCAGAGACACTCGGATAGTACAGCTGGTATTCCCAGCCCTCTACACAGTGGTTTTGTTGACCGGCATCCTGCTGAATA CTTTGGCTCTGTGGGTGTTTGTTCACATCCCCAGCTCCTCCACCTTCATCATCTACCTCAAAAACACTTTGGTGGCCGACTTGATAATGACACTCATGCTTCC TTTCAAAATCCTCTCTGACTCACACCTGGCACCCTGGCAGCTCAGAGCTTTTGTGTGTCGTTTTTCTTCGGTGATATTTTATGAGACCATGTATGTGGGCATC GTGCTGTTAGGGCTCATAGCCTTTGACAGATTCCTCAAGATCATCAGACCTTTGAGAAATATTTTTCTAAAAAAACCTGTTTTTGCAAAAACGGTCTCAATCT TCATCTGGTTCTTTTTGTTCTTCATCTCCCTGCCAAATATGATCTTGAGCAACAAGGAAGCAACACCATCGTCTGTGAAAAAGTGTGCTTCCTTAAAGGGGCC TCTGGGGCTGAAATGGCATCAAATGGTAAATAACATATGCCAGTTTATTTTCTGGACTGTTTTTATCCTAATGCTTGTGTTTTATGTGGTTATTGCAAAAAAA GTATATGATTCTTATAGAAAGTCCAAAAGTAAGGACAGAAAAAACAACAAAAAGCTGGAAGGCAAAGTATTTGTTGTCGTGGCTGTCTTCTTTGTGTGTTTTG CTCCATTTCATTTTGCCAGAGTTCCATATACTCACAGTCAAACCAACAATAAGACTGACTGTAGACTGCAAAATCAACTGTTTATTGCTAAAGAAACAACTCT CTTTTTGGCAGCAACTAACATTTGTATGGATCCCTTAATATACATATTCTTATGTAAAAAATTCACAGAAAAGCTACCATGTATGCAAGGGAGAAAGACCACA GCATCAAGCCAAGAAAATCATAGCAGTCAGACAGAGAACATAACCTTAGGCTGACAACTGTACATAGGGTTAACTTCTATTTATTGATGAGACTTCCGTAGAT AATGTGGAAATCAAATTTAACCAAGAAAAAAAGATTGGAACAAATGCTCTCTTACATTTTATTATCCTGGTGTACAGAAAAGATTATATAAAATTTAAATCCA CATAGATCTATTCATAAGCTGAATGAACCATTACTAAGAGAATGCAACAGGATACAAATGGCCACTAGAGGTCATTATTTCTTTCTTTCTTTTTTTTTTTTT AATTTCAAGAGCATTTCACTTTAACATTTTGGAAAAGACTAAGGAGAAACGTATATCCCTACAAACCTCCCCTCCAAACACCTTCTCACATTCTTTTCCACAA TTCACATAACACTACTGCTTTTGTGCCCCTTAAATGTAGATATGTGCTGAAAGAAAAAAAAAACGCCCAACTCTTGAAGTCCATTGCTGAAAACTGCAGCCAG GGGTTGAAAGGGATGCAGACTTGAAGAGTCTGAGGAACTGAAGTGGGTCAGCAAGACCTCTGAAATCCTGGGTAAAGGATTTTCTCCTTACAATTACAAACAG CCTCTTTCACATTACAATAATATACCATAGGAGGCACAAGCACCATTATTAAGCCACTTTGCTTACACCTTAAGTGTGTACAATTCAAGTGTGAGAATGCTGT GTTAACTATTCTTTGGAATTCTCCTTCTGTCCAGCAAATACTCTAATGATGGTTAAACATGGCACCTACTCAGCAATGCCTTCCTGGACCACAACCCCTATCC CCCTGCCCCACCCTCCTCATTAAAAACAAATACTTCTACTGTTTGGGTGTGTGATAGGGTTCTCAATGCAGATCTCCCTTTTCTAGTTAGCTATATTCTTGAC
```

-continued

TGCATCCGCTAAAAATGTTAAAGCTTCTTGAGAGACAGACATGCCAGATTTTCTTGGTATCTCCCATAATACGACCTACAGTCCATGGTCTACAGATGTTTTA

AATAGAATTGCTATTCTCGATACATACAAAGACGTAATTGCTGACCCACAATCAGTAACATCCATATTGGGAGATTTTTCAAAGGATGGTGACCCTGCTTGTA

TTTATTTACCTTGGTATTTTTTCTTGCATCCTTCTGTGATTCAAAAAAGTAAAATGTGGCTTTCTGAAATGATGGATAAGAGTCTACATCTTCTAGAAAAAAT

ACATAAAGGAGTAGTTAAGCTCTGTAAATGTGCCACGAGCTCCAACACGACCATCGTAGGGTGAAGCCCACGTTTTCTTCCATGCCCTCAAAGGCCCTAGAAC

TTGCCTACCTTTCTGGCCTTACCTCCTAGCTACTTATCCATCTCTTGAACTTTATACTCTTGTATAAATTTCTAACTTTCAGAAAATGCCATACTCTGTTTTG

GCACCACACATGTATATTTCCCCCTGGTACACTTGGAAGACTCTTATCCATCTGTGAAACCCTATGTTGTCATCACTTGGTCCATGAATATTACCTGGCCAA

TATCCCACCATCACCTCAAACCCAATCACCCCCTCCTCTGTATGCTGTCACACCTATATTATTAAACTTATCACATTGCATTGTAATTACTTCCTGACCTTTG

TATCTACTCTTTTAGTAACTGATGTATATATCTGAAAGGAGAGATTGTTTCATTGTGCAATCAATAAATGTTTGATAAAATAAAGCCC

SEQ ID NO: 2 shows an open reading frame derived from SEQ ID NO: 1
ATGACTGCCGCCATAAGAAGACAGAGAGAACTGAGTATCCTCCCAAAGGTGACACTGGAAGCAATGAACACCACAGTGATGCAAGGCTTCAACAGATCTGAGC GGTGCCCCAGAGACACTCGGATAGTACAGCTGGTATTCCCAGCCCTCTACACAGTGGTTTTCTTGACCGGGATCCTGCTGAATACTTTGGCTCTGTGGGTGTT TGTTCACATCCCCAGCTCCTCCACCTTCATCATCTACCTCAAAAACACTTTGGTGGCCGACTTGATAATGACACTCATGCTTCCTTTCAAAATCCTCTCTGAC TCACACCTGGCACCCTGGCAGCTCAGAGCTTTTGTGTGTCGTTTTTCTTCGGTGATATTTTATGAGACCATGTATGTGGGCATCGTGCTGTTAGGGCTCATAG CCTTTGACAGATTCCTCAAGATCATCAGACCTTTGAGAAATATTTTTCTAAAAAAACCTGTTTTTGCAAAAACGGTCTCAATCTTCATCTGGTTCTTTTTGTT CTTCATCTCCCTGCCAAATATGATCTTGAGCAACAAGGAAGCAACACCATCGTCTGTGAAAAGTGTGCTTCCTAAAGGGGCCTCTGGGGCTGAAATGGCAT CAAATGGTAAATAACATATGCCAGTTTATTTTCTGGACTGTTTTTATCCTAATGCTTGTGTTTTATGTGGTTATTGCAAAAAAGTATATGATTCTTATAGAA AGTCCAAAAGTAAGGACAGAAAAAAACAACAAAAAGCTGGAAGGCAAAGTATTTGTTGTCGTGGCTGTCTTCTTTGTGTGTTTTGCTCCATTTCATTTTGCCAG AGTTCCATATACTCACAGTCAAACCAACAATAAGACTGACTGTAGACTGCAAAATCAACTGTTTATTGCTAAAGAAACAACTCTCTTTTTGGCAGCAACTAAC ATTTGTATGGATCCCTTAATATACATATTCTTATGTAAAAAATTCACAGAAAAGCTACCATGTATGCAAGGGAGAAAGAGCACAGCATCAAGCCAAGAAAATC

ATAGCAGTCAGACAGACAACATAACCTTAGGCTGA

SEQ ID NO: 3 shows the amino acid sequence of human GPR86
MTAAIRRQRELSILPKVTLEAMNTTVMQGFNRSERCPRDTRIVQLVFPALYTVVFLTGILLNTLALWVFVHIPSSSTFIIYLKNTLVADLIMTLMLPFKILSD SHLAPWQLRAFVCRFSSVIFYETMYVGIVLLGIAFDRFLKIIRPLRNFFLKKPVFAKTVSIFIWFFLFFISLPNMILSNKEATPSSVKKCASLKGPLGLKWHQ MVMNICQFIFWTVFILMLVFYVVIAKKVYDSYRKSKSKDRKNNKKLEGKVFVVVAVFFVCFAPFHFARVPYTHSQTNNKTDCRLQNQLFIAKETTLFLAATNI

CMDPLIYIFLCKKFTEKLPGMQGRKTTASSQENHSSQTDNITLG

SEQ ID NO: 4 shows the open reading frame of a cDNA for Mouse GPR86
ATGCTCGGGACAATCAACACCACTGGGATGCAGGGCTTCAACAAGTCTGAGCGGTGCCCCAGGGACACTCGGATGACACAGCTGCTGTTCCCGGTTCTCTATA CTGTGGTCTTCCTGGCAGGCATCCTGCTGAACACCGTGGCCCTCTGGGTGTTCGTCCACATCCCCAGCAATTCCACCTTTATCGTCTACCTCAAGAACACTCT GGTGGCAGACTTGATAATGGCACTCATGCTGCCTTTCAAAATCCTTTCCGACTCACACCTTGCGCCCTGGCAGCTCCGAGGATTTGTGTGCACGCTCTCCTCC GTGGTCTTCTATGAGACGATGTATGTGGGTATCATGATGCTGGGCCTCATCGCTTTCGACAGGTTCCTCAAGATCATCATGCCGTTCAGGAAAACCTTTGTCA AAAAGACGGCTTTCGCAAAAACAGTCTCCATTTCCGTCTGGTCCCTGATGTTCTTCATCTCCCTGCCAAACATGATCTTGAACAAGGAGGCAACGCCATCATC CGTGAAGAAGTGTGCATCTTTGAAGAGTCCCCTTGGGCTGTGGTGGCATGAGGTGGTCAGTCACACCTGCCAGTTCATTTTCTGGGCTGTGTTTATTCTGATG CTTCTGTTTTATGCGGTGATTACCAAAAAGGTGTACAACTCCTATAGGAAGTTTAGGAGTAAGGACAGCAGGCACAAGCGGCTGGAGGTGAAGGTATTTATCG TCATGGCTGTCTTCTTTGTCTGCTTTGCCCCACTGCATTTTGTCAGAATACCATACACTTACAGTCAAACCACCAATAAGACTGACTGTAGGTTAGAAACCA GCTGTTTATTGCTAAAGAAGCAACTCTCTTTCTGGCAACAACTAACATTTGTATGGACCCCTTAATATACATAATTTTATGCAAGAAGTTCACACAAAAGGTG CCATGTGTGAGATGGGAAAGGCAAGAACAGCAGGATCAAGCGAAGACCACCACAGTAGTCAGACAGACAACATCACCCTAGGCTGA SEQ ID NO: 5 shows the amino acid sequence of Mouse GPR86
MLGTINTTGMQGFNKSERCPRDTRMTQLLFPVLYTVVFLAGILLNTVALWXTFVHWSNSTFIVYLKNTLVADLIIMALMLPFKWSDSHLAPWQLRGFVCTLSS VVFYETMYVGIMMLGLIAFDRFLKIIMPFRKTFVKKTAFNKTVSISVWSLMFFISLPNMWNKEATPSSVKKCASLKSPLGLWWHQVVSHTCQFIFWAVFILML LFYAVITKKVYNSYRKFRSKDSRHKRLEVKVPIVMAVFFVCFAPLHFVRWYTYSQTTNKTDCRLENQLFIAKEATLFLATTNICMDPLIYIILCKKFTQKVPC

VRWGKARTAGSSEDHHSSQTDNITLAZ

SEQ ID NO: 6 shows an alternative cDNA sequence of human GPR86
TATGTTTATTGGTAACAGGTGACACTGGAAGCAATGAACACCACAGTGATGCAAGGCTTCAACAGATCTGAGCGGTGCCCCAGAGACACTCGGATAGTACAGC
TGGTATTCCCAGCCCTCTACACAGTGGTTTTCTTGACCGGCATCCTGCTGAATACTTTGGCTCTGTGGGTGTTTGTTCACATCCCCAGCTCCTCCACCTTCAT
CATCTACCTCAAAAACACTTTGGTGGCCGACTTGATAATGACACTCATGCTTCCTTTCAAAATCCTCTCTGACTCACACCTGGCACCCTGGCAGCTCAGAGCT
TTTGTGTGTCGTTTTTCTTCGGTGATATTTTATGAGACCATGTATGTGGGCATCGTGCTGTTAGGGCTCATAGCCTTTGACAGATTCCTCAAGATCATCAGAC
GTTTGAGAAATATTTTTCTAAAAAAACCTGTTTTTGCAAAAACGGTCTCAATCTTCATCTGGTTCTTTTTGTTCTTCATCTCCCTGCCAAATATGATCTTGAG
CAACAAGGAAGCAACACCATCGTCTGTGAAAAAGTGTGCTTCCTTAAAGGGGCCTCTGGGGCTGAAATGGCATCAAATGGTAAATAACATATGCCAGTTTATT
TTCTGGACTGTTTTTATCCTAATGCTTGTGTTTTATGTGGTTATTGCAAAAAAGTATATGATTCTTATAGAAAGTCCAAAAGTAAGGACAGAAAAAACAACA
AAAAGCTGGAAGGCAAAGTATTTGTTGTCGTGGCTGTCTTCTTTGTGTGTTTTGCTCCATTTCATTTTGCCAGAGTTCCATATACTCACAGTCAAACCAACAA
TAAGACTGACTGTAGACTGCAAAATCAACTGTTTATTGCTAAAGAAACAACTCTCTTTTTGGCAGCAACTAACATTTGTATGGATCCCTTAATATACATATTC
TTATGTAAAAAATTCACAGAAAAGCTACCATGTATGCAAGGGAGAAAGAGCACAGCATCAAGCCAAGAAAATCATAGCAGTCAGACAGACAACATAACCTTAG
GCTGACAACTGTACATAGGGTTAACTTCTATTTATTGATGAGACTTCCGTAGATAATGTGGAAATCAAATTTAACCAAGAAAAAAGATTGGAACAAATGCTC
TCTTACATTTTATTATCCTGGTGTAGAGAAAAGATTATATAAAATTTAAATCCACATAGATCTATTCATAAGCTGAATGAACCATTACTAAGAGAATGCAACA
GGATACAAATGGCCACTAGAGGTCATTATTTCTTTCTTTCTTTTTTTTTTTTTAATTTCAAGAGCATTTCACTTTAACATTTTGGAAAAGACTAAGGAGAAA
CGTATATCCCTACAAACCTCCCCTCCAAACACCTTCTCACATTCTTTTCCACAATTCACATAACACTACTGCTTTTGTGCCCCTTAAATGTAGATATGTGCTG
AAAGAAAAAAAAAACGCCCAACTCTTGAAGTCCATTGCTGAAAACTGCAGCCAGGGGTTGAAAGGGATGCAGACTTGAAGAGTCTGAGGAACTGAAGTGGGTC
AGCAAGACCTCTGAAATCCTGGGTAAAGGATTTTCTCCTTACAATTACAAACAGCCTCTTTCACATTACAATAATATACCATAGGAGGCACAAGCACCATTAT
TAAGCCACTTTGGTTACACCTTAAGTGTGTACAATTCAAGTGTGAGAATGCTGTGTTAACTATTCTTTGGAATTCTCCTTCTGTCCAGCAAATACTCTAATGA
TGGTTAAACATGGCACCTACTCAGCAATGCCTTCCTGGACCACAACCCCTATCCCCCTGCCCCACCCTCCTCATTAAAAACAAATACTTCTACTGTTTGGGTG
TGTGATAGGGTTCTCAATGCAGATCTCCCTTTTCTAGTTAGCTATATTCTTGACTGCATCCGCTAAAAATGTTAAAGCTTCTTGAGAGACAGACATGCCAGAT
TTTCTTGGTATCTCCCATAATACGACCTACAGTCCATGGTCTACAGATGTTTTAAATAGAATTGCTATTCTCGATACATACAAAGACGTAATTGCTGACCCAC
AATCAGTAACATCCATATTGGGAGATTTTTCAAAGGATGGTGACCCTGCTTGTATTTATTTACCTTGGTATTTTTCTTGCATCCTTCTGTGATTCAAAAAAG
TAAAATGTGGCTTTCTGAAATGATGGATAAGAGTCTACATCTTCTAGAAAAAATACATAAAGGAGTAGTTAAGCTCTGTAAATGTGCCACGAGGTCCAACACG
ACCATCGTAGGGTGAAGCCCACGTTTTCTTCCATGGCCTCAAAGGCCCTAGAACTTGCCTACCTTTCTGGCCTTACCTCCTAGCTACTTATCCATCTCTTGAA
CTTTATACTCTTGTATAAATTTCTAACTTTCAGAAAATGCCATACTCTGTTTTGGCACCACACATGTATATTTCCCCCTGGTACACTTGGAAGACTCTTATCC
ATCTGTGAAACCCTATGTTGTCATCACTTGGTCCATGAAATATTACCTGGCCAATATCCCACCATCACCTCAAACCCAATCACCCCCTCCTCTGTATGCTGTC
ACACCTATATTATTAAACTTATCACATTGCATTGTAATTACTTCCTGACCTTTGTATCTACTCTTTTAGTAACTGATGTATATATCTGAAAGGAGAGATTGTT
TCATTGTGCAATCAATAAATGTTTGATAAAATAAAGCCC SEQ ID NO 7 shows the alternative amino acid sequence of human GPR86
MNTTVMQGFNRSERCPRDTRIVQLVFPALYTVVFLTGILLNTLALWVFVHIPSSSTFIIYLKNTLVADLIMTLMLPFKIILSDSHLAPWQLRAFVCRFSSVIF
YETMYVGIVLLGLIAFDRFLKIIRPLRNIFLKKPVFAKTVSWIWFFLFFISLPNMWSNKEATPSSVKKCASLKGPLGLKWHQMVNNICQFWWTVFWMLVFYVV
IAKKVYDSYRKSKSKDRKNNKKLEGKVFVVVAVFFVCFAPFHFARVPYTHSQTNNKTDCRLQNQLFIAKETTLFLAATNICMDPLIYIFLCKKFTEKLPCMQG
RKTTASSQENHSSQTDNTTLG SEQ ID NOs: 8-20 show the knockout plasmid primer sequences.
TATACATATGTTCAGCAGTACCAACTC-SEQ ID NO: 8

ACACCAGTGTATAGATAGCAAGAAGTC-SEQ ID NO: 9 cccgtcgacATGCTTTCTTTTATGACAAAATCCTTG-SEQ ID NO: 10 aaagcggccGcGAACAGCAGCTGTGTCATCCGAGTG-SEQ ID NO: 11 aaaggcgcgccAGGCAAGAACAGCAGGATCAAGCGAAG-SEQ ID NO: 12 aaacaattGTGGCTTCTGAGGCTATGGAAAGAGAG-SEQ ID NO: 13

ATATGGCACATTTGGTCCGCACTGCAC-SEQ ID NO: 14

GATGAGGAATGATGTCACACAGATGAG-SEQ ID NO: 15

AAGGTCAAGATTAGCAAGTGATTCCAG-SEQ ID NO: 16

ATACCATACACTTACAGTCAAACCACC-SEQ ID NO: 17

GGTCTTCGCTTGATCCTGCTGTTCTTG-SEQ ID NO: 18

TTGGCTACCCGTGATATTGCTGAAGAG-SEQ ID NO: 19

GTCGTGACCCATGGCGATGCCTGCTTG-SEQ ID NO: 20

SEQ ID NO: 21
SEQ ID NO: 21 shows the knockout plasmid sequence

```
                                  >5' prF
                                     |
                                     |                                                                    2500
TTACAAATATGTTAAAACAAACATACAAGAGAACCTGAATACATATGTTCAGCAGTAACAACTCAAAAAGTCAAACAAATTAAATGTCCATCCGTAACAG
AATGTTTATACAATTTTGTTTGTATGTTCTCTTGGACTTATGTATACAAGTCGTCATTGTTGAGTTTTTCAGTTTGTTTAATTTACAGGTAGGCATTGTC

2600
CTTAACCAAAATATGGGAAAAGTTGTGTTTATCATTATGATCAGTGTCTATGTATTAACATAGACTAAGACAAAAATTAACACAGACTAAAATAAGCATG
GAATTGGTTTTATACCCTTTTCAACACAAATAGTAATACTAGTCACAGATACATAATTGTATCTGATTCTGTTTTTAATTGTGTCTGATTTTATTCGTAC

<5' prR
                                     |
                                     |                                                                    2700
AACACTTACACACTAGTATAAATATAAATGACTTCTTGCTATCTATACACTGGTGTTTAGAGTTTTCAAATAGTTGTTTTGTGTGTGTGTATGTTTTGTG
TTGTGAATGTGTGATCATATTTATATTTACTGAAGAACGATAGATATGTGACCACAAATCTCAAAAGTTTATCAACAAAACACACACACATACAAAACAC

2800
TGTGTGTGTGTGTGTGTGTGATGTGTGTGTGTGCATGTCCCCTTGTGAGTGTGGGCCTGTGTACACTATCACACACATATAGGTGTCAAAGGAACA
ACACACACACACACACACACACATACACACACACACACGTACAGGGGAACACTCACACCCGGACACATGTGATAGTGTGTGTATATCCACAGTTTCCTGT

2900
ACCTCAGGTGTCAGACATCATTTGTCATTTTGTTTGAGATAGAGTCTCCTTTTTACTGCTGCATATACCAGACCAACCACTCTGCATGCTTCTAAGGAAT
TGGAGTCCACAGTCTGTAGTAAACAGTAAAACAAACTCTATCTCAGAGGAAAAATGACGACGTATATGGTCTGGTTGGTGAGACGTACGAAGATTCCTTA

3000
TCTGTTTCCATATCCCCAATCTCGCAATACGAATGACAGAATTACATATACACATTACTGTGTCTACTTCTATATGGGCTCAGGAGATCTAAGTTTATTC
AGACAAAGGTATAGGGGTTAGAGCGTTATGCTTACTGTCTTAATGTATATGTGTAATGACACAGATGAAGATATACCCGAGTCCTCTAGATTCAAATAAG

>5' armF
                                                                                           |
                                                                                        >5' arm
                                                                                           |                3100
TTCCATGCTTGTGTGGCAAGTGCTTTACCTACTGCGTCATCTCCTATGTATTTCATCTTTAAACATATGCTTTCTTTTATGACAAAATCCTTGTAACTA
AAGGTACGAACACACCGTTCACGAAATGGATGACGCAGTAGAGGATACATAAAGTAGAAATTTTGTATACGAAAGAAAATACTGTTTTAGGAACATTGAT 3200
AATATTAAGCATTTCAAGTATTGCTGTGAATATATTGCCTGTTTCTGAAGAGATTTTTCTAATACTGATTTTCACTTCAGGACATCTGCTTGTAAACTAC
TTATAATTCGTAAAGTTCATAACGACACTTATATAACGGACAAAGACTTCTCTAAAAAGATTATGACTAAAAGTGAAGTCCTGTAGACGAACATTTGATG 3300
ATAGTGTATTTAACTCATTATCACTTTTGGTTACCCTAATTGGAAAGTTTTAAAAAATTCACATGCTCTAAGGAAAGTACCTCAGTAGATTTCAGAGTAA
TATCACATAAATTGAGTAATAGTGAAAACCAATGGGATTAACCTTTCAAAATTTTTTAAGTGTACGAGATTCCTTTCATGGAGTCATCTAAAGTCTCATT 3400
ATAAGAGTTCTCTCCTAGGAATATTTGAGTTCCCACTTCAACTTACATCCTTAGTGAAAATGAAAGCAAACATCTCAACATTTCTAATGTTATTATATGA
TATTCTCAAGAGAGGATCCTTATAAACTCAAGGGTGAAGTTGAATGTAGGAATCACTTTTACTTTCGTTTGTAGAGTTGTAAAGATTACAATAATATACT 3500
TGCATGTTAACTACATCACCAGAAGTCCCTTTGCTCTTTGCCTTGATCCAGCTCAGGAATCCTGGAGGTCTAGCAAAGGAAGTAGGTGTAGGCAACTTCC
ACGTACAATTGATGTAGTGGTCTTCAGGGAAACGAGAAACGGAACTAGGTCGAGTCCTTAGGACCTCCAGATCGTTTCCTTCATCCACATCCGTTGAAGG 3600
ATTACAGACCAGTTTGTCCCATCTGACCATACTGGTTGGACAATTTACAAATTTAACCTTAGACCTGAGTGTGTACCAGACAGAACTGAGTGTCCGTTCA
TAATGTCTGGTCAAACAGGGTAGACTGGTATGACCAACCTGTTAAATGTTTAAATTGGAATCTGGACTCACACATGGTCTGTCTTGACTCACAGGCAAGT 3700
GCTTCTTTTTCCTGTATCAATCATTGACTCTTGGCATAAGGACTTCAGGATGAAGTGAACCACTCCAGCTGCTCTCTCAGGGGTGTGGTGGGGTTGGGAC
CGAAGAAAAGGACATAGTTAGTAACTGAGAACCGTATTCCTGAAGTCCTACTTCACTTGGTGAGGTCGACGAGAGAGTCCCCACACCACCCCAACCCTG 3800
AAGGCAGGCTCTAAGTGCAAATTCTAGGGCCCAGTGGTAAGTTAGTGGTGGTCTCTATTACCACTATTTTGGGAAGGTGCTTAATTTCTTCATTTTGATT
TTCCGTCCGAGATTCACGTTTAAGATCCCGGGTCACCATTCAATCACACCAGAGATAATGGTGATAAAACCCTTCCACGAATTAAAGAAGTTAAAACTAA 3900
TTCACATCTAAAATAAGACTGGACTATGTTGTTATTGTAAGGGCTGTGATAACATAGTTACCTATAAATACCCATAGCTATTTTATTTTATTACCCGAGT
AAGTGTAGATTTTATTCTGACCTGATACAACAATAACATTCCCGACACTATTGTATCAATGGATATTATGGTATCGATAAAAATAAAATAATGAAACTCA
```

```
                                                                            4000
CTATTCTTAGTGCATAAAAGAATTCCAGTCTTTAATTTATTCCAGTCTTTAAATTATTCAGCAGGTCCTAAACACTGAAACTTTTCAATGCAATGGGGTT
GATAAGAATCACGTATTTTCTTAAGGTCAGAAATTAAATAAGGTCAGAAATTTAATAAGTCGTCCGAGGATTTGTGACTTTGAAAAGTTACGTACCCCAA

4100
TTTTTGTTTGTTTGTTTGTTTGTTTTTGTTTGTTTTTTGTTTTTTAGTTCTTCCTTCCCGGCCTTCGTGAACTAATAAGCCCACAGTATTCCTATT
AAAAACAAACAAACAAACAAACAAAACAAACAAAAAACAAAAAATCAAGAAGGAAGGGCCGGAAGCACTTGATTATTCGGGTGTCATAAGGATAA

4200
TTCTTTTTCATTGACTGAGGAAGCTCGCATGACATCGTCCATGACAGGCCTCACTGTGAGCATATGATGGACGTTCTTTTACCCCTAACTATATGAAAAG
AAGAAAAAGTAACTGACTCCTTCGAGCGTACTGTAGCAGGTACTGTCCGGAGTGACACTCGTATACTACCTGCAAGAAAATGGGGATTGATATACTTTTC

4300
GACACTGTTGTGTATTTCATCATAAAAAGGGGGCAAGTATTTCAGAGTGAGTATAAATAACTTCCCAAATGAGGGGAACAAAAAGCGACAGGTGGACAAG
CTGTGACAACACATAAGTAGTATTTTTCCCCCGTPCATAAAGTCTCACTCATATTTATTGAAGGGTTTACTCCCCTTGTTTTTTCGCTGTCCACCTGTTC

4400
CCCTTGAGCTACGGCCCGCAGCTTGGAGATGGCACTTCCACACAGGCCTAGGGAGCAGCGTGCAGAGAGCCCTTCCAAGAGGAACAGGCTTTTCCAAACA
GGGAACCTCGATGCCGGGCGTCGAACCTCTACCGTGAAGGTGTGTCCGGATCCCTCGTCGCACGTCTCTCCGGGAAGGTTCTCCTTGTCCGAAAGGTTGT

4500
AATATCAGCTAAGGAACTTACCAAGGGGAGCTCTCATTTAACAAGTGTGTAGTAGTTATGAAGATGACTCAGCTAGAGAAGACCAACCATGACCATGCAG
TTATAGTCGATTCCTTGAATGGTTCCCCTCGAGAGTAAATTGTTCACACATCATCAATACTTCTACTGAGTCGATCTCTTCTGGTTGGTACTGGTACGTC

4600
AGCTCAATCCATGAAACCCACATGTTGGAAAGATATAACTAACCCACTGAAGGAAAACACACACACACATACACACACACTCACACACTCACAATAAATA
TCGAGTTAGGTACTTTGGGTGTACAACCTCTATATTGATTGGGTGACTTCCTTTTGTGTGTGTGTGTATGTGTGTGTGAGTGTGTGAGTGTTATTTAT

4700
TGTATTTCACAACCAAAAGAATGTACCTTTGTGACCCTAGAAATGTCCATTGCTGATCAGTTCCTCTTTTCAAAGTTTCCCACAGTTGGCATTTTGAAAT
ACATAAAGTGTTGGTTTTCTTACATGGAACACTGGGATCTTTACAGGTAACGACTAGTCAAGGAGAAAAGTTTCAAAGGGTGTTAAACCGTAAAACTTTA

4800
TTGACCAAAATGTGATTTCTACTTCTCATATTATGAAATTATCCTGTACAGAATTTCCCTTGTTTAAAGTAAAAATTTCCAGACCTTCAATGTTATATTG
AACTGGTTTTACACTAAAGATGAAGAGTATAATACTTTAATAGGACATGTCTTAAAGGGAACAAATTTCATTTTTAAAGGTCTGGAAGTTACAATATAAC

4900
GATTGGGGGCTATTGAGAAATTTAAAATTGACTGTGTTTATGGTTAAAATTAACAATAAACCTACTTTAAAATATTGATTTTGCTAGGTTTTTATCCTCT
CTAACCCCCGATAACTCTTTAAATTTTAACTGACACAAATACCAATTTTAATTGTTATTTGGATGAAATTTTATAACTAAAACGATCCAAAAATAGGAGA

5000
TATAAAGCAAAAGGATATATATTTAAGTTAAGGGGCATTACATCAGTAAATCCTAACATATTTTAGCCAAAAAGAAAATTTTTACAATGTGCCATTTATT
ATATTTCGTTTTCCTATATATAAATTCAATTCCCCGTAATGTAGTCATTTAGGATTGTATAAAATCGGTTTTTCTTTTAAAAATGTTACACGGTAAATAA

5100
CCCTAGAGTTAACCAACGTTCCCTGGAAACACAGTACATTTCATTTTAAAATGTTCAAATGTGGAATCAATGGATTCCAAATTCTCAACCAAGTAATATA
GGGATCTCAATTGGTTGCAAGGGACCTTTGTGTCATGTAAAGTAAAATTTTACAAGTTTACACCTTAGTTACCTAAGGTTTAAGAGTTGGTTCATTATAT

5200
GGAATTACTAGTTAGCCAAACCCTGAAGACGGTCCATCTCTACGGTAAGCGCGTGGCAAGAACGGTGAAGTGAAACTTGCCATAGAGAACCACACATCCT
CCTTAATGATCAATCGGTTTGGGACTTCTGCCAGGTAGAGATGCCATTCGCGCACCGTTCTTGCCACTTCACTTTGAACGGTATCTCTTGGTGTGTAGGA

5300
CCCCAGGATCATCTGATTTCCTCTTTCCCTTCATCTGTCGGGCAGGGAAGCAGACTGTCACACATTGTAACTTTCTGCACACTCCCTGAGATTTAAAACG
GGGGTCCTAGTAGACTAAAGGAGAAAGGGAAGTAGACAGCCCGTCCCTTCGTCTGACAGTGTGTAACATTGAAAGACGTGTGAGGGACTCTAAATTTTGC

5400
AAACACTGTACCAATCTGAGGCCAGCCCTGATTCAAAACTTCTCTAAGTCTCAAGAATGGAGGTGGTTTCCCAAAAGGGCTTCCTAAAAGTGTCCACATG
TTTGTGACATGGTTAGACTCCGGTCGGGACTAAGTTTTGAAGAGATTCAGAGTTCTTACCTCCACCAAAGGGTTTTCCCGAAGGATTTTCACGGTGTGAC

5500
TAGCTCCACTCAAACTGGGCAATTCAAGGAACCCAAGCAATGAGCGGCTGGCATGTTTAGCTTTCACTGATGTGCCCTGGGTCGGTCCATCGGTCCCCCT
ATCGAGGTGAGTTTGACCCGTTAAGTTCCTTGGGTTCGTTACTCGCCGACCGTACAAATCGAAAGTGACTACACGGGACCCAGCCAGGTAGCCAGGGGGA

5600
CCCCCACACTCCTATGAAGTAGATGATGATTTCAAACTTGCTACATGAGAGAATGAGGTATATAGCTCTTAAAACATTTGTTTAAACATAATACCGAATA
GGGGGTGTGAGGATACTTCATCTACTACTAAAGTTTGAACGATGTACTCTCTTACTCCATATATCGAGAATTTTGTAAACAAATTTGTATTATGGCTTAT

5700
ATGCAGAGGTCCAGGAATAATAGCTACCACTTCTTGGGAAATGTGACTCATAATCTGCCACAGATCTAGGGATCAAAAGACTAACAGCAATGTCTGAAGA
TACGTCTCCAGGTCCTTATTATCGATGGTGAAGAACCCTTTACACTGAGTATTAGACGGTGTCTAGATCCCTAGTTTTTCTGATGTCGTTACAGACTTCT

5800
AAGGAAACAAAGCAAAACAAACAAGCAACCAACAACCAAAGCCTAGCCTTAGACATACAAACTTCTTGCACGCCCAGGCTGTAAGGGACAGAAGATGATT
TTCCTTTTGTTTCGTTTTGTTTGTTCGTTGGTTGTTGGTTTCGGATCGGAATCTGTATGTTGAAGAACGTGCGGGTCCGACATTCCCTGTCTTCTACTAA

5900
TGATTTTCAGATCAAGTCTTCTCCTCCTACTTGATTGTAATTTCATACTATTTTCTTCATCATTTTAACTCCTACTATTACATATGAAGTATTCAATAAG
ACTAAAAGTCTAGTTCAGAAGAGGAGGATGAACTAACATTAAAGTATGATAAAAGAAGTAGTAAAATTGAGGATGATAATGTATACTTCATAAGTTATTC
```

```
                                                                                                  6000
GTCGCTGAATGTGAATAATAAAAAGTAAAACACTGGGCCTAGAGAAATAGTTCGGCGGTTAAAGGGATTTTCCTGGCACCCACTCCAGGCAGCTCACAGT
CAGCGACTTACACTTATTATTTTTCATTTTGTGACCCGGATCTCTTTATCAAGCCGCCAATTTCCCTAAAAGGACCGTGGGTGAGGTCCGTCGAGTGTCA

6100
CACCTTGGACCCCAGCTCCAGGGAATCCAACACTTCTGGCCTCTGAGGGCACCTGAATGCATATGCGCCCTTACACATATAATTTAATATAATAAAATAG
GTGGAACCTGGGGTCGAGGTCCCTTAGGTTGTGAAGACCGGAGACTCCCGTGGACTTACGTATACGCGGAATGTGTATATTAAATTATATTATTTTATC

6200
ACCACATGTTAAGAATATGGCGTGGTGGCGTGCCTGCAGAGCCGGTGACAGCACTGGATTCAATACTCAGAACACGCAACCAATAACTACTGGTAAATGC
TGGTGTACAATTCTTATACCGCACCACCGCACGGACGTCTCGGCCACTGTCGTGACCTAAGTTATGAGTCTTGTGCGTTGGTTATTGATGACCATTTACG

6300
TCCAAAGGTCTAAAGACAAAGAGGTTCTAGAAAATGTGGGTATTACAGAAGCCCACAAGGGGAAATGAGGAAGGAAAAGCAGTATAAGAAAGCAGAACCT
AGGTTTCCAGATTTCTGTTTCTCCAAGATCTTTTACACCCATAATGTCTTCGGGTGTTCCCCTTTACTCCTTCCTTTTCGTCATATTCTTTCGTCTTGGA

6400
TTACTTCACAAGCTATTCGTGGGTTGAGCTAGTAACTGCCACAACTCATACAGCTGAGTCTCTTCCAAAACAAAGGTCAGTTTAATTTTTCTTATGAATT
AATGAAGTGTTCGATAAGCACCCAACTCGATCATTGACGGTGTTGAGTATGTCGACTCAGAGAAGGTTTTGTTTCCAGTCAAATTAAAAAGAATACTTAA
                           _____EXON 1_____>

6500
TGCTTGCTATAAAAGGTAAAAGGTGGTTAATTTTCTAGAAATCTAAATATAATATTCTGTAATCACGGGCTGCAAGCAATAAGGTACTTCATAACGCATG
ACGAACGATATTTTCCATTTTCCACCAATTTAAAAGAATCTTTAGATTATATTATAAGACATTAGTGCCCGACGTTCGTATTCCATGAAGTATTGCGTAC

6600
ACACACTACCCTGTACTCTTACATCTTAAATTAGGTTCTGTCACCGCCGTGTAGTGATTGGTGCTTGCTATTTGGACTTCACAAGGGTAGACATTAACAG
TGTGTGATGGGACATGAGAATGTAGAATTTAATCCAAGACAGTGGCGGCACATCACTAACCACGAACGATAAACCTGAAGTGTTCCCATCTGTAATTGTC

6700
GACTTTATAAAACAAAACTAAACTGAACAAAAACCAACCAAACAACAACAGCAACAAAACTAAGCTATGTGCTCAAAAAAGCTCTAGCCAAAGAATCAAA
CTGAAATATTTTGTTTTGATTTGACTTGTTTTTGGTTGGTTTGTTGTTGTCGTTGTTTTGATTCGATACACGAGTTTTTTCGAGATCGGTTTCTTAGTTT

6800
TCCGCTGAATGAGTTAAATAGTAAGTTTGTTTTTACAAGAAGTAGTTATCTGCCAATCCACAAGGACCCTTTGTTTACCTTCTTTGTAATGCCTGCTTAT
AGGCGACTTACTCAATTTATCATTCAAACAAAAATGTTCTTCATCAATAGACGGTTAGGTGTTCCTGGGAAACAAATGGAAGGAAACATACGGACGAATA

>ATG
                    |
                    |                                                                             6900
GTGTAATCTTTCTCTGTGTGCATGTTTATGTGTAATAGCTGATGCTCGGGACAATCAACACCACTGGGATGCAGGGCTTCAACAAGTCTGAGCGGTGCCC
CACATTAGAAAGAGACACACGTACAAATACACATTATCGACTACGAGCCCTGTTAGTTGTGGTGACCCTACGTCCCGAAGTTGTTCAGACTCGCCACGGG
                     M   L   G   T   I   N   T   T   G   M   Q   G   F   N   K   S   E   R   C   P>
                            _____MUSGPR86_____>
                            _____EXON 2_____>

<5' armR                              >7tm
                |                                    |
                |                                    |                                            7000
CAGGGACACTCGGATGACACAGCTGCTGTTCCCGGTTCTCTATACTGTGGTCTTCCTGGCAGGCATCCTGCTGAACACCGTGGCCCTCTGGGTGTTCGTC
GTCCCTGTGAGCCTACTGTGTCGACGACAAGGGCCAAGAGATATGACACCAGAAGGACCGTCCGTAGGACGACTTGTGGCACCGGGAGACCCACAAGCAG
   R   D   T   R   M   T   Q   L   L   F   P   V   L   Y   T   V   V   F   L   A   G   I   L   L   N   T   V   A   L   W   V   F   V>
      _____MUSGPR86_____>
      _____EXON 2_____>

7100
CACATCCCCAGCAATTCCACCTTTATCGTCTACCTCAAGAACACTCTGGTGGCAGACTTGATAATGGCACTCATGCTGCCTTTCAAAATCCTTTCCGACT
GTGTAGGGGTCGTTAAGGTGGAAATAGCAGATGGAGTTCTTGTGAGACCACCGTCTGAACTATTACCGTGAGTACGACGGAAAGTTTTAGGAAAGGCTGA
   H   I   P   S   N   S   T   F   I   V   Y   L   K   N   T   L   V   A   D   L   I   M   A   L   M   L   P   F   K   I   L   S   D>
      _____MUSGPR86_____>
      _____EXON 2_____>

7200
CACACCTTGCGCCCTGGCAGCTCCGAGGATTTGTGTGCACGCTCTCCTCCGTGGTCTTCTATGAGACGATGTATGTGGGTATCATGATGCTGGGCCTCAT
GTGTGGAACGCGGGACCGTCGAGGCTCCTAAACACGTGCGAGAGGAGGCACCAGAAGATACTCTGCTACATACACCCATAGTACTACGACCCGGAGTA
   S   H   L   A   P   W   Q   L   R   G   F   V   C   T   L   S   S   V   V   F   Y   E   T   M   Y   V   G   I   M   M   L   G   L   I>
      _____MUSGPR86_____>
      _____EXON 2_____>

7300
CGCTTTCGACAGGTTCCTCAAGATCATCATGCCGTTCAGGAAAACCTTTGTCAAAAAGACGGCTTTCGCAAAACAGTCTCCATTTCCGTCTGGTCCCTG
GCGAAAGCTGTCCAAGGAGTTCTAGTAGTACGGCAAGTCCTTTTGGAAACAGTTTTCTGCCGAAAGCGTTTTTGTCAGAGGTAAAGGCAGACCAGGGAC
   A   F   D   R   F   L   K   I   I   M   P   F   R   K   T   F   V   K   K   T   A   F   A   K   T   V   S   I   S   V   W   S   L>
      _____MUSGPR86_____>
      _____EXON 2_____>
```

```
                                                                                                7400
ATGTTCTTCATCTCCCTGCCAAACATGATCTTGAACAAGGAGGCAACGCCATCATCCGTGAAGAAGTGTGCATCTTTGAAGAGTCCCCTTGGGCTGTGGT
TACAAGAAGTAGAGGGACGGTTTGTACTAGAACTTGTTCCTCCGTTGCGGTAGTAAGGCACTTCTTCACACGTAGAAACTTCTAGGGGAACCCGACACCA
  M  F  F  I  S  L  P  N  M  I  L  N  K  E  A  T  P  S  S  V  K  K  C  A  S  L  K  S  P  L  G  L  W>
_____MUSGPR86_____>
_____EXON 2_____>

7500
GGCATCAGGTGGTCAGTCACACCTGCCAGTTCATTTTCTGGGCTGTGTTTATTCTGATGCTTCTGTTTTATGCGGTGATTACCAAAAAGGTGTACAACTC
CCGTAGTCCACCAGTCAGTGTGGACGGTCAAGTAAAAGACCCGACACAAATAAGACTACGAAGACAAAATACGCCACTAATGGTTTTTCCACATGTTGAG
 W  H  Q  V  V  S  H  T  C  Q  F  I  F  W  A  V  F  I  L  M  L  L  F  Y  A  V  I  T  K  K  V  Y  N  S>
_____MUSGPR86_____>
_____EXON 2_____>

7600
CTATAGGAAGTTTAGGAGTAAGGACAGCAGGCACAAGCGGCTGGAGGTGAAGGTATTTATCGTCATGGCTGTCTTCTTTGTCTGCTTTGCCCCACTGCAT
GATATCCTTCAAATCCTCATTCCTGTCGTCCGTGTTCGCCGACCTCCACTTCCATAAATAGCAGTACCGACAGAAGAAACAGACGAAACGGGTGACGTA
  Y  R  K  F  R  S  K  D  S  R  H  K  R  L  E  V  K  V  F  I  V  M  A  V  F  F  V  C  F  A  P  L  H>
_____MUSGPR86_____>
_____EXON 2_____>

>hetF
          |
          |                                                                                     7700
TTTGTCAGAATACCATACACTTACAGTCAAACCACCAATAAGACTGACTGTAGGTTAGAAAACCAGCTGTTTATTGCTAAAGAAGCAACTCTCTTTCTGG
AAACAGTCTTATGGTATGTGAATGTCAGTTTGGTGGTTATTCTGACTGACATCCAATCTTTTGGTCGACAAATAACGATTTCTTCGTTGAGAGAAAGACC
  F  V  R  I  P  Y  T  Y  S  Q  T  T  N  K  T  D  C  R  L  E  N  Q  L  F  I  A  K  E  A  T  L  F  L>
_____MUSGPR86_____>
_____EXON 2_____>

>3' armF
                                                                               |
                                                                            >3' arm
                                                                               |
                                                                               |                7800
CAACAACTAACATTTGTATGGACCCCTTAATATACATAATTTTATGCAAGAAGTTCACACAAAAGGTGCCATGTGTGAGATGGGGAAAGGCAAGAACAGC
GTTGTTGATTGTAAACATACCTGGGGAATTATATGTATTAAAATACGTTCTTCAAGTGTGTTTTCCACGGTACACACTCTACCCCTTTCCGTTCTTGTCG
 A  T  T  N  I  C  M  D  P  L  I  Y  I  I  L  C  K  K  F  T  Q  K  V  P  C  V  R  W  G  K  A  R  T  A>
_____MUSGPR86_____>
_____EXON 2_____>

<hetR                    >Stop
              |                        |
              |                        |                                                        7900
AGGATCAAGCGAAGACCACCACAGTAGTCAGACAGACAACATCACCCTAGCCTGACCACTGTGTCCCACAGGTTAATTTCACGCATGGCCTCACGTCTAT
TCCTAGTTCGCTTCTGGTGGTGTCATCAGTCTGTCTGTTGTAGTGGGATCGGACTGGTGACACAGGGTGTCCAATTAAAGTGCGTACCGGAGTGCAGATA
  G  S  S  E  D  H  H  S  S  Q  T  D  N  I  T  L  A  *>
_____MUSGPR86_____>
_____EXON 2_____>

8000
TTATGGATGGGATTTCAAAAGATCATTTATGTGGAGACCTCATTTAAGCATTACAGGAAAAAAGAGGGGAACAAACAGTTCCCTACATTTTATTATCCTA
AATACCTACCCTAAAGTTTTCTAGTAAATACACCTCTGGAGTAAATTCGTAATGTCCTTTTTTCTCCCCTTGTTTGTCAAGGGATGTAAAATAATAGGAT
_____EXON 2_____>

8100
GTGTATGGAAAAACATTATGCCCATTTTAACCACATAGACGTATTTATAAGCAGGATAAATTAAGAGACCATGTAATACAGCAAATGGCCACTAGATGTC
CACATACCTTTTTGTAATACGGGTAAAATTGGTGTATCTGCATAAATATTCGTCCTATTTAATTCTCTGGTACATTATGTCGTTTACCGGTGATCTACAG
_____EXON 2_____>

8200
ACCTTTTCAAGGGCATTCATGTACTATGGAAAAGGTTATGGGAAACAGGTTTGCCTGAAAAATCTTCCTTCTAGTTACCACCCCACCATCTCTTCACAC
TGGAAAAGTTCCCGTAAGTACATGATACCTTTTCCAATTACCCTTTGTCCAAACGGACTTTTAGAAGGAAGATCAATGGTGGGTGGTAGAGAAGTGTG
_____EXON 2_____>

8300
ATATATTCCCTAAAACACCAGGCTGGCTTTTACAGCCTTCAGAATGCTGACACTTGTGAACAGAAACCAACCAACTTGCATATCCAGTGCCTGTGTGGAA
TATATAAGGGATTTTGTGGTCCGACCGAAAATGTCGGAAGTCTTACGACTGTGAACACTTGTCTTTGGTTGGTTGAACGTATAGGTCACGGACACACCTT
_____EXON 2_____>

8400
AGGCTAAGGTGGGGGCTCAAAGAGATGCAGTCTGAGGAACCAAAGTGGGTTGGTCAAAATAACCCCAGGCATCTCAAAAGATTTCCTCCTTACAAGTGCA
TCCGATTCCACCCCGAGTTTCTCTACGTCAGACTCCTTGGTTTCACCCAACCAGTTTTATTGGGGTCCGTAGAGTTTTCTAAAGGAGGAATGTTCACGT
_____EXON 2_____>

8500
AAGGGCTGCTCCTACATCTAAACAGAGCACCAGAAGAGAGGCACATGCAACAGGCAAAGCCAGTTCACAGCCATGTGCAATCCAGAGAGGGGAAGTGTTT
TTCCCGACGAGGATGTAGATTTGTCTCGTGGTCTTCTCTCCGTGTACGTTGTCCGTTTCGGTCAAGTGTCGGTACACGTTAGGTCTCTCCCCTTCACAAA
_____EXON 2_____>
```

-continued

```
                                                                                         8600
AGTCAGCAAAACCTTCCTGGGCAACAGCATCTGCATCCTGTTGGAAAATACTTATTTCCCTCACTGTTTATCTATAAATTAGGTTCCTTGCTACACACTG
TCAGTCGTTTTGGAAGGACCCGTTGTCGTAGACGTAGGACAACCTTTTATGAATAAAGGGAGTGACAAATAGATATTTAATCCAAGGAACGATGTGTGAC
_____EXON 2_____>

8700
TCTTATATTAACTGCTTTCATTCTTAGCCACATTTCCCAAAAACAGGGTTCGTAAAAAGACAGCAAAATCACACATTTTTACAAAAGAAATGGGGTAAGG
AGAATATAATTGACGAAAGTAAGAATCGGTGTAAAGGGTTTTTGTCCCAAGCATTTTTCTGTCGTTTTAGTGTGTAAAAATGTTTTCTTTACCCCATTCC
_____EXON 2_____>

8800
ATATCCTAGACGGGATATTTGTTGTACACTATCCTTAGTGCATGTGAGCAAGGGGATGGTTGGCCTGGCATTAGTAAATATTCATGTGGAAGATTTTTCA
TATAGGATCTGCCCTACAAACAACATGTGATAGGAATCACGTACACTGGTTCCCCTACCAACCGGACCGTAATCATTATAAGTACACCCTTCTAAAAAGT
_____EXON 2_____>

8900
AAGCCTGATTCATTTTATTTGGGCCTATCTACTTCCCTGGATCTCATTATGGGTTTAAGAAAATTAAAATATGTGGCTGGTGATGCTGGGTTTTCTGGAG
TTCGGACTAAGTAAAATAAACCCGGATAGATGAAGGGACCTAGAGTAATACCCAAATTCTTTTAATTTTATACACCGACCACTACGACCCAAAAGACCTC
_____EXON 2_____>

<3' armR
                                                                              |
                                                                              |          9000
AACACGACGACTCTTCCCCTAACCGCGCCTGTAATGTGAAATCCTGGCTTCTCTCTTTCCATAGCCTCAGAAGCCACAGAGGCAAGAGAACTTCCTTGTC
TTGTGCTGCTGAGAAGGGGATTGGCGCGGACATTACACTTTAGGACCGAAGAGAGAAAGGTATCGGAGTCTTCGGTGTCTCCGTTCTCTTGAAGGAACAG
_____EXON 2_____>

<3' scr         >3' prF
            |               |
            |               |                                                            9100
TTCCTGGAATCACTTGCTAATCTTGACCTTTACAAACTCCATTTAATATGGCACATTTGGTCCGCACTGCACTGTACATAGAACCTTCCATCTGACCCAC
AAGGACCTTAGTGAACGATTAGAACTGGAAATGTTTGAGGTAAATTATACCGTGTAAACCAGGCGTGACGTGACATGTATCTTGGAAGGTAGACTGGGTG
_____EXON 2_____>

9200
TTTGTAAGTTCCTATTGATTAGTGACACCCAAAGTTGCTGTCCCTTACTCCAGGTAACCTTACCTGCCCAACCTCCTCCGAGTCCTCCAGCCCAGTCACT
AAACATTCAAGGATAACTAATCACTGTGGGTTTCAACGACAGGGAATGAGGTCCATTGGAATGGACGGGTTGGAGGAGGCTCAGGAGGTCGGGTCAGTGA
_____EXON 2_____>

<3' prR                                                   >polyA
            |                                                         |
            |                                                         |                  9300
TCCTCATCTGTGTGACATCATTCCTCATCTACTTATCGAATTGATTTAGGATAATTTGCTAAATATGCACTGTGCAATTAATAAATTTTGCTAAAACAAA
AGGAGTAGACACACTGTAGTAAGGAGTAGATGAATAGCTTAACTAAATCCTATTAAACGATTTATACGTGACACGTTAATTATTTAAAACGATTTTGTTT
_____EXON 2_____>
```

---

We claim:

1. An in vitro method of identifying a candidate molecule for the treatment, prophylaxis or alleviation of pain, the method comprising:
   exposing a candidate molecule to a GPR86 polypeptide comprising the amino acid sequence shown in SEQ ID NO:7 or a sequence identical to at least 98% of SEQ ID NO:7, wherein the candidate molecule is not a protein and is not an antibody;
   measuring binding of the candidate molecule to the GPR86 polypeptide, wherein a candidate molecule which binds to GPR86 is a candidate for treatment, prophylaxis, or alleviation of pain.

2. The method of claim 1 wherein the GPR86 polypeptide comprises the amino acid sequence shown in SEQ ID NO: 7.

3. The method of claim 1 further comprising: testing in vitro to determine that the candidate is an antagonist of GPR86.

4. The method of claim 3 wherein the testing comprises:
   contacting (a) a cell comprising a GPR86 receptor polypeptide comprising the amino acid sequence shown in SEQ ID NO:7 or a sequence identical to at least 98% of SEQ ID NO:7 coupled with G-protein $G_i$ with (b) the candidate compound; and
   determining cyclic AMP (cAMP) level in said cell, wherein when said level is raised as a result of said contacting, the candidate compound is identified as a molecule suitable for the treatment, prophylaxis, or alleviation of pain.

5. The method of claim 3 wherein the testing comprises:
   contacting (a) a cell comprising a GPR86 receptor polypeptide comprising the amino acid sequence shown in SEQ ID NO: 7 or a sequence identical to at least 98% of SEQ ID NO: 7 coupled with $G_{\alpha 16}$ with (b) the candidate compound; and
   determining intracellular calcium level in said cell, wherein when said level is lowered as a result of said contacting, the candidate compound is identified as a molecule suitable for the treatment, prophylaxis, or alleviation of pain.

6. An in vitro method of identifying a molecule suitable for the treatment, prophylaxis or alleviation of pain, the method comprising:
   contacting (a) a cell comprising a GPR86 receptor polypeptide comprising the amino acid sequence shown in SEQ ID NO: 7 or a sequence identical to at least 98% of SEQ ID NO: 7 coupled with G-protein $G_i$ with (b) a candidate compound, wherein the candidate molecule is not a protein and is not an antibody; and
   determining cyclic AMP (cAMP) level in said cell, wherein when said level is raised as a result of said contacting, the candidate compound is identified as a molecule suitable for the treatment, prophylaxis, or alleviation of pain.

7. The method of claim 6 wherein the GPR86 polypeptide comprises the amino acid sequence shown in SEQ ID NO: 7.

8. An in vitro method of identifying a molecule suitable for the treatment, prophylaxis or alleviation of pain, the method comprising:
   contacting (a) a cell comprising a GPR86 receptor polypeptide comprising the amino acid sequence shown in SEQ ID NO: 7 or a sequence identical to at least 98% of SEQ ID NO: 7 coupled with $G_{\alpha 16}$ with (b) a candidate compound, wherein the candidate molecule is not a protein and is not an antibody; and
   determining intracellular calcium level in said cell, wherein when said level is lowered as a result of said contacting, the candidate compound is identified as a molecule suitable for the treatment, prophylaxis, or alleviation of pain.

9. The method of claim 8 wherein the GPR86 polypeptide comprises the amino acid sequence shown in SEQ ID NO: 7.

* * * * *